(12) United States Patent  (10) Patent No.: US 8,518,985 B2
Fischer et al.  (45) Date of Patent: Aug. 27, 2013

(54) HALOALKYLMETHYLENEOXYPHENYL-SUBSTITUTED KETOENOLS

(75) Inventors: Reiner Fischer, Monheim (DE); Thomas Bretschneider, Lohmar (DE); Stefan Lehr, Liederbach (DE); Eva-Maria Franken, Lyons (FR); Olga Malsam, Rosrath (DE); Arnd Voerste, Cologne (DE); Ulrich Gorgens, Ratingen (DE); Jan Dittgen, Frankfurt (DE); Dieter Feucht, Eschborn (DE); Isolde Hauser-Hahn, Leverkusen (DE); Christopher Hugh Rosinger, Hofheim (DE); Alfred Angermann, Kriftel (DE)

(73) Assignee: Bayer CropScience AG, Monheim (DE)

( * ) Notice: Subject to any disclaimer, the term of this patent is extended or adjusted under 35 U.S.C. 154(b) by 319 days.

(21) Appl. No.: 12/659,536

(22) Filed: Mar. 11, 2010

(65) Prior Publication Data

US 2010/0311593 A1 Dec. 9, 2010

(30) Foreign Application Priority Data

Mar. 11, 2009 (EP) .................................. 09154888

(51) Int. Cl.
*A01N 43/36* (2006.01)
*A61K 31/40* (2006.01)

(52) U.S. Cl.
USPC ........... 514/425; 514/409; 548/407; 548/408; 548/542; 548/544

(58) Field of Classification Search
USPC .......................................... 548/408, 544, 542
See application file for complete search history.

(56) References Cited

U.S. PATENT DOCUMENTS

| | | |
|---|---|---|
| 2,842,476 A | 7/1958 | Schreiber |
| 3,542,809 A | 11/1970 | Nakanishi |
| 4,091,006 A | 5/1978 | Durden, Jr. et al. |
| 4,175,135 A | 11/1979 | Haines |
| 4,209,532 A | 6/1980 | Wheeler |
| 4,256,657 A | 3/1981 | Wheeler |
| 4,256,658 A | 3/1981 | Wheeler |
| 4,256,659 A | 3/1981 | Wheeler |
| 4,257,858 A | 3/1981 | Wheeler |
| 4,283,348 A | 8/1981 | Wheeler |
| 4,303,669 A | 12/1981 | D'Silva |
| 4,338,122 A | 7/1982 | Wheeler |
| 4,351,666 A | 9/1982 | Koerwer |
| 4,409,153 A | 10/1983 | Hodakowski |
| 4,436,666 A | 3/1984 | Wheeler |
| 4,526,723 A | 7/1985 | Wheeler et al. |
| 4,551,547 A | 11/1985 | Wheeler |
| 4,613,617 A | 9/1986 | Sousa |
| 4,623,727 A | 11/1986 | Hübele |
| 4,632,698 A | 12/1986 | Wheeler |
| 4,639,266 A | 1/1987 | Heubach et al. |
| 4,659,372 A | 4/1987 | Wheeler |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |
| 4,944,790 A | 7/1990 | Moser et al. |
| 4,985,063 A | 1/1991 | Fischer et al. |
| 5,013,659 A | 5/1991 | Bedbrook et al. |
| 5,045,560 A | 9/1991 | Fischer et al. |
| 5,094,681 A | 3/1992 | Krämer et al. |
| 5,116,836 A | 5/1992 | Fischer et al. |

(Continued)

FOREIGN PATENT DOCUMENTS

| | | |
|---|---|---|
| CA | 1 162 071 A | 2/1984 |
| CA | 2 077 896 C | 9/1991 |

(Continued)

OTHER PUBLICATIONS

W.T. Ruegg et al., Weed Research, 47(4), 271-275, 271 (2006); L. M. Abell et al. Target-Site Directed Herbicide Design in, Pest Control With Enhanced Environmental Safety 15-37 (ACS Symposium Series; American Chemical Society, S. Duke, et al. eds, 1993).*
L. M. Abell et al. Target-Site Directed Herbicide Design in, Pest Control With Enhanced Environmental Safety 15-37 (ACS Symposium Series; American Chemical Society, S. Duke, et al. eds, 1993).*
S.C. Knight et al., Annual Review of Phytopathology 35, 349-372, 357 (1997).*
W.T. Ruegg et al., Weed Research, 47(4), 271-275, 271 (2006).*
Askani, R., "Zur reaktion von cyclohexadien-(1.3) mit azodicarbonsäure-diäthylester," Chemische Berichte 98(8):2551-2556, Wiley-VCH Verlags GmbH, Germany (1965).
Baciocchi, E., et al.,"Dimethyl arylmalonates from cerium (IV) ammonium nitrate promoted reactions of dimethyl malonate with aromatic compounds in methanol," Tetrahedron Lett. 27(24):2763-2766, Pergamon Press Ltd, Great Britain (1986).

(Continued)

Primary Examiner — James O Wilson
Assistant Examiner — Alexander R Pagano
(74) Attorney, Agent, or Firm — Sterne, Kessler, Goldstein & Fox P.L.L.C.

(57) ABSTRACT

The invention relates to novel compounds of the formula (I), (I)

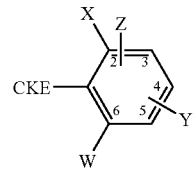

in which W, X, Y, Z and CKE are each as defined above,
to several methods and intermediates for preparation thereof and to the use thereof as pesticides and/or herbicides.
The invention also relates to selective herbicidal compositions which comprise firstly haloalkylmethyleneoxyphenyl-substituted ketoenols and secondly a compound which improves crop plant compatibility.
The present invention further relates to the enhancement of the action of crop protection compositions comprising especially haloalkylmethyleneoxyphenyl-substituted ketoenols, by the addition of ammonium or phosphonium salts and optionally penetration enhancers, to the corresponding compositions, to methods for production thereof and to the use thereof in crop protection as insecticides and/or acaricides and/or for preventing undesired plant growth.

12 Claims, No Drawings

(56) References Cited

U.S. PATENT DOCUMENTS

| | | |
|---|---|---|
| 5,126,920 A | 6/1992 | Cardashian et al. |
| 5,215,570 A | 6/1993 | Burckhardt et al. |
| 5,225,434 A | 7/1993 | Bertram et al. |
| 5,258,527 A | 11/1993 | Krauskopf et al. |
| 5,262,383 A | 11/1993 | Fischer et al. |
| 5,306,695 A | 4/1994 | Stark et al. |
| 5,314,863 A | 5/1994 | Löher et al. |
| 5,332,720 A | 7/1994 | Krüger et al. |
| 5,336,662 A | 8/1994 | Lee |
| 5,380,852 A | 1/1995 | Schütze et al. |
| 5,393,729 A | 2/1995 | Fischer et al. |
| 5,401,700 A | 3/1995 | Sohn et al. |
| 5,462,912 A | 10/1995 | Hioki et al. |
| 5,462,913 A | 10/1995 | Fischer et al. |
| 5,494,890 A | 2/1996 | Cederbaum et al. |
| 5,500,367 A | 3/1996 | Hain et al. |
| 5,504,057 A | 4/1996 | Fischer et al. |
| 5,516,750 A | 5/1996 | Willms et al. |
| 5,538,937 A | 7/1996 | Hasebe et al. |
| 5,565,450 A | 10/1996 | Fischer et al. |
| 5,567,671 A | 10/1996 | Fischer et al. |
| 5,589,469 A | 12/1996 | Fischer et al. |
| 5,610,122 A | 3/1997 | Fischer et al. |
| 5,622,917 A | 4/1997 | Fischer et al. |
| 5,683,965 A | 11/1997 | Bachmann et al. |
| 5,689,046 A | 11/1997 | Schröder et al. |
| 5,700,758 A | 12/1997 | Rösch et al. |
| 5,705,476 A | 1/1998 | Hoffarth |
| 5,728,831 A | 3/1998 | Lee |
| 5,739,079 A | 4/1998 | Holdgrün et al. |
| 5,792,755 A | 8/1998 | Sagenmüller et al. |
| 5,808,135 A | 9/1998 | Fischer et al. |
| 5,811,374 A | 9/1998 | Bertram et al. |
| 5,830,825 A | 11/1998 | Fischer et al. |
| 5,830,826 A | 11/1998 | Fischer et al. |
| 5,840,661 A | 11/1998 | Fischer et al. |
| 5,945,444 A | 8/1999 | Fischer et al. |
| 5,972,839 A | 10/1999 | Ziemer et al. |
| 5,977,029 A | 11/1999 | Fischer et al. |
| 5,994,274 A | 11/1999 | Fischer et al. |
| 6,071,937 A | 6/2000 | Bretschneider et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,251,827 B1 | 6/2001 | Ziemer et al. |
| 6,251,833 B1 | 6/2001 | Erdelen et al. |
| 6,288,102 B1 | 9/2001 | Hagemann et al. |
| 6,316,486 B1 | 11/2001 | Lieb et al. |
| 6,358,887 B1 * | 3/2002 | Fischer et al. ............ 504/284 |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,515,184 B1 | 2/2003 | Fischer et al. |
| 6,555,499 B1 | 4/2003 | Glock et al. |
| 6,589,976 B1 | 7/2003 | Fischer et al. |
| 6,602,823 B1 | 8/2003 | Röchling et al. |
| 6,608,211 B1 | 8/2003 | Hagemann et al. |
| 6,645,914 B1 | 11/2003 | Woznica et al. |
| 6,861,391 B1 | 3/2005 | Fischer et al. |
| 6,894,005 B1 | 5/2005 | Maetzke et al. |
| 6,906,007 B2 | 6/2005 | Fischer et al. |
| 6,958,383 B2 | 10/2005 | Desmazeau et al. |
| 6,974,827 B2 | 12/2005 | Fischer et al. |
| 2003/0171219 A1 | 9/2003 | Lieb et al. |
| 2003/0216260 A1 | 11/2003 | Ruther et al. |
| 2003/0224939 A1 | 12/2003 | Miles |
| 2004/0224844 A1 | 11/2004 | Bickers et al. |
| 2005/0009880 A1 | 1/2005 | Cottrell et al. |
| 2005/0037922 A1 | 2/2005 | Bickers et al. |
| 2005/0049145 A1 | 3/2005 | Bickers et al. |
| 2005/0054535 A1 | 3/2005 | Fischer et al. |
| 2005/0070707 A1 | 3/2005 | Fischer et al. |
| 2005/0096386 A1 | 5/2005 | Cottrell et al. |
| 2005/0256000 A1 | 11/2005 | Schaper et al. |
| 2006/0095981 A1 | 5/2006 | Hain et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0032539 A1 | 2/2007 | Himmler |
| 2007/0066488 A1 | 3/2007 | Fischer et al. |
| 2007/0129252 A1 | 6/2007 | Fischer et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0167188 A1 | 7/2008 | Fischer et al. |
| 2008/0188371 A1 | 8/2008 | Fischer et al. |
| 2008/0220973 A1 | 9/2008 | Fischer et al. |
| 2008/0305955 A1 | 12/2008 | Bretschneider et al. |
| 2008/0318776 A1 | 12/2008 | Fischer et al. |
| 2009/0029858 A1 | 1/2009 | Fischer et al. |
| 2009/0137393 A1 | 5/2009 | Fischer et al. |
| 2009/0209513 A1 | 8/2009 | Fischer et al. |
| 2009/0215624 A1 | 8/2009 | Fischer et al. |
| 2009/0227563 A1 | 9/2009 | Fischer et al. |
| 2009/0239906 A1 | 9/2009 | Fischer et al. |
| 2009/0298828 A1 | 12/2009 | Fischer et al. |
| 2009/0305891 A1 | 12/2009 | Fischer et al. |
| 2010/0004127 A1 | 1/2010 | Fischer et al. |
| 2010/0009850 A1 | 1/2010 | Fischer et al. |
| 2010/0168226 A1 | 7/2010 | Fischer et al. |
| 2012/0015807 A1 * | 1/2012 | Fischer et al. ............ 504/130 |

FOREIGN PATENT DOCUMENTS

| | | |
|---|---|---|
| CA | 2 382 432 A1 | 3/2001 |
| CA | 2 671 179 A1 | 6/2008 |
| CA | 2 695 032 A1 | 2/2009 |
| CA | 2 700 292 A1 | 4/2009 |
| DE | 10 2005 059 892 A1 | 6/2007 |
| DE | 102006050148 A1 * | 4/2008 |
| EP | 0 142 924 A2 | 5/1985 |
| EP | 0 193 259 A1 | 9/1986 |
| EP | 0 221 044 A1 | 5/1987 |
| EP | 0 242 236 A1 | 10/1987 |
| EP | 0 242 246 A1 | 10/1987 |
| EP | 0 257 993 A2 | 3/1988 |
| EP | 0 262 399 A2 | 4/1988 |
| EP | 0 346 620 A1 | 12/1989 |
| EP | 0 442 077 A2 | 12/1990 |
| EP | 0 415 211 A2 | 3/1991 |
| EP | 0 453 086 A2 | 10/1991 |
| EP | 0 502 492 A2 | 3/1992 |
| GB | 2 266 888 A | 11/1993 |
| JP | 60-087254 | 5/1985 |
| JP | 11-152273 | 6/1999 |
| JP | 2000-53670 A | 2/2000 |
| JP | 14-205984 | 7/2002 |
| WO | WO 84/02919 A1 | 8/1984 |
| WO | WO 89/10396 A1 | 11/1989 |
| WO | WO 91/19806 A1 | 12/1991 |
| WO | WO 92/00377 A1 | 1/1992 |
| WO | WO 92/11376 A1 | 7/1992 |
| WO | WO 92/14827 A1 | 9/1992 |
| WO | WO 92/16108 A1 | 10/1992 |
| WO | WO 95/14012 A1 | 5/1995 |
| WO | WO 95/17817 A1 | 7/1995 |
| WO | WO 96/11574 A1 | 4/1996 |
| WO | WO 96/21652 A1 | 7/1996 |
| WO | WO 96/33270 A1 | 10/1996 |
| WO | WO 98/13361 A1 | 4/1998 |
| WO | WO 98/35553 A1 | 8/1998 |
| WO | WO 98/38856 A1 | 9/1998 |
| WO | WO 99/47525 A1 | 9/1999 |
| WO | WO 00/68196 A1 | 11/2000 |
| WO | WO 01/17351 A1 | 3/2001 |
| WO | WO 01/17353 A1 | 3/2001 |
| WO | WO 02/24704 A1 | 3/2002 |
| WO | WO 02/34048 A1 | 5/2002 |
| WO | WO 03/028466 A2 | 4/2003 |
| WO | WO 03/059065 A1 | 7/2003 |

| WO | WO 03/062244 A1 | 7/2003 |
| WO | WO 2007/023719 A1 | 3/2007 |
| WO | WO 2007/023764 A1 | 3/2007 |
| WO | WO 2007/024782 A2 | 3/2007 |
| WO | WO 2007/027777 A2 | 3/2007 |
| WO | WO 2008/067873 A1 | 6/2008 |
| WO | WO 2008/067910 A1 | 6/2008 |
| WO | WO 2008/071405 A1 | 6/2008 |
| WO | WO 2008067873 A1 * | 6/2008 |
| WO | WO 2008/110307 A1 | 9/2008 |
| WO | WO 2008/110308 A2 | 9/2008 |
| WO | WO 2008/121065 A1 | 10/2008 |
| WO | WO 2008/121066 A1 | 10/2008 |
| WO | WO 2008/138551 A2 | 11/2008 |
| WO | WO 2008/145336 A1 | 12/2008 |
| WO | WO 2009/019005 A2 | 2/2009 |
| WO | WO 2009/019015 A1 | 2/2009 |
| WO | WO 2009/049851 A1 | 4/2009 |
| WO | WO 2009/074314 A1 | 6/2009 |
| WO | WO 2009/115262 A1 | 9/2009 |
| WO | WO 2010/040460 A2 | 4/2010 |
| WO | WO 2010/063378 A1 | 6/2010 |
| WO | WO 2010/102758 | 9/2010 |
| ZA | 9805601 | 1/1999 |

OTHER PUBLICATIONS

Baur, P., et al., "Polydisperse ethoxylated fatty alcohol surfactants as accelerators of cuticular penetration. 1. effects of ethoxy chain length and the size of the penetrants," *Pesticide Science* 51(2):131-152, John Wiley & Sons, Great Britian (1997).

Bhattacharya B., "Isoquinoline derivatives: part XVIII-formation of l-alkyl-(or alkaryl or aryl)-3-methyl-7-chloro-(or 5-chloro)-isoquinolines", *Indian Journal of Chemistry* 6:341-345, National Institute of Science Communication and Information Resources, Dr K S Krishnan Marg (Near Pusa Gate), New Delhi, India (1968).

Boltze, K. and Heidenbluth, K., "Zur synthese 3-substituierter 4-hydroxy-pyrone-(2), Iringschlüsse mit malonsäure-dichloriden," *Chemische Berichte* 91(12):2849-2853, Wiley-VCH Verlags GmbH, Weinheim (1958).

Braun, H., et al. "The general mitochondrial processing peptidase from potato is an integral part of cytochrome c reductase of the respiratory chain," *The Embo Journal* 11(9):3219-3227, Nature Publishing Group, London, United Kingdom (1992).

Campbell, A.C., et al., "Synthesis of (E)- and (Z)- pulvinones", *Journal of the Chemical Society, Perkin Transactions* 1:1567-1576, Royal Society of Chemistry, United Kingdom (1985).

Chambers, M.S., et al., "An asymmetric synthesis of thiotetronic acids using chirality transfer via an allyl xanthate-to-dithiocarbonate rearrangement. X-Ray crystal structure of (5R)-2, 5-dihydro-4-hydroxy-5-methyl-3-phenyl-5-prop-1'enyl-2-oxothiophene," *Journal of the Chemical Socierty, Chemical Communications* 16(6):1228-1230, Royal Society of Chemistry, Cambridge, United Kingdom (1987).

Chirazi, A.M., et al.,"Synthesen von heterocyclen, 184. zur synthese von kawakctonderivaten," *Archiv der Pharmazie* 309(7):558-564, German Pharmaceutical Society, Germany (1975).

Christou, P., "Transformation technology", *Trends in Plants Science* 1(12): 423-431, Elsevier Science Ltd. (1996).

Compagnon, P.L. and Miocque, M., "Addition Des Reactifs Nucleophiles Sur La Triple Liaison Nitrile," Ann. Chim., 14(5):11-27, Wiley Interscience, France (1970).

Dannenberg, H. and Dresler, D., "Versuche zur synthese des "Steranthrens" III. 3,4-aceperinaphthan und 6,7-aceperinaphthan," *Justus Liebigs Ann. Chem.* 585(6):1-15, Verlag Chemie, Germany (1954).

Diels, O., et al., "Über das aus cyclopentadien und azoester entstehende endomethylen-piperidazin und seine überführung in 1,3-diamino-cyclopentan," *Justus Liebigs Ann. Chem.* 443:242-262, Verlag Chemie, Germany (1925).

Edward, J.T. and Jitrangsri, C., "Stereochemistry of the Bucherer-Bergs and Strecker Reactions of 4-*tert*-Butycyclohexanone," *Can. J. Chem.* 53:3339-3350, NRC Research Press, Canada (1975).

Edwards, R.L., et al., "Constituents of the higher fungi. Part IV. involutin, a diphenyl-cyclopenteneone from *Paxillus involutus* (Oeder ex Fries)," *Journal of the Chemical Society, Organic Articles* 6:405-409, Royal Society of Chemistry, Cambridge, United Kingdom (1967).

Ferri, C., "Reaktionen der organischen Synthese," pp. 212 and 513-515 (1978).

Harrison, H.R., et al., "Use of molecular sieves in the methyl esterification of carboxylic acids," *Chem. Ind.* 45:1568, Society of Chemical Industry (1968).

Henecka, H., "Houben-Weyl: Methoden der Organischen Chemie", ed. E. Muller 8:467-469, Thieme, Stuttgart, Germany (1952).

Ito, M., et al., "Synthesis and insectidal activity of Novel N-oxydihydropyrrole derivatives with a substituted spirocyclohexyl group, " *Bioscience, biotechnology, and biochemistry* 67(6):1230-1238, Japan Society for Bioscience, Biotechnology, and Agrochemistry, Japan (2003).

Ketcham, R. et al., "Synthesis of heterocycles. 174 (1,2) sustituted thiazines and bisthiazinyls from dithiooxamide and trichlorophenyl malonates," *J. Heterocycl. Chem* 10:223-228, HeteroCorporation, Utah, United States (1973).

Klingman, G., "5. Surface Active Agents," in Weed Control as a Science: 81-96, John Wiley and Sons, Inc., New York, United States (1961).

Micklefield, J., et al., "Alkylation and acylation of 5-phenylsulphonyl- and 5-cyanobutyrolactones," *Tetrahedron* 48(36):7519-7526, Pergamon Press Ltd, Great Britian (1992).

Munday, L., "Amino-acids of the cyclohexane Series. Part I., " *J. Chem. Soc.*: 4372-4379, Royal Society of Chemistry, Cambridge, United Kingdom (1961).

Nakanishi, S. and Butler, K., "Synthesis of chlorocarbonyl ketenes," *Org. Prep. Proced. Int.* 7(4):155-158, Organic Preparations and Procedures, Inc., United States (1975).

Porter, N., et al., "Preparation of unsymmetrically labeled hydroperoxides. A hydroxamate ester-nitrosation approach," *Journal of Organic Chemistry* 63(16):5547-5554, American Chemical Society, United States (1998).

Schmierer, R. and Mildenberger, H., "Cyclisierung von N-acylalanin- und N-acylglycinestern," *Justus Liebigs Ann. Chem.* 5:1095-1098, Verlag Chemie, Germany (1985).

Sonnewald, U., et al., "Transgenic tobacco plants expressing yeast-derived invertase in either the cytosol, vacuole or apoplast: a powerful tool for studying sucrose metabolism and sink/source interactions," The *Plant Journal* 1(1):95-106, Wiley-Blackwell in association with the Society for Experimental Biology, United Kingdom (1991).

Sonntag, N.O.V., "The reactions of aliphatic acid chlorides", *Chemical Reviews* 52: 237-416, American Chemical Society, United States (1953).

Sousa, A.A., et al., "Esters of 3-hydroxy-2-arylindones, a new class of acaricide," *Journal of Economic Entomology* 66(2):584-586, Entomological Society of America, United Kingdom (1973).

Suzuki S., et al., "Studies on antiviral agents. IV. Biological Activity of Tenuazonic Acid Derivatives", *Chemical & Pharmaceutical Bulletin* 15: 1120-1122, The Pharmaceutical Society of Japan, Japan (1967).

Tsuzuki, K. and Omura, S.,"Synthesis and biological activities of thiotetromycin analogs," *Journal of Antibiotics* 36(00):1589-1591, Japan Antibiotics Research Association, Japan (1983).

Wheeler, T.N., "Novel photochemical synthesis of 2-Aryl-1,3-cyclohexanediones," *Journal of Organic Chemistry* 44(26):4906-4912, American Chemical Society, United Stated (1979).

White, J.D., et al., "Darzens Condensation of α-Halolactones. Glycidic lactones as intermediates in acetogenin synthesis," *Journal of the American Chemical Society* 93(1):281-282, American Chemical Society, United States (1971).

Wolter, F.P., et al., "*rbcS* genes in *Solanum tuberosum*: conservation of transit peptide and exon shuffling during evolution," *Evolution* 5(3):846-850, National Academy of Sciences of the United States of America, United States (1988).

Ziegler, E. and Steiner, E., "Synthesen von heterocyclen, 52. Mitt.: Über Derivate des 2-Phenyl-4-hydroxy-[1,3-thiazinons-(6)]," *Monatshefte für Chemie* 95(1):147-155, Springer Wien, Germany (1964)

Zong, K., et al., "A facile synthesis of [1,2]oxazinane-3,5-diones," *Bull. Korean Chem. Society* 20(8):965-968, Korean Chemical Society, Korea (1999).

http://www.lifesci.sussex.ac.uk/Home/Neil_Crickmore/Bt/ (Sep. 22, 2010).

English language Abstract of European Patent Publication No. EP 0 346 620 A1, European Patent Office, espacenet database—Worldwide (1989).

English language Abstract of European Patent Publication No. EP 0 442 077 A2, European Patent Office, espacenet database—Worldwide (1990).

English language Abstract of German Patent Publication No. DE 10 2005 059 892 A1, European Patent Office, espacenet database—Worldwide (2007).

English language Abstract of Japanese Patent Publication No. JP 60-087254, Japanese Patent Office, Patent & Utility Model Gazette DB, Patent Abstract of Japan (1985).

English language Abstract of Japanese Patent Publication No. JP 11-152273 A, Japanese Patent Office, Patent & Utility Model Gazette DB, Patent Abstract of Japan (1999).

English language Abstract of Japanese Patent Publication No. 2000-53670 A, Japanese Patent Office, Patent & Utility Model Gazette DB, Patent Abstract of Japan (2000).

English language Abstract of Japanese Patent Publication No. JP 14-205984, Japanese Patent Office, Patent & Utility Model Gazette DB, Patent Abstract of Japan (2002).

English language translation of NPL11 (Compagnon, P.L. and Miocque, M., "Addition Des Reactifs Nucleophiles Sur La Triple Liaison Nitrile") (1970).

English language translation of NPL26 (Schmierer, R. and Mildenberger, H., "Cyclisierung von N-acylalanin- und N-acylglycinestern") (1985).

European Search Report of European Application No. EP 09 15 4888, mailed Nov. 13, 2009.

International Search Report of International Application No. PCT/EP2010/001392, published as WO 2010/102758.

Database Registry for 2.5-dichloro-4-(2,2-difluoroethoxy)-benzeneacetic acid, XP-002586767 (2008).

\* cited by examiner

HALOALKYLMETHYLENEOXYPHENYL-SUBSTITUTED KETOENOLS

The present invention relates to novel haloalkylmethyleneoxyphenyl-substituted ketoenols, to several methods for preparation thereof and to the use thereof as pesticides and/or herbicides. The invention also provides selective herbicidal compositions which comprise firstly haloalkylmethyleneoxyphenyl-substituted ketoenols and secondly a compound which improves crop plant compatibility.

The present invention further relates to the enhancement of the action of crop protection compositions comprising especially haloalkylmethyleneoxyphenyl-substituted ketoenols by the addition of ammonium or phosphonium salts and optionally penetration enhancers, to the corresponding compositions, to methods for production thereof and to the use thereof in crop protection as insecticides and/or acaricides and/or for preventing undesired plant growth.

Pharmaceutical properties of 3-acylpyrrolidine-2,4-diones have been described before (S. Suzuki et al. Chem. Pharm. Bull. 15 1120 (1967)). In addition, N-phenylpyrrolidine-2,4-diones have been synthesized by R. Schmierer and H. Mildenberger (Liebigs Ann. Chem. 1985, 1095). Biological efficacy of these compounds has not been described.

EP-A-0 262 399 and GB-A-2 266 888 disclose compounds of similar structure (3-arylpyrrolidine-2,4-diones), which are not, however, known to have any herbicidal, insecticidal or acaricidal action. Known compounds with herbicidal, insecticidal or acaricidal action are unsubstituted, bicyclic 3-arylpyrrolidine-2,4-dione derivatives (EP-A-355 599, EP-A-415 211 and JP-A-12-053 670) and also substituted monocyclic 3-arylpyrrolidine-2,4-dione derivatives (EP-A-377 893 and EP-A-442 077).

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048,545, DEA 102 00505 9892, WO 07/073,856, WO 07/096,058, WO 07/121,868, WO 07/140, 881, WO 08/067,873, WO 08/067,910, WO 08/067,911, WO 08/138,551, WO 09/015,801, WO 09/039,975, WO 09/049, 851, WO 09/115,262, EP application 08170489). Also known are ketal-substituted 1H-arylpyrrolidine-2,4-diones from WO 99/16748, and (spiro)-ketal-substituted N-alkoxyalkoxy-substituted arylpyrrolidinediones from JP-A-14 205 984 and Ito M. et al. Bioscience, Biotechnology and Biochemistry 67, 1230-1238, (2003). The addition of safeners to ketoenols is likewise known in principle from WO 03/013249. Also known from WO 06/024411 are herbicidal compositions comprising ketoenols.

It is known that particular substituted $\Delta^3$-dihydrofuran-2-one derivatives possess herbicidal properties (cf. DE-A-4 014 420). The synthesis of the tetronic acid derivatives used as starting compounds (for example 3-(2-methylphenyl)-4-hydroxy-5-(4-fluorophenyl)-$\Delta^3$-dihydrofuranone-(2)) is likewise described in DE-A-4 014 420. Compounds of similar structure with no report of insecticidal and/or acaricidal efficacy are known from the publication Campbell et al., J. Chem. Soc., Perkin Trans. 1, 1985, (8) 1567-76. 3-Aryl-$\Delta^3$-dihydrofuranone derivatives with herbicidal, acaricidal and insecticidal properties are additionally known from: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 07/048, 545, WO 07/073,856, WO 07/096,058, WO 07/121,868, WO 07/140,881, WO 08/067,911, WO 08/083,950, WO 09/015, 801, WO 09/039,975.

3-Aryl-$\Delta^3$-dihydrothiphenone derivatives are known from WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/013249, WO 04/080 962, WO 04/111 042, WO 05/092897, WO 06/029799 and WO 07/096,058.

Particular phenylpyrone derivatives unsubstituted in the phenyl ring have already become known (cf. A. M. Chirazi, T. Kappe uand E. Ziegler, Arch. Pharm. 309, 558 (1976) and K.-H. Boltze and K. Heidenbluth, Chem. Ber. 91, 2849), though no possible usability as a pesticide is reported for these compounds. Phenylpyrone derivatives substituted in the phenyl ring and having herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972, WO 01/74770, WO 03/013249, WO 04/080 962, WO 04/111 042, WO 05/092897, WO 06/029799 and WO 07/096,058. Additionally described are isomeric pyran-3,5-diones in WO 08/071,405 and WO 09/074,314.

Particular 5-phenyl-1,3-thiazine derivatives unsubstituted in the phenyl ring have already become known (cf. E. Ziegler and E. Steiner, Monatsh. 95, 147 (1964), R. Ketcham, T. Kappe and E. Ziegler, J. Heterocycl. Chem. 10, 223 (1973)), though no possible application as a pesticide is reported for these compounds. 5-Phenyl-1,3-thiazine derivatives substituted in the phenyl ring and having herbicidal, acaricidal and insecticidal action are described in WO 94/14 785, WO 96/2 5395, WO 96/35 664, WO 97/01 535, WO 97/02 243, WO 97/02 243, WO 97/36 868, WO 99/43649, WO 99/48869, WO 99/55673, WO 01/17972, WO 01/74770, WO 03/013249, WO 04/080 962, WO 04/111 042, WO 05/092897, WO 06/029799 and WO 07/096,058.

It is known that particular substituted 2-arylcyclopentanediones possess herbicidal, insecticidal and acaricidal properties (cf., for example, U.S. Pat. Nos. 4,283,348; 4,338, 122; 4,436,666; 4,526,723; 4,551,547; 4,632,698; WO 96/01 798; WO 96/03 366, WO 97/14 667 and WO 98/39281, WO 99/43649, WO99/48869, WO 99/55673, WO 01/17972, WO 01/74770, WO 03/062244, WO 04/080962, WO04/111042, WO05/092897, WO06/029799, WO07/080,066, WO07/096, 058, WO 09/019,005, WO 09/019,015 and EP application 08166352). Also known are similarly substituted compounds; 3-hydroxy-5,5-dimethyl-2-phenylcyclopent-2-en-1-one from the publication Micklefield et al., Tetrahedron, (1992), 7519-26 and the natural substance Involutin, (−)-cis-5-(3,4-dihydroxyphenyl)-3,4-dihydroxy-2-(4-hydroxyphenyl)cyclopent-2-enone from the publication Edwards et al., J. Chem. Soc. S, (1967), 405-9. No insecticidal or acaricidal action is described. Also known is 2-(2,4,6-trimethylphenyl)-1,3-indanedione from the publication J. Economic Entomology, 66, (1973), 584 and the published specification DE-A 2 361 084, with a report of herbicidal and acaricidal effects.

It is known that particular substituted 2-arylcyclohexanediones possess herbicidal, insecticidal and acaricidal properties (U.S. Pat. Nos. 4,175,135, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2,813,341, and Wheeler, T. N., J. Org. Chem. 44, 4906 (1979)), WO 99/43649, WO 99/48869, WO 99/55673, WO 01/17972, WO 01/74770, WO 03/013249, WO 04/080 962, WO 04/111 042, WO 05/092897, WO 06/029799, WO 07/096,058, WO 08/071,405, WO 08/110,307, WO 08/110,308 and WO 08/145,336.

It is known that particular substituted 4-arylpyrazolidine-3,5-diones possess acaricidal, insecticidal and herbicidal properties (cf., for example, WO 92/16510, EP-A-508126, WO 96/11574, WO 96/21 652, WO 99/47525, WO 01/17 351, WO 01/17 352, WO 01/17 353, WO 01/17 972, WO 01/17 973, WO 03/028 466, WO 03/062 244, WO 04/080 962, WO 04/111 042, WO 05/005428, WO 05/016873, WO 05/092897, WO 06/029799 and WO 07/096,058).

It is known that particular tetrahydropyridones possess herbicidal properties (JP 0832530). Also known are specific 4-hydroxytetrahydropyridones with acaricidal, insecticidal and herbicidal properties (JP 11152273). Additionally disclosed have been 4-hydroxytetrahydropyridones as pesticides and herbicides in WO 01/79204 and WO 07/096,058.

It is known that particular 5,6-dihydropyrone derivatives, as protease inhibitors, have antiviral properties (WO 95/14012). Additionally known is 4-phenyl-6-(2-phenethyl)-5,6-dihydropyrone from the synthesis of kavalactone derivatives (Kappe et al., Arch. Pharm. 309, 558-564 (1976)). Also known are 5,6-dihydropyrone derivatives as intermediates (White, J. D., Brenner, J. B., Deinsdale, M. J., J. Amer. Chem. Soc. 93, 281-282 (1971)). 3-Phenyl-5,6-dihydropyrone derivatives with applications in crop protection are described in WO 01/98288 and WO 07/09658.

4-Phenyl-substituted [1,2]-oxazine-3,5-diones were described as herbicides for the first time in WO 01/17972. Additionally described were 4-acyl-substituted [1,2]-oxazine-3,5-diones as pesticides, but in particular as herbicides and growth regulators, for example in EP-A-39 48 89; WO 92/07837, U.S. Pat. No. 5,728,831, and as herbicides and pesticides in WO 03/048138.

The herbicidal and/or acaricidal and/or insecticidal efficacy and/or breadth of action and/or the plant compatibility of the known compounds, especially with respect to crop plants, is, however, not always satisfactory.

Novel compounds of the formula (I) have now been found

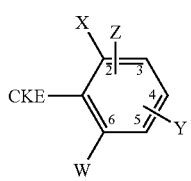
(I)

in which

W is hydrogen, alkyl, halogen, haloalkyl, alkoxy or haloalkoxy,

X is alkyl, alkenyl, alkynyl, halogen, alkoxy, haloalkyl, haloalkoxy or cyano,

Y is hydrogen, alkyl, alkoxy or halogen,

Z is a group

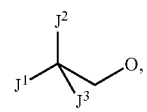

in which $J^1$ and $J^2$ are each independently hydrogen or halogen and $J^3$ is halogen or a haloalkyl group, CKE is one of the groups

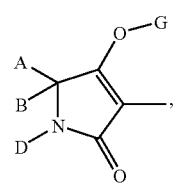
(1)

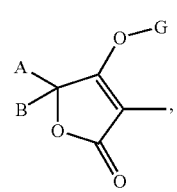
(2)

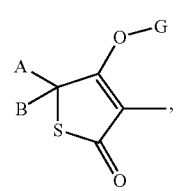
(3)

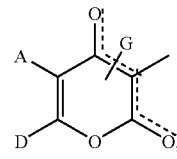
(4)

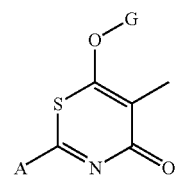
(5)

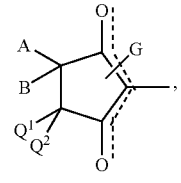
(6)

-continued

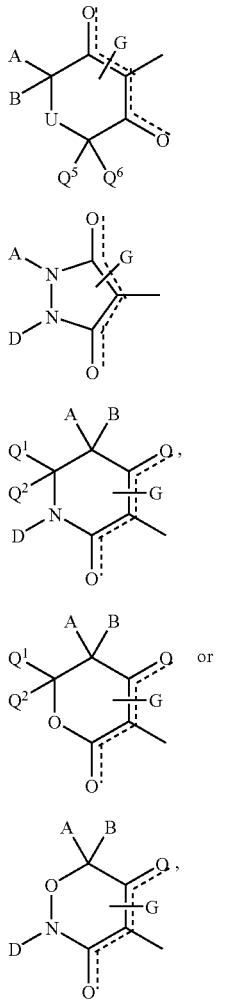

in which

U is —S—, —S(O)—, —S(O)$_2$—, —O—,

an S=N—, S(O)=N— or

group or is optionally Q$^3$- and Q$^4$-substituted C$_1$-C$_4$-alkylene which may optionally be interrupted by oxygen, A is hydrogen, in each case optionally halogen-substituted alkyl, alkenyl, alkoxyalkyl, alkylthioalkyl, or is saturated or unsaturated, optionally substituted cycloalkyl in which at least one ring atom is optionally replaced by a heteroatom, or in each case optionally halogen-, alkyl-, haloalkyl-, alkoxy-, haloalkoxy-, cyano- or nitro-substituted aryl, arylalkyl or hetaryl, B is hydrogen, alkyl or alkoxyalkyl, or A and B together with the carbon atom to which they are bonded are a saturated or unsaturated, unsubstituted or substituted cycle optionally containing at least one heteroatom, D is hydrogen or an optionally substituted radical from the group of alkyl, alkenyl, alkynyl, alkoxyalkyl, saturated or unsaturated cycloalkyl in which one or more ring members are optionally replaced by heteroatoms, or in each case optionally substituted arylalkyl, aryl, hetarylalkyl or hetaryl, or A and D together with the atoms to which they are bonded are a saturated or unsaturated cycle which is unsubstituted or substituted in the A, D moiety and optionally contains at least one (in the case of CKE=8 and 11 one further) heteroatom, or A and Q$^1$ together are in each case optionally substituted alkanediyl or alkenediyl, which may optionally be interrupted by at least one heteroatom, a

or substituted

group or,

B and Q$^2$ together with the atoms to which they are bonded are a saturated or unsaturated cycle which is unsubstituted or substituted in the B, Q$^2$ moiety and optionally contains at least one heteroatom, or D and Q$^1$ together with the atoms to which they are bonded are a saturated or unsaturated cycle which is unsubstituted or substituted in the D, Q$^1$ moiety and optionally contains at least one heteroatom, Q$^1$ is hydrogen, alkyl, alkoxyalkyl, optionally substituted cycloalkyl in which one methylene group is optionally replaced by oxygen or sulphur, or is optionally substituted phenyl, Q$^2$, Q$^4$, Q$^5$ and Q$^6$ are each independently hydrogen or alkyl, Q$^3$ is hydrogen, in each case optionally substituted alkyl, alkoxy, alkylthio, alkoxyalkyl, alkylthioalkyl, or is optionally substituted cycloalkyl in which one or two methylene groups are optionally replaced by oxygen or sulphur, or is optionally substituted phenyl, or Q$^1$ and Q$^2$ together with the carbon atom to which they are bonded are an unsubstituted or substituted cycle optionally containing one heteroatom, or Q$^3$ and Q$^4$ together with the carbon atom to which they are bonded are a saturated or unsaturated, unsubstituted or substituted cycle optionally containing at least one heteroatom, or A and Q$^3$ together with the carbon atom to which they are bonded are a saturated or unsaturated, unsubstituted or substituted cycle optionally containing at least one heteroatom, or A and $Q^5$ together with the carbon atom to which they are bonded are a saturated or unsaturated, unsubstituted or substituted cycle optionally containing at least one heteroatom, G is hydrogen (a) or one of the groups

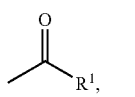
(b)

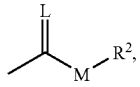
(c)

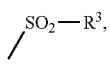
(d)

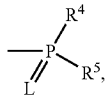
(e)

E or (f)

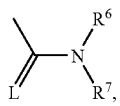
(g)

in which

E is one metal ion equivalent or one ammonium ion,

L is oxygen or sulphur,

M is oxygen or sulphur, $R^1$ is in each case optionally halogen-substituted alkyl, alkenyl, alkoxyalkyl, alkylthioalkyl, polyalkoxyalkyl, or is optionally halogen-alkyl- or alkoxy-substituted cycloalkyl which may be interrupted by at least one heteroatom, or is in each case optionally substituted phenyl, phenylalkyl, hetaryl, phenoxyalkyl or hetaryloxyalkyl, $R^2$ is in each case optionally halogen-substituted alkyl, alkenyl, alkoxyalkyl, polyalkoxyalkyl, or in each case optionally substituted cycloalkyl, phenyl or benzyl, $R^3$, $R^4$ and $R^5$ are each independently in each case optionally halogen-substituted alkyl, alkoxy, alkylamino, dialkylamino, alkylthio, alkenylthio, cycloalkylthio, or in each case optionally substituted phenyl, benzyl, phenoxy or phenylthio, $R^6$ and $R^7$ are each independently hydrogen, in each case optionally halogen-substituted alkyl, cycloalkyl, alkenyl, alkoxy, alkoxyalkyl, optionally substituted phenyl, optionally substituted benzyl, or, together with the nitrogen atom to which they are bonded, a cycle optionally interrupted by oxygen or sulphur.

The compounds of the formula (I) may be present in different composition, also depending on the type of substituents, as geometric and/or optical isomers or isomer mixtures, which can optionally be separated in a customary manner. Both the pure isomers and the isomer mixtures are usable in inventive compositions and their action can be enhanced by inventive ammonium or phosphonium salts. For the sake of simplicity, reference is always made hereinafter to compounds of the formula (I), although this means both the pure compounds and possibly also mixtures with different proportions of isomeric compounds.

Taking account of the meanings (1) to (11) of the CKE group, the following principal structures (I-1) to (I-11) arise:

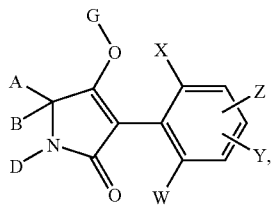
(I-1)

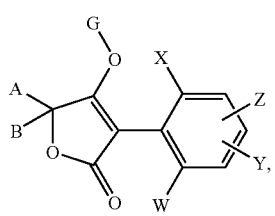
(I-2)

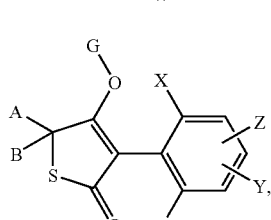
(I-3)

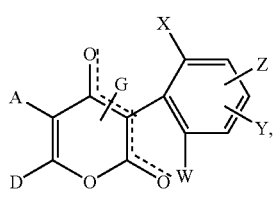
(I-4)

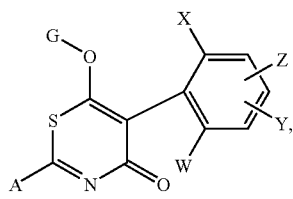
(I-5)

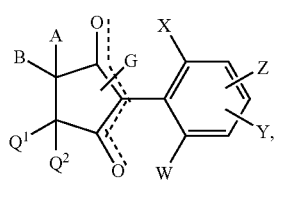
(I-6)

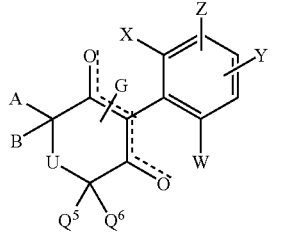
(I-7)

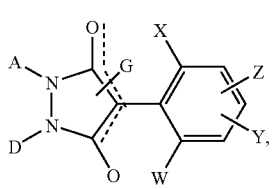 (I-8)
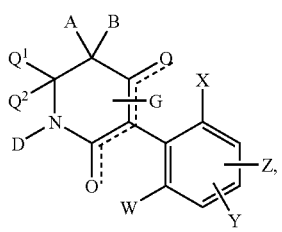 (I-9)
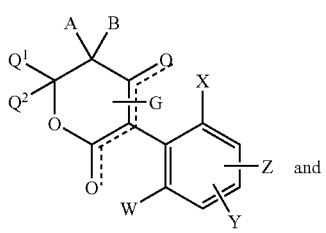 (I-10) and
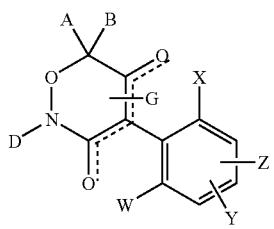 (I-11)
in which
A, B, D, G, $Q^1$, $Q^2$, $Q^5$, $Q^6$, U, W, X, Y and Z are each as defined above.
Taking account of the different meanings (a), (b), (c), (d), (e), (f) and (g) of the G group, the following principal structures (I-1-a) to (I-1-g), arise when CKE is the group (1),
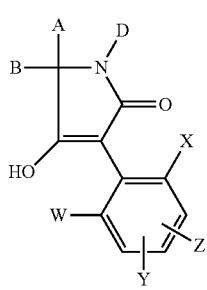 (I-1-a)
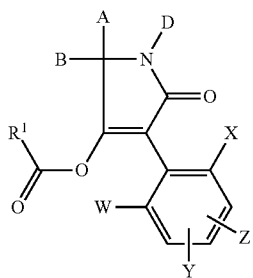 (I-1-b)
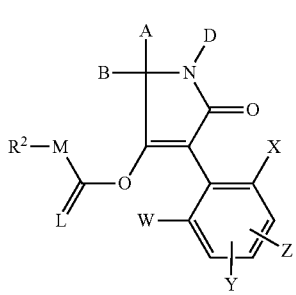 (I-1-c)
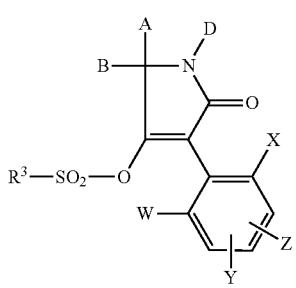 (I-1-d)
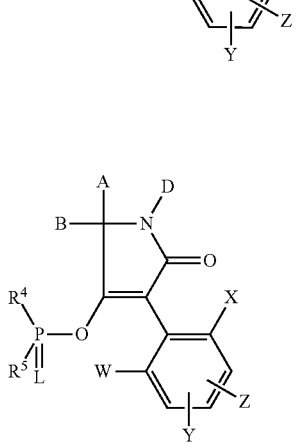 (I-1-e)
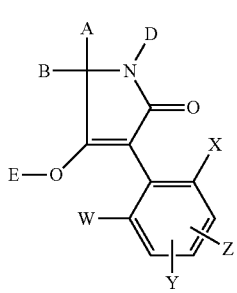 (I-1-f)

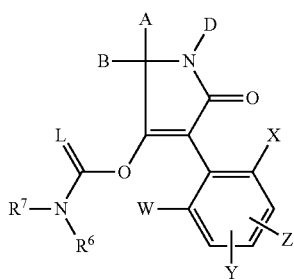
(I-1-g)

in which

A, B, D, E, L, M, W, X, Y, Z, $R^1$, $R^2$, $R^3$, $R^4$, $R^5$, $R^6$ and $R^7$ are each as defined above.

Taking account of the different meanings (a), (b), (c), (d), (e), (f) and (g) of the G group, the following principal structures (I-2-a) to (I-2-g), arise when CKE is the group (2),

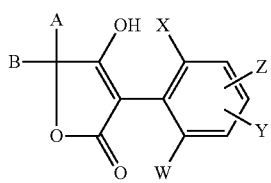
(I-2-a)

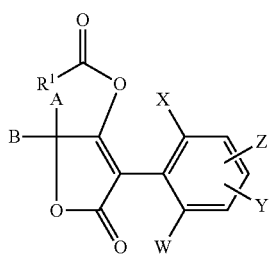
(I-2-b)

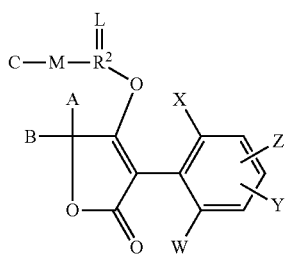
(I-2-c)

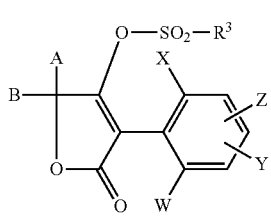
(I-2-d)

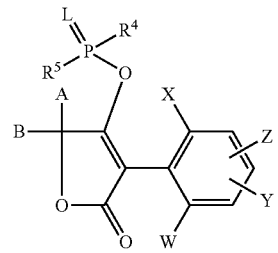
(I-2-e)

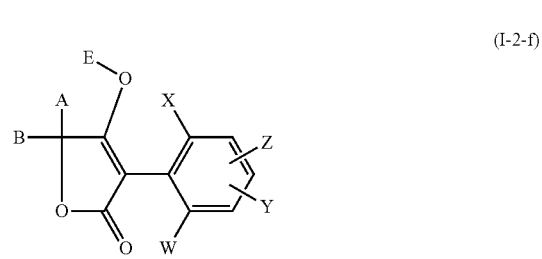
(I-2-f)

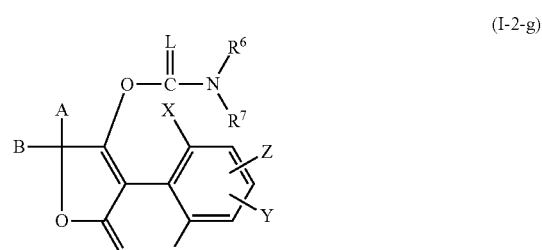
(I-2-g)

in which

A, B, E, L, M, W, X, Y, Z, $R^1$, $R^2$, $R^3$, $R^4$, $R^5$, $R^6$ and $R^7$ are each as defined above.

Taking account of the different meanings (a), (b), (c), (d), (e), (f) and (g) of the G group, the following principal structures (I-3-a) to (I-3-g), arise when CKE is the group (3),

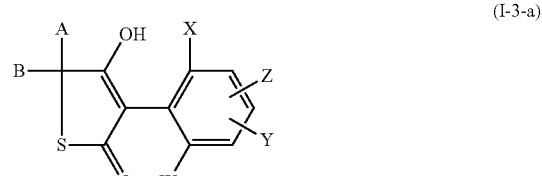
(I-3-a)

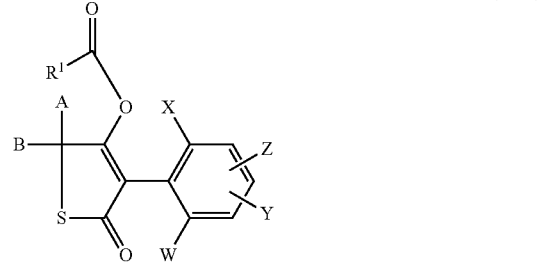
(I-3-b)

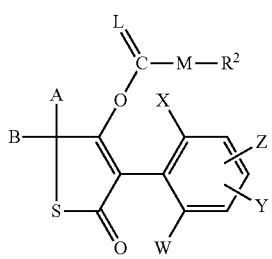 (I-3-c)

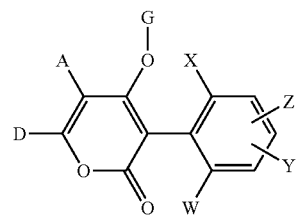 (I-4-A)

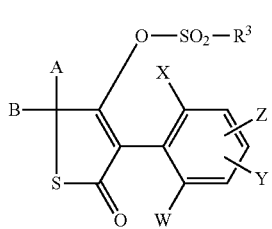 (I-3-d)

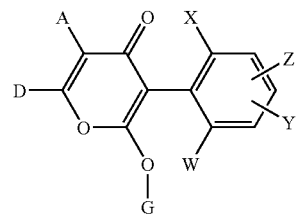 (I-4-B)

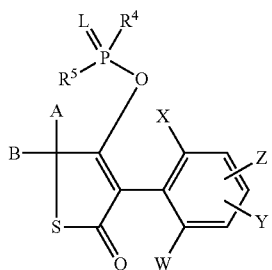 (I-3-e)

which is expressed by the broken line in the formula (I-4).

The compounds of the formulae (I-4-A) and (I-4-B) may be present either as mixtures or in the form of pure isomers thereof. Mixtures of the compounds of the formulae (I-4-A) and (I-4-B) can optionally be separated in a manner known per se by physical methods, for example by chromatographic methods.

For reasons of better clarity, only one of the possible isomers in each case is shown hereinafter. This does not rule out the possibility that the compounds may be present in the form of the isomer mixtures or in the other isomeric form in each case.

Taking account of the different meanings (a), (b), (c), (d), (e), (f) and (g) of the G group, the following principal structures (I-4-a) to (I-4-g), arise when CKE is the group (4), (I-3-f)

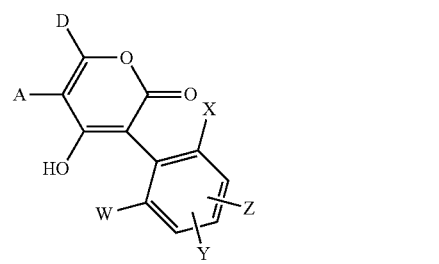 (I-4-a)

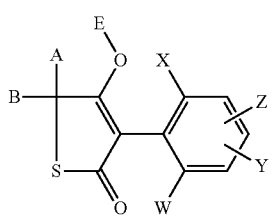 (I-3-g)

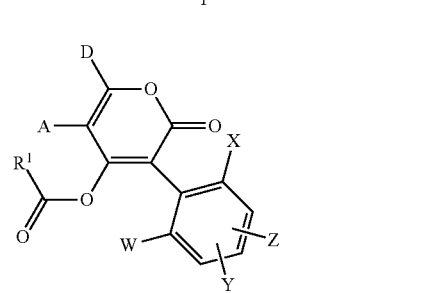 (I-4-b)

in which
A, B, E, L, M, W, X, Y, Z, $R^1$, $R^2$, $R^3$, $R^4$, $R^5$, $R^6$ and $R^7$ are each as defined above.

Depending on the position of the substituent G, the compounds of the formula (I-4) may be present in the two isomeric forms of the formulae (I-4-A) and (I-4-B),

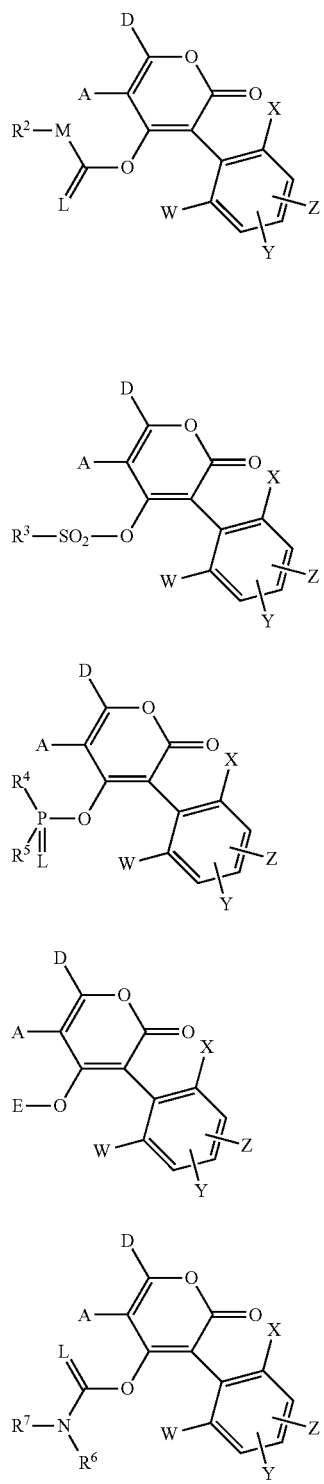
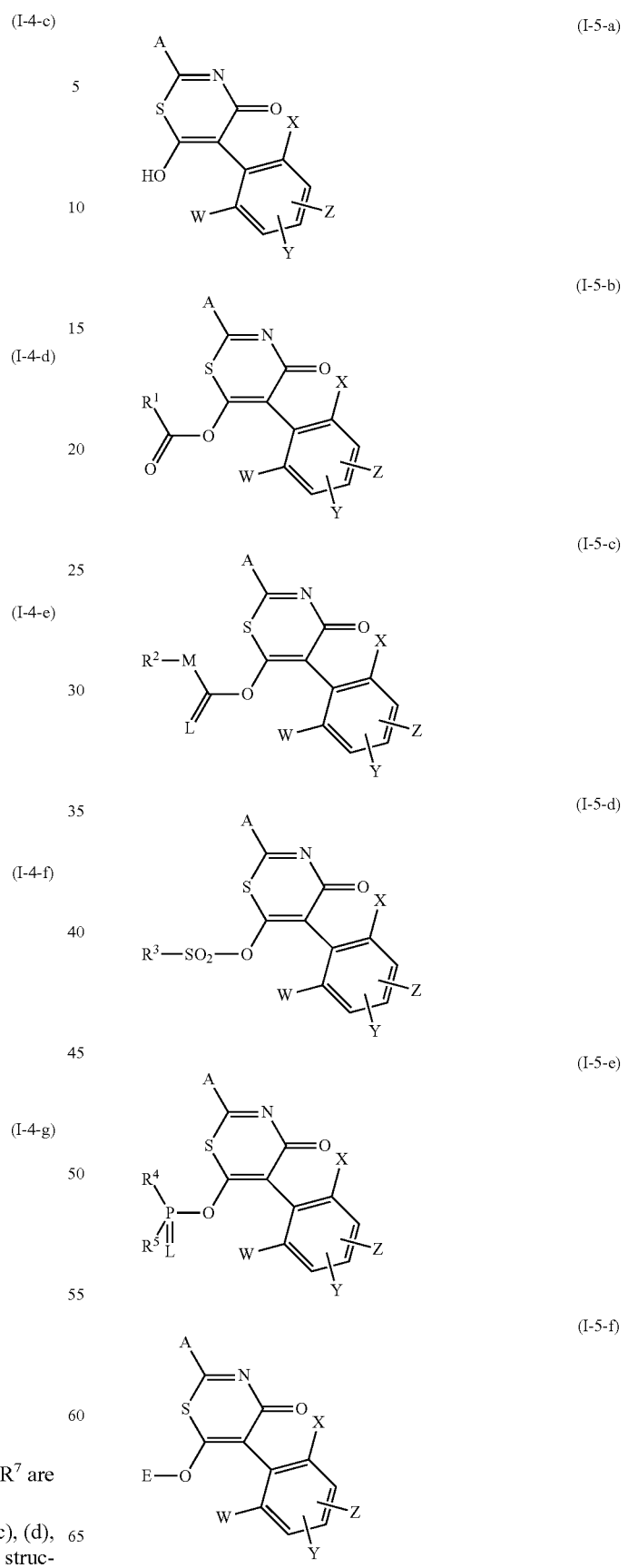
in which
A, D, E, L, M, W, X, Y, Z, $R^1$, $R^2$, $R^3$, $R^4$, $R^5$, $R^6$ and $R^7$ are each as defined above.
Taking account of the different meanings (a), (b), (c), (d), (e), (f) and (g) of the G group, the following principal structures (I-5-a) to (I-5-g), arise when CKE is the group (5), -continued (I-5-g)

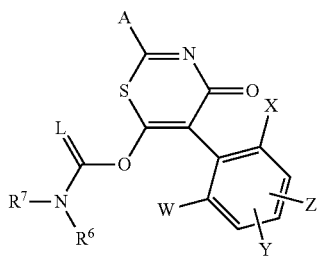

in which
A, E, L, M, W, X, Y, Z, $R^1$, $R^2$, $R^3$, $R^4$, $R^5$, $R^6$ and $R^7$ are each as defined above.

Depending on the position of the substituent G, the compounds of the formula (I-6) may be present in the two isomeric forms of the formulae (I-6-A) and (I-6-B), (I-6-A)

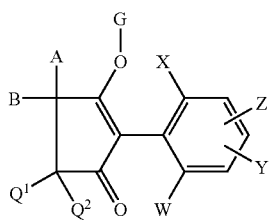

(I-6-B)

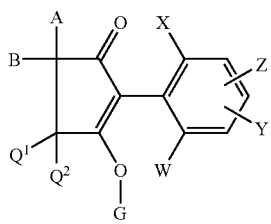

which is expressed by the broken line in the formula (I-6).

The compounds of the formulae (I-6-A) and (I-6-B) may be present either as mixtures or in the form of pure isomers thereof. Mixtures of the compounds of the formulae (I-6-A) and (I-6-B) can optionally be separated by physical methods, for example by chromatographic methods.

For reasons of better clarity, only one of the possible isomers in each case is shown hereinafter.

This does not rule out the possibility that the compounds may be present in the form of the isomer mixtures or in the other isomeric form in each case.

Taking account of the different meanings (a), (b), (c), (d), (e), (f) and (g) of the G group, the following principal structures (I-6-a) to (I-6-g), arise when CKE is the group (6), (I-6-a)

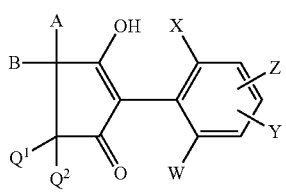

(I-6-b)

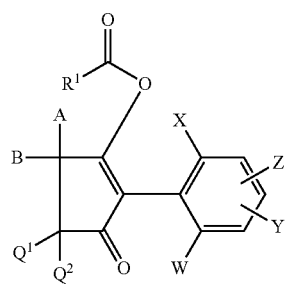

(I-6-c)

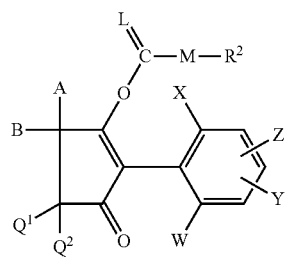

(I-6-d)

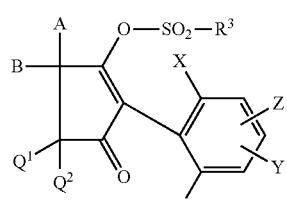

(I-6-e)

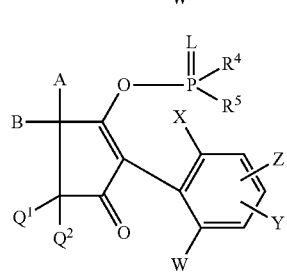

(I-6-f)

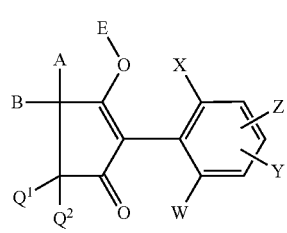

(I-6-g)

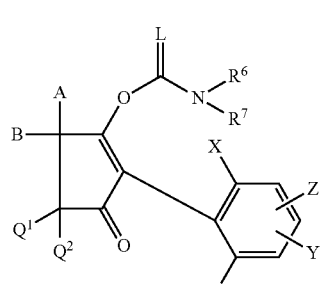

in which
A, B, $Q^1$, $Q^2$, E, L, M, W, X, Y, Z, $R^1$, $R^2$, $R^3$, $R^4$, $R^5$, $R^6$ and $R^7$ are each as defined above.

Depending on the position of the substituent G, the compounds of the formula (I-7) may be present in the two isomeric forms of the formulae (I-7-A) and (I-7-B), which is expressed by the broken line in the formula (I-7):

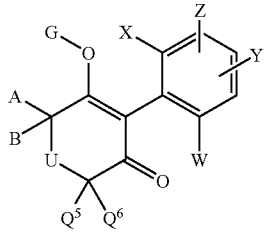
(I-7-A)

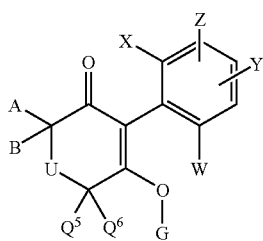
(I-7-B)

The compounds of the formulae (I-7-A) and (I-7-B) may be present either as mixtures or in the form of pure isomers thereof. Mixtures of the compounds of the formulae (I-7-A) and (I-7-B) can optionally be separated by physical methods, for example by chromatographic methods.

For reasons of better clarity, only one of the possible isomers in each case is shown hereinafter. This does not rule out the possibility that the compound may be present in the form of the isomer mixtures or in the other isomeric form in each case.

Taking account of the different meanings (a), (b), (c), (d), (e), (f) and (g) of the G group, the following principal structures (I-7-a) to (I-7-g), arise when CKE is the group (7),

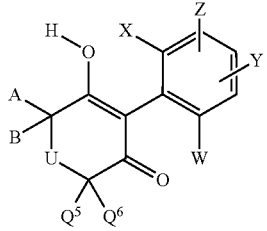
(I-7-a)

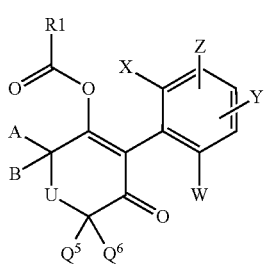
(I-7-b)

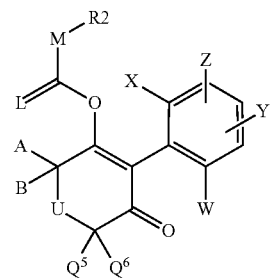
(I-7-c)

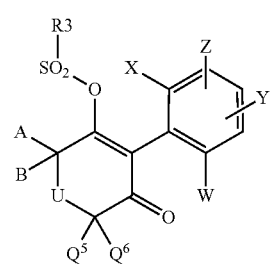
(I-7-d)

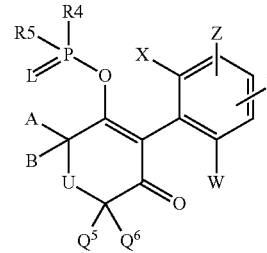
(I-7-e)

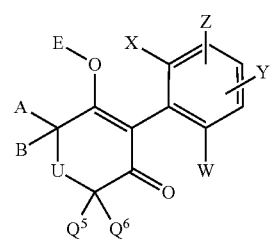
(I-7-f)

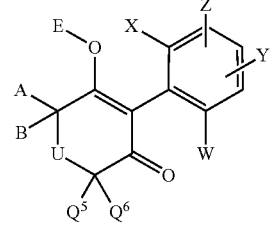
(I-7-g)

in which
A, B, E, L, M, $Q^5$, $Q^6$, U, W, X, Y, Z, $R^1$, $R^2$, $R^3$, $R^4$, $R^5$, $R^6$ and $R^7$ are each as defined above.

Depending on the position of the substituent G, the compounds of the formula (I-8) may be present in the two isomeric forms (I-8-A) and (I-8-B), (I-8-A)

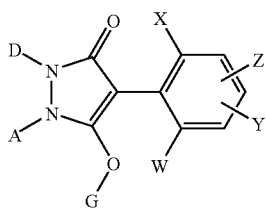

(I-8-B)

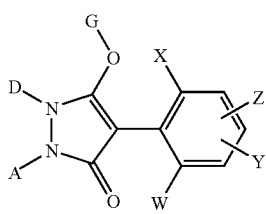

which is expressed by the broken line in the formula (I-8).

The compounds of the formulae (I-8-A) and (I-8-B) may be present either as mixtures or in the form of pure isomers thereof. Mixtures of the compounds of the formulae (I-8-A) and (I-8-B) can optionally be separated in a manner known per se by physical methods, for example by chromatographic methods.

For reasons of better clarity, only one of the possible isomers in each case is shown hereinafter. This does not rule out the possibility that the compounds may be present in the form of the isomer mixtures or in the other isomeric form in each case.

Taking account of the different meanings (a), (b), (c), (d), (e), (f) and (g) of the G group, the following principal structures (I-8-a) to (I-8-g), arise when CKE is the group (8), (I-8-a)

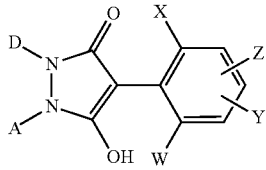

(I-8-b)

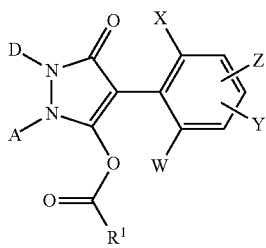

(I-8-c)

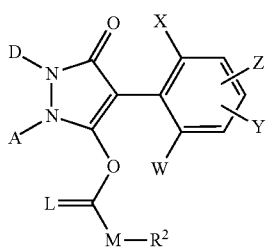

(I-8-d)

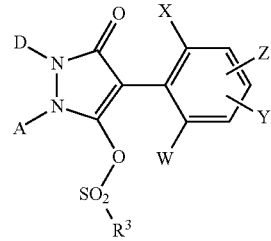

(I-8-e)

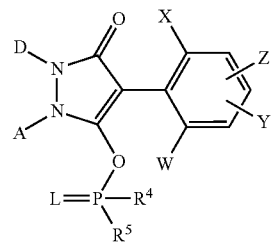

(I-8-f)

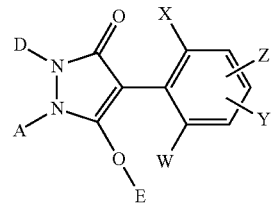

(I-8-g)

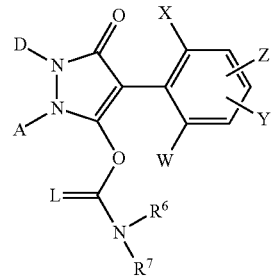

in which

A, D, E, L, M, W, X, Y, Z, $R^1$, $R^2$, $R^3$, $R^4$, $R^5$, $R^6$ and $R^7$ are each as defined above.

Depending on the position of the substituent G, the compounds of the formula (I-9) may be present in the two isomeric forms of the formulae (I-9-A) and (I-9-B), which is expressed by the broken line in the formula (I-9):

(I-9-A)

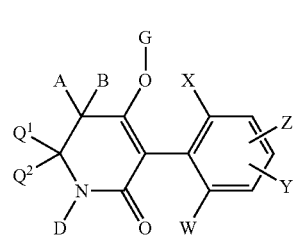

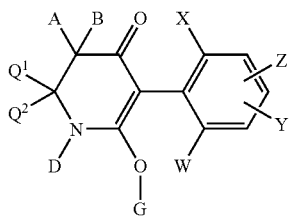
(I-9-B)

The compounds of the formulae (I-9-A) and (I-9-B) may be present either as mixtures or in the form of pure isomers thereof. Mixtures of the compounds of the formulae (I-9-A) and (I-9-B) can optionally be separated in a manner known per se by physical methods, for example by chromatographic methods.

For reasons of better clarity, only one of the possible isomers in each case is shown hereinafter. This does not rule out the possibility that the compounds may be present in the form of the isomer mixtures or in the other isomeric form in each case.

Taking account of the different meanings (a), (b), (c), (d), (e), (f) and (g) of the G group, the following principal structures (I-9-a) to (I-9-g), arise when CKE is the group (9),

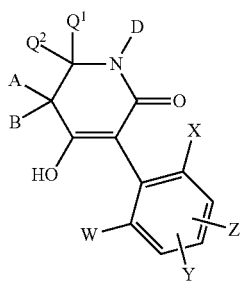
(I-9-a)

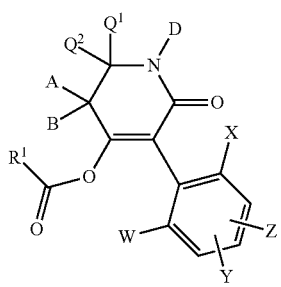
(I-9-b)

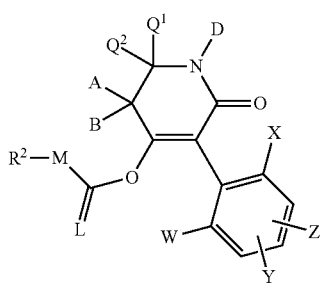
(I-9-c)

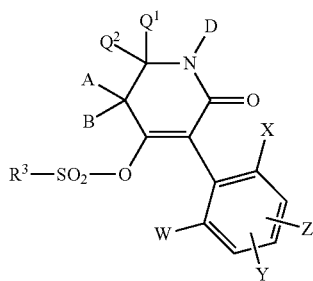
(I-9-d)

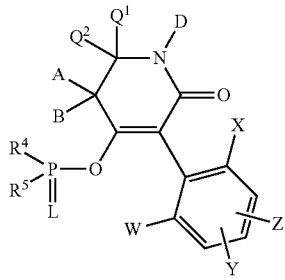
(I-9-e)

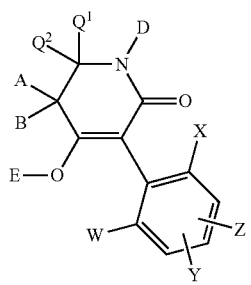
(I-9-f)

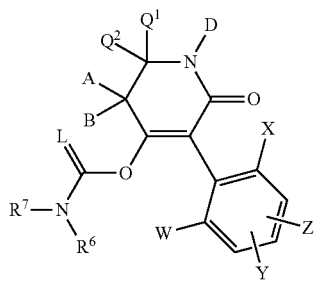
(I-9-g)

in which

A, B, D, E, L, M, $Q^1$, $Q^2$, W, X, Y, Z, $R^1$, $R^2$, $R^3$, $R^4$, $R^5$, $R^6$ and $R^7$ are each as defined above.

Depending on the position of the substituent G, the compounds of the formula (I-10) may be present in the two isomeric forms of the formulae (I-10-A) and (I-10-B),

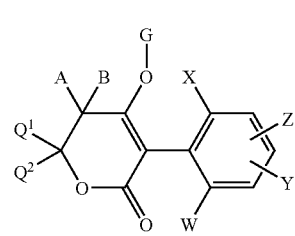
(I-10-A)

-continued (I-10-B)
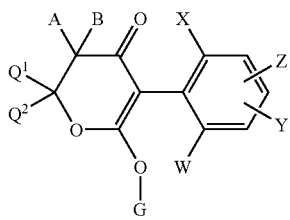

which is expressed by the broken line in the formula (I-10).

The compounds of the formulae (I-10-A) and (I-10-B) may be present either as mixtures or in the form of pure isomers thereof. Mixtures of the compounds of the formulae (I-10-A) and (I-10-B) can optionally be separated in a manner known per se by physical methods, for example by chromatographic methods.

For reasons of better clarity, only one of the possible isomers in each case is shown hereinafter. This does not rule out the possibility that the compounds may be present in the form of the isomer mixtures or in the other isomeric form in each case.

Taking account of the different meanings (a), (b), (c), (d), (e), (f) and (g) of the G group, the following principal structures (I-10-a) to (I-10-g), arise when CKE is the group (10), (I-10-a)
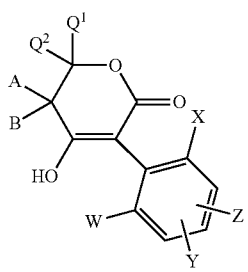

(I-10-b)
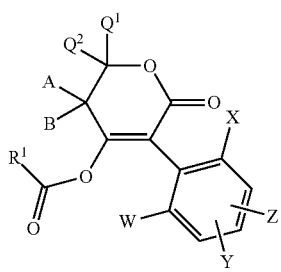

(I-10-c)
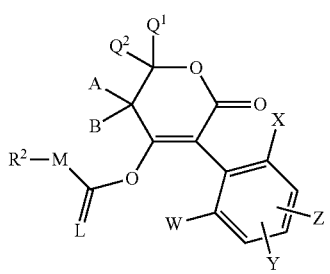

-continued (I-10-d)
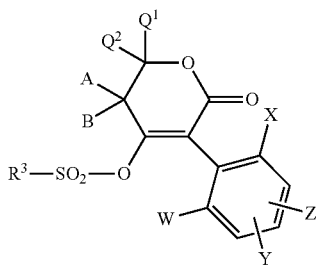

(I-10-e)
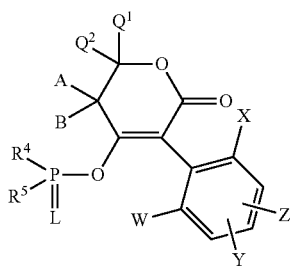

(I-10-f)
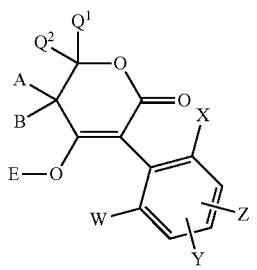

(I-10-g)
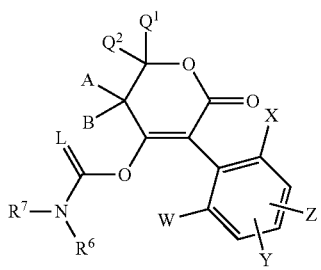

in which

A, B, E, L, M, $Q^1$, $Q^2$, W, X, Y, Z, $R^1$, $R^2$, $R^3$, $R^4$, $R^5$, $R^6$ and $R^7$ are each as defined above.

Depending on the position of the substituent G, the compounds of the formula (I-11) may be present in the two isomeric forms of the formulae (I-11-A) and (I-11-B), which is expressed by the broken line in the formula (I-11).

(I-11-A)
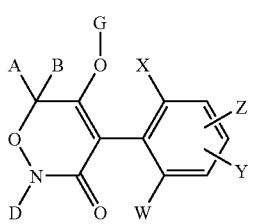

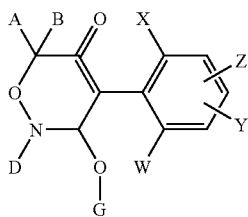

(I-11-B)

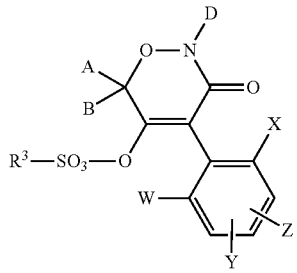

(I-11-d)

The compounds of the formulae (I-11-A) and (I-11-B) may be present either as mixtures or in the form of pure isomers thereof. Mixtures of the compounds of the formulae (I-11-A) and (I-11-B) can optionally be separated in a manner known per se by physical methods, for example by chromatographic methods.

For reasons of better clarity, only one of the possible isomers in each case is shown hereinafter. This does not rule out the possibility that the compounds may be present in the form of the isomer mixtures or in the other isomeric form in each case.

Taking account of the different meanings (a), (b), (c), (d), (e), (f) and (g) of the G group, the following principal structures (I-11-a) to (I-11-g), arise when CKE is the group (11),

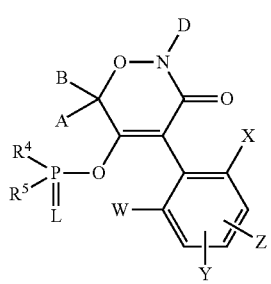

(I-11-e)

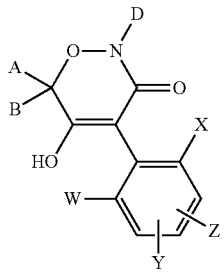

(I-11-a)

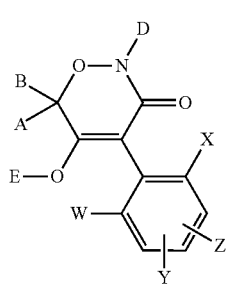

(I-11-f)

(I-11-b)

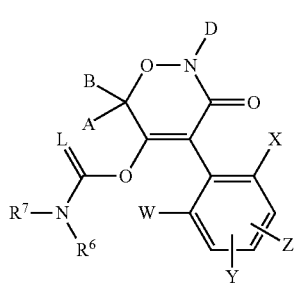

(I-11-g)

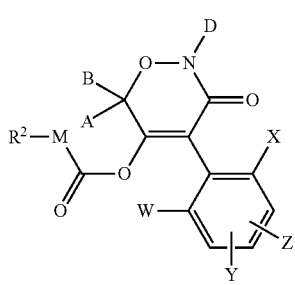

(I-11-c)

in which

A, B, D, E, L, M, W, X, Y, Z, $R^1$, $R^2$, $R^3$, $R^4$, $R^5$, $R^6$ and $R^7$ are each as defined above.

It has additionally been found that the novel compounds of the formula (I) are obtained by one of the processes described hereinafter:

(A) Substituted 3-phenylpyrrolidine-2,4-diones or enols thereof, of the formula (I-1-a)

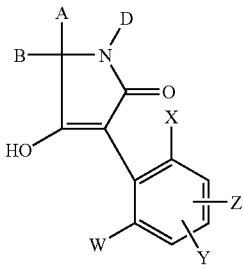

(I-1-a)

in which
A, B, D, W, X, Y and Z are each as defined above,
are obtained when
N-acylamino acid esters of the formula (II)

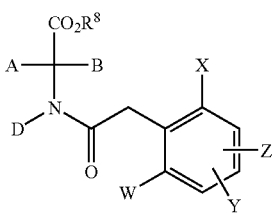

(II)

in which

A, B, D, W, X, Y and Z are each as defined above,
and
$R^8$ is alkyl (preferably $C_1$-$C_6$-alkyl),
are intramolecularly condensed in the presence of a diluent and in the presence of a base.

(B) It has also been found that substituted 3-phenyl-4-hydroxy-$\Delta^3$-dihydrofuranone derivatives of the formula (I-2-a)

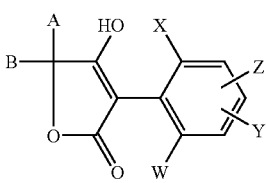

(I-2-a)

in which
A, B, W, X, Y and Z are each as defined above,
are obtained when
carboxylic esters of the formula (III)

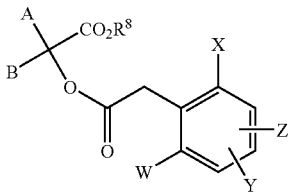

(III)

in which
A, B, W, X, Y, Z and $R^8$ are each as defined above,
are intramolecularly condensed in the presence of a diluent and in the presence of a base.

(C) It has additionally been found that substituted 3-phenyl-4-hydroxy-$\Delta^3$-dihydrothiophenone derivatives of the formula (I-3-a)

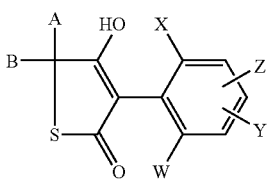

(I-3-a)

in which
A, B, W, X, Y and Z are each as defined above,
are obtained when
β-ketocarboxylic esters of the formula (IV)

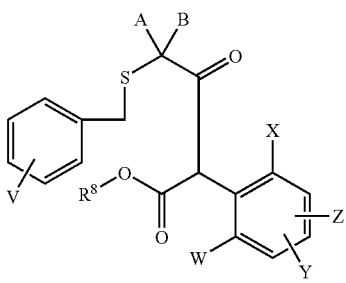

(IV)

in which
A, B, W, X, Y, Z and $R^8$ are each as defined above and
V is hydrogen, halogen, alkyl (preferably $C_1$-$C_6$-alkyl) or alkoxy (preferably $C_1$-$C_8$-alkoxy),
are intramolecularly cyclized, optionally in the presence of a diluent and in the presence of an acid.

(D) It has additionally been found that the novel substituted 3-phenylpyrone derivatives of the formula (I-4-a)

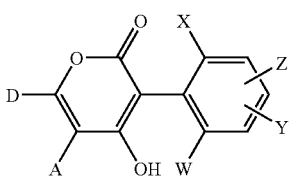

(I-4-a)

in which
A, D, W, X, Y and Z are each as defined above,
are obtained when
carbonyl compounds of the formula (V)

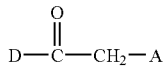
(V)

in which
A and D are each as defined above,
or the silyl enol ethers thereof, of the formula (Va)

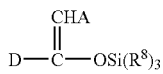
(Va)

in which
A, D and $R^8$ are each as defined above,
are reacted with ketenoyl halides of the formula (VI)

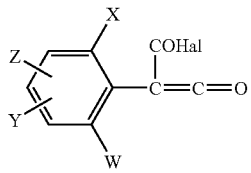
(VI)

in which
W, X, Y and Z are each as defined above and
Hal is halogen (preferably chlorine or bromine),
optionally in the presence of a diluent and optionally in the presence of an acid acceptor.

It has additionally been found,
(E) that the novel substituted phenyl-1,3-thiazine derivatives of the formula (I-5-a)

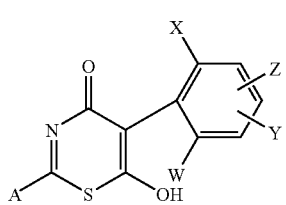
(I-5-a)

in which
A, W, X, Y and Z are each as defined above,
are obtained when thioamides of the formula (VII)

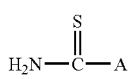
(VII)

in which
A is as defined above,
are reacted with ketenoyl halides of the formula (VI)

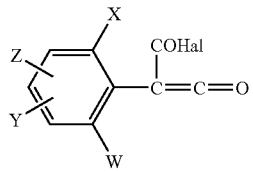
(VI)

in which
Hal, W, X, Y and Z are each as defined above,
optionally in the presence of a diluent and optionally in the presence of an acid acceptor.

It has additionally been found,
(F) that compounds of the formula (I-6-a)

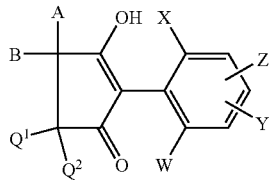
(I-6-a)

in which
A, B, $Q^1$, $Q^2$, W, X, Y and Z are each as defined above,
are obtained when
ketocarboxylic esters of the formula (VIII)

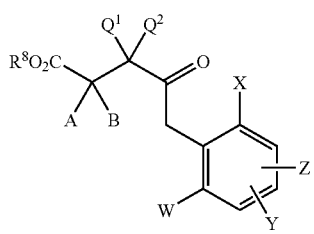
(VIII)

in which
A, B, $Q^1$, $Q^2$, W, X, Y and Z are each as defined above, and
$R^8$ is alkyl (especially $C_1$-$C_8$-alkyl), are intramolecularly cyclized, optionally in the presence of a diluent and in the presence of a base.

It has also been found
(G) that compounds of the formula (I-7-a)

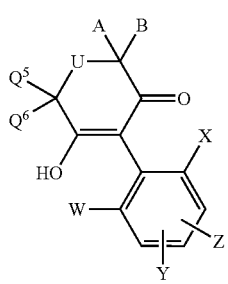
(I-7-a)

in which

A, B, $Q^5$, $Q^6$, U, W, X, Y and Z are each as defined above, are obtained when 6-aryl-5-ketohexanoic esters of the formula (IX)

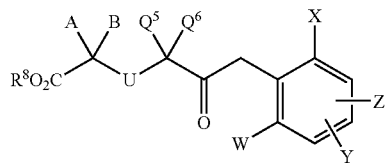
(IX)

in which

A, B, $Q^5$, $Q^6$, U, W, X, Y and Z are each as defined above and $R^8$ is alkyl (preferably $C_1$-$C_6$-alkyl), are intramolecularly condensed in the presence of a diluent and in the presence of a base.

(H) It has additionally been found that the compounds of the formula (I-8-a)

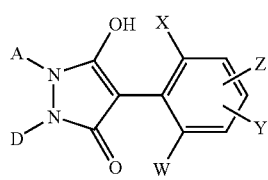
(I-8-a)

in which

A, D, W, X, Y and Z are each as defined above, are obtained when compounds of the formula (X)

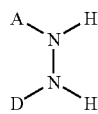
(X)

in which

A and D are each as defined above,

α) are reacted with compounds of the formula (VI)

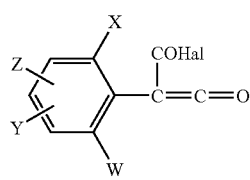
(VI)

in which

Hal, W, X, Y and Z are each as defined above, optionally in the presence of a diluent and optionally in the presence of an acid acceptor, or β) are reacted with compounds of the formula (XI)

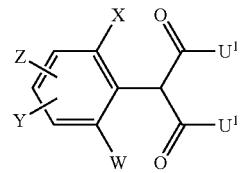
(XI)

in which

W, X, Y and Z are each as defined above, and $U^1$ is $NH_2$ or O—$R^8$ where $R^8$ is as defined above, optionally in the presence of a diluent and optionally in the presence of a base, or γ) are reacted with compounds of the formula (XII)

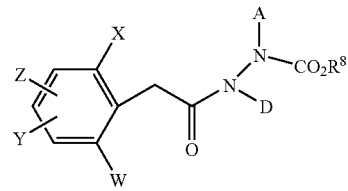
(XII)

in which

A, D, W, X, Y, Z and $R^8$ are each as defined above, optionally in the presence of a diluent and optionally in the presence of a base.

It has also been found that the novel compounds of the formula (I-9-a) are obtained by one of the methods described hereinafter:

(I) Substituted tetrahydropyridine-2,4-diones or the enols thereof, of the formula (I-9-a)

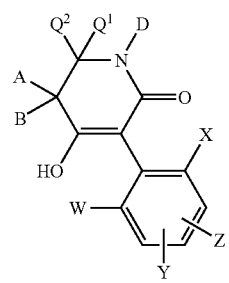
(I-9-a)

in which

A, B, D, $Q^1$, $Q^2$, W, X, Y and Z are each as defined above, are obtained when N-acylamino acid esters of the formula (XIII)

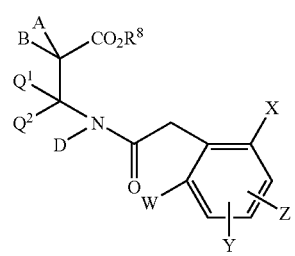
(XIII)

in which
A, B, D, $Q^2$, W, X, Y and Z are each as defined above,
and
$R^8$ is alkyl (preferably $C_1$-$C_6$-alkyl),
are intramolecularly condensed in the presence of a diluent and in the presence of a base.

It has additionally been found that
(J) substituted 5,6-dihydropyrones of the formula (I-10-a)

(I-10-a)

in which
A, B, $Q^1$, $Q^2$, W, X, Y and Z are each as defined above,
are obtained when
O-acylhydroxycarboxylic esters of the formula (XIV)

(XIV)

in which
A, B, $Q^1$, $Q^2$, W, X, Y and Z are each as defined above,
and
$R^8$ is alkyl (preferably $C_1$-$C_6$-alkyl),
are converted, optionally in the presence of a diluent and optionally in the presence of a base.

It has additionally been found that the novel compounds of the formula (I-11-a) are obtained by one of the processes described hereinafter:
(K) Substituted oxazine-3,5-diones or the enols thereof, of the formula (I-11-a)

(I-11-a)

in which
A, B, D, W, X, Y and Z are each as defined above,
are obtained when
N-acylamino acid esters of the formula (XV)

(XV)

in which
A, B, D, W, X, Y and Z are each as defined above,
and
$R^8$ is alkyl (preferably $C_1$-$C_6$-alkyl),
are intramolecularly condensed in the presence of a diluent and in the presence of a base.

It has also been found
(L) that the compounds of the formulae (I-1-b) to (I-11-b) shown above, in which A, B, D, $Q^1$, $Q^2$, $Q^5$, $Q^6$, $R^1$, U, W, X, Y and Z are each as defined above are obtained when compounds of the formulae (I-1-a) to (I-11-a) shown above, in which A, B, D, $Q^1$, $Q^2$, $Q^5$, $Q^6$, U, W, X, Y and Z are each as defined above, are reacted in each case
(α) with acid halides of the formula (XVI)

(XVI)

in which
$R^1$ is as defined above and
Hal is halogen (especially chlorine or bromine)
or
(β) with carboxylic anhydrides of the formula (XVII)

$$R^1—CO—O—CO—R^1 \quad \text{(XVII)}$$

in which
$R^1$ is as defined above,
optionally in the presence of a diluent and optionally in the presence of an acid binder;
(M) that the compounds of the formulae (I-1-c) to (I-11-c) shown above, in which A, B, D, $Q^1$, $Q^2$, $Q^5$, $Q^6$, $R^2$, M, U, W, X, Y and Z are each as defined above and L is oxygen, are obtained when compounds of the formulae (I-1-a) to (I-11-a) shown above, in which A, B, D, $Q^1$, $Q^2$, $Q^5$, $Q^6$, U, W, X, Y and Z are each as defined above, are reacted in each case
with chloroformic esters or chloroformic thio esters of the formula (XVIII)

$$R^2\text{-M-CO—Cl} \quad \text{(XVIII)}$$

in which
$R^2$ and M are each as defined above,
optionally in the presence of a diluent and optionally in the presence of an acid binder;
(N) that compounds of the formulae (I-1-c) to (I-11-c) shown above, in which A, B, D, $Q^1$, $Q^2$, $Q^5$, $Q^6$, $R^2$, M, U, W, X, Y and Z are each as defined above and L is sulphur are obtained when compounds of the formulae (I-1-a) to (I-11- a) shown above, in which A, B, D, $Q^1$, $Q^2$, $Q^5$, $Q^6$, U, U, W, X, Y and Z are each as defined above are reacted in each case with chloromonothioformic esters or chlorodithioformic esters of the formula (XIX)

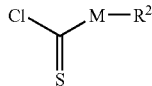
(XIX)

in which

M and $R^2$ are each as defined above, optionally in the presence of a diluent and optionally in the presence of an acid binder, and (O) that compounds of the formulae (I-1-d) to (I-11-d) shown above, in which A, B, D, $Q^1$, $Q^2$, $Q^5$, $Q^6$, $R^3$, U, W, X, Y and Z are each as defined above, are obtained when compounds of the formulae (I-1-a) to (I-11-a) shown above, in which A, B, D, $Q^1$, $Q^2$, $Q^5$, $Q^6$, U, W, X, Y and Z are each as defined above, are reacted in each case with sulphonyl chlorides of the formula (XX)

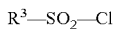
(XX)

in which $R^3$ is as defined above, optionally in the presence of a diluent and optionally in the presence of an acid binder, (P) that compounds of the formulae (I-1-e) to (I-11-e) shown above, in which A, B, D, L, $Q^1$, $Q^2$, $Q^5$, $Q^6$, $R^4$, $R^5$, U, W, X, Y and Z are each as defined above, are obtained when compounds of the formulae (I-1-a) to (I-11-a) shown above, in which A, B, D, $Q^1$, $Q^2$, $Q^5$, $Q^6$, U, W, X, Y and Z are each as defined above, are reacted in each case with phosphorus compounds of the formula (XXI)

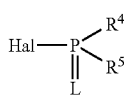
(XXI)

in which

L, $R^4$ and $R^5$ are each as defined above and

Hal is halogen (especially chlorine or bromine), optionally in the presence of a diluent and optionally in the presence of an acid binder, (Q) that compounds of the formulae (I-1-f) to (I-11-f) shown above, in which A, B, D, E, $Q^1$, $Q^2$, $Q^5$, $Q^6$, U, W, X, Y and Z are each as defined above, are obtained when compounds of the formulae (I-1-a) to (I-11-a), in which A, B, D, $Q^1$, $Q^2$, $Q^5$, $Q^6$, U, W, X, Y and Z are each as defined above, are reacted in each case with metal compounds or amines of the formulae (XXII) and (XXIII))

(XXII)

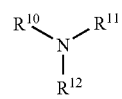
(XXIII)

in which

Me is a mono- or divalent metal (preferably an alkali metal or alkaline earth metal such as lithium, sodium, potassium, magnesium or calcium), or an ammonium ion

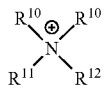

t is the number 1 or 2 and $R^{10}$, $R^{11}$, $R^{12}$ are each independently hydrogen or alkyl (preferably $C_1$-$C_8$-alkyl), optionally in the presence of a diluent, (R) that compounds of the formulae (I-1-g) to (I-11-g) shown above, in which A, B, D, L, $Q^1$, $Q^2$, $Q^5$, $Q^6$, $R^6$, $R^7$, U, W, X, Y and Z are each as defined above, are obtained when compounds of the formulae (I-1-a) to (I-11-a) shown above, in which A, B, D, $Q^1$, $Q^2$, $Q^5$, $Q^6$, U, W, X, Y and Z are each as defined above, in each case (α) are reacted with isocyanates or isothiocyanates of the formula (XXIV)

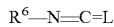
(XXIV)

in which $R^6$ and L are each as defined above, optionally in the presence of a diluent and optionally in the presence of a catalyst, or (β) are reacted with carbamyl chlorides or thiocarbamyl chlorides of the formula (XXV)

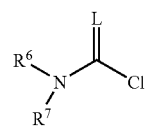
(XXV)

in which

L, $R^6$ and $R^7$ are each as defined above, optionally in the presence of a diluent and optionally in the presence of an acid binder, (S) that compounds of the formulae (I-1-a) to (I-11-g) shown above, in which A, B, D, G, $Q^1$, $Q^2$, $Q^5$, $Q^6$, U, W, X, Y and Z' are each as defined above, are obtained when the bromine or iodine atom in compounds of the formulae (I-1') to (I-11'), in which A, B, D, G, $Q^1$, $Q^2$, $Q^5$, $Q^6$, U, W, X and Y are each as defined above and Z' is preferably bromine or iodine

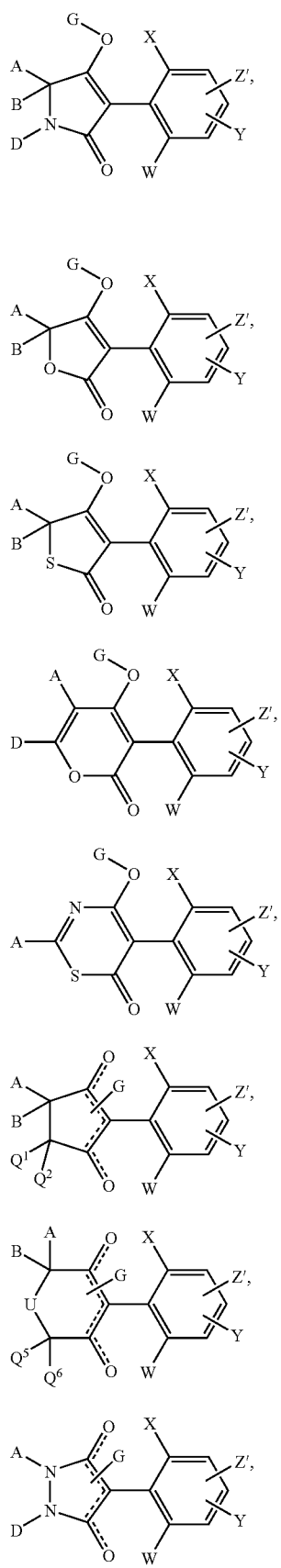

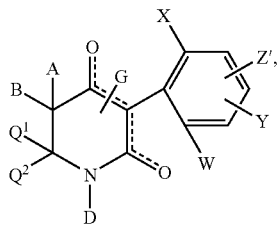

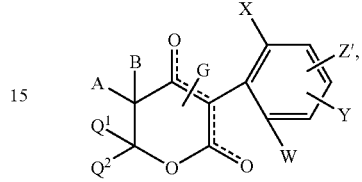

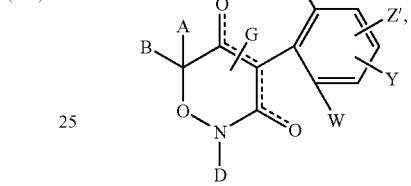

is exchanged with halogenated alcohols, for example trifluoroethanol of the formula (XXVI)

$$Z—OH \quad (XXVI)$$

in the presence of a solvent, in the presence of a copper salt (e.g. Cu(I)I) and in the presence of a base (for example potassium tert-butoxide, sodium hydride).

It has additionally been found that the novel compounds of the formula (I) have very good efficacy as pesticides, preferably as insecticides, acaricides and/or herbicides.

It has now also been found that, surprisingly, particular haloalkylmethyleneoxyphenyl-substituted ketoenols, when applied together with the compounds which improve crop plant compatibility described hereinafter (safeners/antidotes), prevent damage to the crop plants extremely efficiently and can be used particularly advantageously as broadly active combination preparations for selective control of undesired plants in useful plant crops, for example in cereals, but also maize, rape, soya and rice.

The invention also provides selective herbicidal compositions comprising an effective content of an active ingredient combination, comprising, as components, a') at least one compound of the formula (I) in which CKE, W, X, Y and Z are each as defined above
and (b') at least one compound which improves crop plant compatibility (safener).

The safeners are preferably selected from the group consisting of:

S1) compounds of the formula (S1)

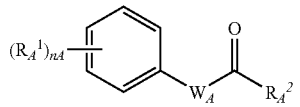

where the symbols and indices are each defined as follows:

$n_A$ is a natural number from 0 to 5, preferably from 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group of partially unsaturated or aromatic five-membered heterocycles having 1 to 3 hetero ring atoms from the group of N and O, where at least one nitrogen atom and at most one oxygen atom is present in the ring, preferably a radical from the group of $(W_A^1)$ to $(W_A^4)$,

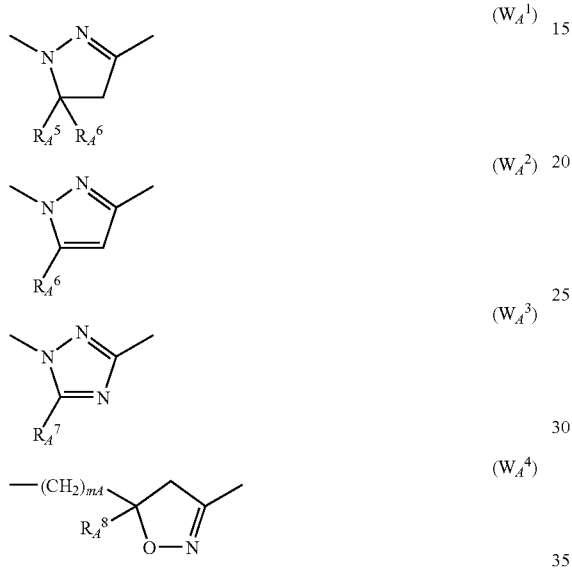

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is attached via the nitrogen atom to the carbonyl group in (S1) and which is unsubstituted or substituted by radicals from the group of $(C_1-C_4)$-alkyl, $(C_1-C_4)$-alkoxy and optionally substituted phenyl, preferably a radical of the formula $OR_A^3$, $NHR_A^4$ or $N(CH_3)_2$, in particular of the formula $OR_A^3$;

$R_A^3$ is hydrogen or an unsubstituted or substituted aliphatic hydrocarbon radical, preferably having a total of 1 to 18 carbon atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxy-carbonyl)-5-methyl-2-pyrazoline-3-carboxylate (S1-1) ("mefenpyr(-diethyl)"), and related compounds, as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;

c) derivatives of 1,5-diphenylpyrazole-3-carboxylic acid (S1'), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

d) compounds of the triazolecarboxylic acid type (S1$^d$), preferably compounds such as fenchlorazole(-ethyl), i.e. ethyl 1-(2,4-dichlorophenyl)-5-trichloro-methyl-(1H)-1,2,4-triazole-3-carboxylate (S1-7), and related compounds, as described in EP-A-174 562 and EP-A-346 620;

e) compounds of the 5-benzyl- or 5-phenyl-2-isoxazoline-3-carboxylic acid or the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

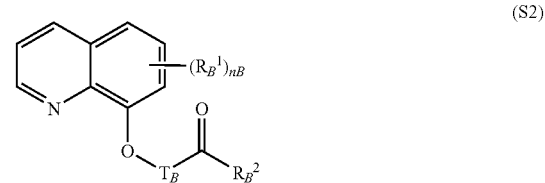

where the symbols and indices are each defined as follows:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably from 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is attached via the nitrogen atom to the carbonyl group in (S2) and which is unsubstituted or substituted by radicals from the group of $(C_1-C_4)$-alkyl, $(C_1-C_4)$-alkoxy and optionally substituted phenyl, preferably a radical of the formula $OR_B^3$, $NHR_B^4$ or $N(CH_3)_2$, in particular of the formula $OR_B^3$;

$R_B^3$ is hydrogen or an unsubstituted or substituted aliphatic hydrocarbon radical, preferably having a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$- or $C_2)$-alkanediyl chain which is unsubstituted or substituted by one or two $(C_1-C_4)$-alkyl radicals or by $[(C_1-C_3)$-alkoxy]carbonyl;

preferably:
a) compounds of the 8-quinolinoxyacetic acid type (S2$^a$), preferably 1-methylhexyl (5-chloro-8-quinolinoxy)acetate ("cloquintocet-mexyl" (S2-1), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxo-prop-1-yl (5-chloro-8-quinolinoxy) acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminium, iron, ammonium, quaternary ammonium, sulphonium or phosphonium salts, as described in WO-A-2002/34048;
b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

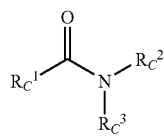

(S3)

where the symbols and indices are each defined as follows:
$R_C^1$ is $(C_1$-$C_4)$-alkyl, $(C_1$-$C_4)$-haloalkyl, $(C_2$-$C_4)$-alkenyl, $(C_2$-$C_4)$-haloalkenyl, $(C_3$-$C_7)$-cycloalkyl, preferably dichloromethyl;
$R_C^2$, $R_C^3$ are identical or different and are hydrogen, $(C_1$-$C_4)$-alkyl, $(C_2$-$C_4)$-alkenyl, $(C_2$-$C_4)$-alkynyl, $(C_1$-$C_4)$-haloalkyl, $(C_2$-$C_4)$-haloalkenyl, $(C_1$-$C_4)$-alkylcarbamoyl-$(C_1$-$C_4)$-alkyl, $(C_2$-$C_4)$-alkenylcarbamoyl-$(C_1$-$C_4)$-alkyl, $(C_1$-$C_4)$-alkoxy-$(C_1$-$C_4)$-alkyl, dioxolanyl-$(C_1$-$C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;
preferably:
  active ingredients of the dichloroacetamide type which are frequently used as pre-emergence safeners (soil-acting safeners), such as, for example,
  "dichlormid" (N,N-diallyl-2,2-dichloroacetamide) (S3-1),
  "R-29148" (3-dichloroacetyl-2,2,5-trimethyl-1,3-oxazolidine) from Stauffer (S3-2),
  "R-28725" (3-dichloroacetyl-2,2-dimethyl-1,3-oxazolidine) from Stauffer (S3-3),
  "benoxacor" (4-dichloroacetyl-3,4-dihydro-3-methyl-2H-1,4-benzoxazine) (S3-4),
  "PPG-1292" (N-allyl-N-[(1,3-dioxolan-2-yl)methyl]dichloroacetamide) from PPG Industries (S3-5),
  "DKA-24" (N-allyl-N-[(allylaminocarbonyl)methyl]dichloroacetamide) from Sagro-Chem (S3-6),
  "AD-67" or "MON 4660" (3-dichloroacetyl-1-oxa-3-azaspiro[4,5]decane) from Nitrokemia or Monsanto (S3-7),
  "TI-35" (1-dichloroacetylazepane) from TRI-Chemical RT (S3-8)
  "diclonon" (dicyclonon) or "BAS145138" or "LAB145138" (S3-9) (3-dichloroacetyl-2,5,5-trimethyl-1,3-diazabicyclo[4.3.0]nonane) from BASF,
  "furilazole" or "MON 13900" ORS)-3-dichloroacetyl-5-(2-furyl)-2,2-dimethyloxazolidine) (S3-10) and also its (R)-isomer (S3-11).

S4) N-Acylsulphonamides of the formula (S4) and salts thereof

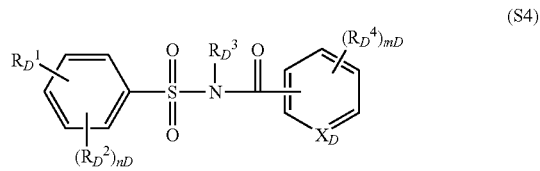

(S4)

where the symbols and indices are each defined as follows:
$X_D$ is CH or N;
$R_D^1$ is CO—$NR_D^5R_D^6$ or NHCO—$R_D^7$;
$R_D^2$ is halogen, $(C_1$-$C_4)$-haloalkyl, $(C_1$-$C_4)$-haloalkoxy, nitro, $(C_1$-$C_4)$-alkyl, $(C_1$-$C_4)$-alkoxy, $(C_1$-$C_4)$-alkylsulphonyl, $(C_1$-$C_4)$-alkoxycarbonyl or $(C_1$-$C_4)$-alkylcarbonyl;
$R_D^3$ is hydrogen, $(C_1$-$C_4)$-alkyl, $(C_2$-$C_4)$-alkenyl or $(C_2$-$C_4)$-alkynyl;
$R_D^4$ is halogen, nitro, $(C_1$-$C_4)$-alkyl, $(C_1$-$C_4)$-haloalkyl, $(C_1$-$C_4)$-haloalkoxy, $(C_3$-$C_6)$-cycloalkyl, phenyl, $(C_1$-$C_4)$-alkoxy, cyano, $(C_1$-$C_4)$-alkylthio, $(C_1$-$C_4)$-alkylsulphinyl, $(C_1$-$C_4)$-alkylsulphonyl, $(C_1$-$C_4)$-alkoxycarbonyl or $(C_1$-$C_4)$-alkylcarbonyl;
$R_D^5$ is hydrogen, $(C_1$-$C_6)$-alkyl, $(C_3$-$C_6)$-cycloalkyl, $(C_2$-$C_6)$-alkenyl, $(C_2$-$C_6)$-alkynyl, $(C_5$-$C_6)$-cycloalkenyl, phenyl or 3- to 6-membered heterocyclyl which contains $v_D$ heteroatoms from the group of nitrogen, oxygen and sulphur, where the last seven radicals are substituted by $v_D$ substituents from the group of halogen, $(C_1$-$C_6)$-alkoxy, $(C_1$-$C_6)$-haloalkoxy, $(C_1$-$C_2)$-alkylsulphinyl, $(C_1$-$C_2)$-alkylsulphonyl, $(C_3$-$C_6)$-cycloalkyl, $(C_1$-$C_4)$-alkoxycarbonyl, $(C_1$-$C_4)$-alkylcarbonyl and phenyl and, in the case of cyclic radicals, also $(C_1$-$C_4)$-alkyl and $(C_1$-$C_4)$-haloalkyl;
$R_D^6$ is hydrogen, $(C_1$-$C_6)$-alkyl, $(C_2$-$C_6)$-alkenyl or $(C_2$-$C_6)$-alkynyl, where the last three radicals are substituted by $v_D$ radicals from the group of halogen, hydroxy, $(C_1$-$C_4)$-alkyl, $(C_1$-$C_4)$-alkoxy and $(C_1$-$C_4)$-alkylthio, or
$R_D^5$ and $R_D^6$ together with the nitrogen atom bearing them form a pyrrolidinyl or piperidinyl radical;
$R_D^7$ is hydrogen, $(C_1$-$C_4)$-alkylamino, di-$(C_1$-$C_4)$-alkylamino, $(C_1$-$C_6)$-alkyl, $(C_3$-$C_6)$-cycloalkyl, where the last 2 radicals are substituted by $v_D$ substituents from the group of halogen, $(C_1$-$C_4)$-alkoxy, halo-$(C_1$-$C_6)$-alkoxy and $(C_1$-$C_4)$-alkylthio and, in the case of cyclic radicals, also $(C_1$-$C_4)$-alkyl and $(C_1$-$C_4)$-haloalkyl;
$n_D$ is 0, 1 or 2;
$m_D$ is 1 or 2;
$v_D$ is 0, 1, 2 or 3;

among these, preference is given to compounds of the N-acylsulphonamide type, for example of the formula (S4$^a$) below, which are known, for example, from WO-A-97/45016

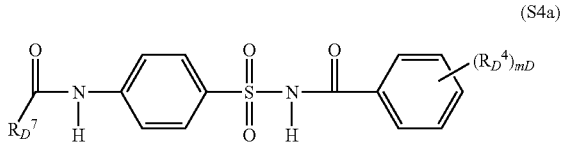

(S4a)

in which
$R_D^7$ is $(C_1-C_6)$-alkyl, $(C_3-C_6)$-cycloalkyl, where the 2 last-mentioned radicals are substituted by $v_D$ substituents from the group of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
$R_D^4$ is halogen, $(C_1-C_4)$-alkyl, $(C_1-C_4)$-alkoxy, $CF_3$,
$m_D$ is 1 or 2;
$v_D$ is 0, 1, 2 or 3;
and also
acylsulphamoylbenzamides, for example of the formula (S4$^b$) below, which are known, for example, from WO-A-99/16744,

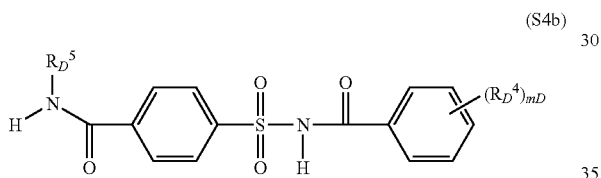

(S4b)

for example those in which
$R_D5$=cyclopropyl and $(R_D^4)$=2-OMe ("cyprosulfamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)
and also
compounds of the N-acylsulphamoylphenylurea type of the formula (S4$^c$), which are known, for example, from EP-A-365484,

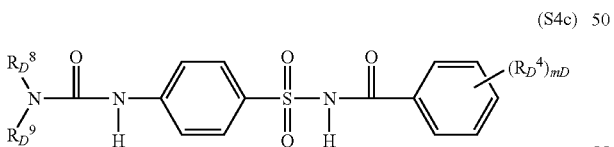

(S4c)

in which
$R_D^8$ and $R_D^9$ are each independently hydrogen, $(C_1-C_8)$-alkyl, $(C_3-C_8)$-cycloalkyl, $(C_3-C_6)$-alkenyl, $(C_3-C_6)$-alkynyl,
$R_D^4$ is halogen, $(C_1-C_4)$-alkyl, $(C_1-C_4)$-alkoxy, $CF_3$,
$m_D$ is 1 or 2;
for example
1-[4-(N-2-methoxybenzoylsulphamoyl)phenyl]-3-methylurea,
1-[4-(N-2-methoxybenzoylsulphamoyl)phenyl]-3,3-dimethyl urea,
1-[4-(N-4,5-dimethylbenzoylsulphamoyl)phenyl]-3-methylurea.

S5) Active ingredients from the class of the hydroxyaromatics and aromatic-aliphatic carboxylic acid derivatives (S5), for example
ethyl 3,4,5-triacetoxybenzoate, 3,5-dimethoxy-4-hydroxybenzoic acid, 3,5-dihydroxybenzoic acid, 4-hydroxysalicyclic acid, 4-fluorosalicyclic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active ingredients from the class of the 1,2-dihydroquinoxalin-2-ones (S6), for example
1-methyl-3-(2-thienyl)-1,2-dihydroquinoxalin-2-one,
1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2 (1H)-one, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856,

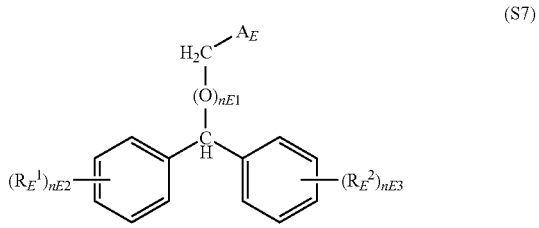

(S7)

where the symbols and indices are each defined as follows:
$R_E^1$, $R_E^2$ are each independently halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
$A_E$ is $COOR_E^3$ or $COSR_E^4$
$R_E^3$, $R_E^4$ are each independently hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium,
$n_E$ is 0 or 1
$n_E^2$, $n_E^3$ are each independently 0, 1 or 2,
preferably:
diphenylmethoxyacetic acid,
ethyl diphenylmethoxyacetate,
methyl diphenylmethoxyacetate (CAS Reg. No.: 41858-19-9) (S7-1).

S8) Compounds of the formula (S8), as described in WO-A-98/27049,

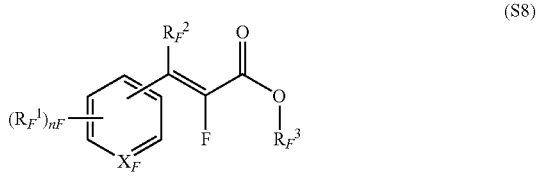

(S8)

in which $X_F$ is CH or N, $n_F$ is, if $X_F=N$, an integer from 0 to 4 and is, if $X_F=CH$, an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, $(C_1-C_4)$-alkoxycarbonyl, optionally substituted phenyl, optionally substituted phenoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof, preferably compounds in which $X_F$ is CH, $n_F$ is an integer from 0 to 2, $R_F^1$ is halogen, $(C_1-C_4)$-alkyl, $(C_1-C_4)$-haloalkyl, $(C_1-C_4)$-alkoxy, $(C_1-C_4)$-haloalkoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof, S9) Active ingredients from the class of the 3-(5-tetrazolyl-carbonyl)-2-quinolones (S9), for example 1,2-dihydro-4-hydroxy-1-ethyl-3-(5-tetrazolylcarbo-nyl)-2-quinolone (CAS Reg. No.: 219479-18-2), 1,2-dihydro-4-hydroxy-1-methyl-3-(5-tetrazolylcarbo-nyl)-2-quinolone (CAS Reg. No.: 95855-00-8), as described in WO-A-1999/000020.

S10) Compounds of the formula (S10$^a$) or (S10$^b$) as described in WO-A-2007/023719 and WO-A-2007/023764

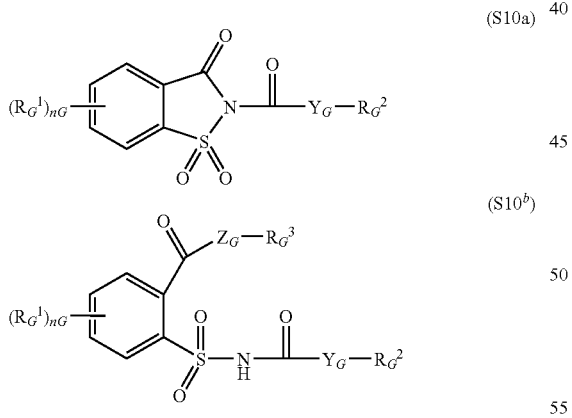

in which $R_G^1$ is halogen, $(C_1-C_4)$-alkyl, methoxy, nitro, cyano, $CF_3$, $OCF_3$ $Y_G$, $Z_G$ are each independently O or S, $n_G$ is an integer from 0 to 4, $R_G^2$ is $(C_1-C_{16})$-alkyl, $(C_2-C_6)$-alkenyl, $(C_3-C_6)$-cycloalkyl, aryl; benzyl, halobenzyl, $R_G^3$ is hydrogen or $(C_1-C_6)$-alkyl.

S11) Active ingredients of the oxyimino compound type (S11), which are known as seed dressings, such as, for example, "oxabetrinil" ((Z)-1,3-dioxolan-2-ylmethoxyimino (phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and "cyometrinil" or "CGA-43089" ((Z)-cyanomethoxy-imino(phenyl)acetonitrile) (S11-3), which is known as seed dressing safener for millet against metolachlor damage.

S12) Active ingredients from the class of the isothiochro-manones (S12), such as, for example, methyl [(3-oxo-1H-2-benzothiopyran-4(3H)-ylidene)methoxy]acetate (CAS Reg. No.: 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as seed dressing safener for corn against thiocarbamate herbicide damage, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as seed dressing safener for millet against alachlor and metolachlor damage, "CL-304415" (CAS Reg. No.: 31541-57-8) (4-carboxy-3,4-dihydro-2H-1-benzopyran-4-acetic acid) (S13-4) from American Cyanamid, which is known as a safener for corn against imidazolinone damage, "MG-191" (CAS Reg. No.: 96420-72-3) (2-dichlorom-ethyl-2-methyl-1,3-dioxolane) (513-5) from Nitroke-mia, which is known as a safener for corn, "MG-838" (CAS Reg. No.: 133993-74-5) (2-propenyl 1-oxa-4-azaspiro[4.5]decane-4-car-bodithioate) (S13-6) from Nitrokemia, "disulfoton" (O,O-diethyl S-2-ethylthioethyl phospho-rodithioate) (S13-7), "dietholate" (O,O-diethyl O-phenyl phosphorothioate) (S13-8), "mephenate" (4-chlorophenyl methylcarbamate) (S13-9).

S14) Active ingredients which, in addition to a herbicidal effect against harmful plants, also have a safener effect on crop plants such as rice, such as, for example, "dimepiperate" or "MY-93" (S-1-methyl-1-phenylethyl piperidine-1-carbothioate), which is known as a safener for rice against molinate herbicide damage, "daimuron" or "SK 23" (1-(1-methyl-1-phenylethyl)-3-p-tolylurea), which is known as a safener for rice against imazosulphuron herbicide damage, "cumyluron"="JC-940" (3-(2-chlorophenylmethyl)-1-(1-methyl-1-phenylethyl)-urea, see JP-A-60087254), which is known as a safener for rice against some herbicide damage, "methoxyphenone" or "NK 049" (3,3'-dimethyl-4-methoxybenzophenone), which is known as a safener for rice against some herbicide damage, "CSB" (1-bromo-4-(chloromethylsulphonyl)benzene) from Kumiai, (CAS Reg. No. 54091-06-4), which is known as a safener against some herbicide damage in rice.

S15) Active ingredients which are primarily used as herbicides, but also have safener effect on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

The most preferred compounds [components (b')] which improve crop plant compatibility are cloquintocet-mexyl, fenchlorazol ethyl ester, isoxadifen-ethyl, mefenpyr-diethyl, fenclorim, cumyluron, S4-1 and S4-5, particular emphasis being given to mefenpyr-diethyl. Cyprosulfamide (S4-1) is likewise emphasized.

It has now been found that, surprisingly, the above-defined active ingredient combinations of compounds of the general formula (I) and safeners (antidotes) from group (b') listed above, coupled with very good useful plant compatibility, have a particularly high herbicidal efficacy and can be used in different crops, especially in cereals (in particular wheat), but also in soya, potatoes, maize and rice, for selective weed control.

In this context, it is considered to be surprising that, from a multitude of known safeners or antidotes which are capable of antagonizing the damaging effect of a herbicide on the crop plants, specifically the compounds of group (b') listed above are suitable for virtually completely eliminating the damaging effect of compounds of the formula (I) on the crop plants, without significantly impairing the herbicidal efficacy toward the weeds.

Emphasis is given here to the particularly advantageous effect of the particularly preferred and most preferred combination partners from group (b'), especially with regard to protection of cereal plants, for example wheat, barley and rye, but also maize and rice, as crop plants.

The inventive compounds are defined in general terms by the formula (I). Preferred substituents and ranges of the radicals shown in the formulae mentioned above and hereinafter are detailed as follows:

W is preferably hydrogen, $C_1$-$C_6$-alkyl, halogen, $C_1$-$C_6$-alkoxy, $C_1$-$C_4$-haloalkyl or $C_1$-$C_4$-haloalkoxy, X is preferably halogen, $C_1$-$C_6$-alkyl, $C_2$-$C_6$-alkenyl, $C_2$-$C_6$-alkynyl, $C_1$-$C_6$-alkoxy, alkyl, $C_1$-$C_4$-haloalkoxy or cyano, Y is preferably hydrogen, halogen, $C_1$-$C_6$-alkyl or $C_1$-$C_6$-alkoxy, Z is preferably a group

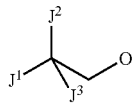

in which $J^1$ and $J^2$ are preferably each independently hydrogen, fluorine or chlorine, and $J^3$ is preferably halogen or $C_1$-$C_4$-haloalkyl, CKE is preferably one of the groups

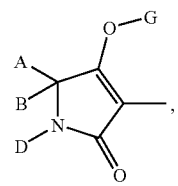
(1)

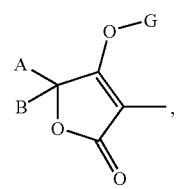
(2)

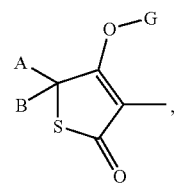
(3)

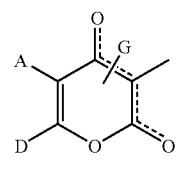
(4)

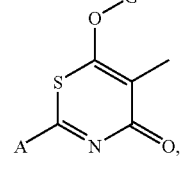
(5)

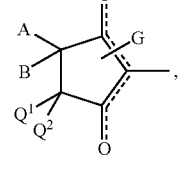
(6)

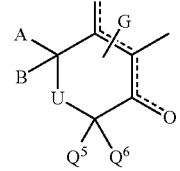
(7)

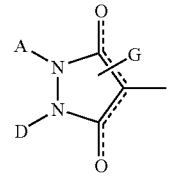
(8)

-continued

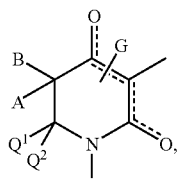
(9)

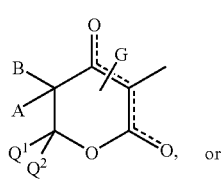
(10)

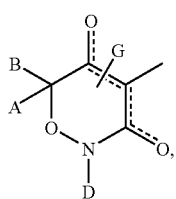
(11)

U is preferably —S—, —S(O)—, —S(O)$_2$—, —O—,

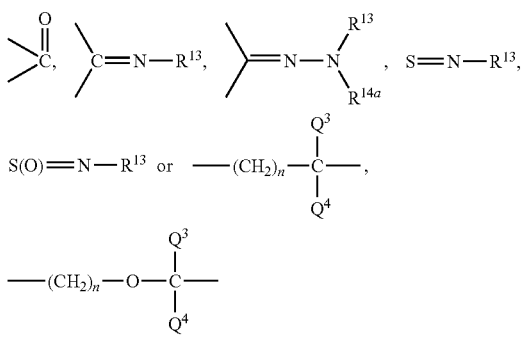

in which n is preferably the number 0, 1 or 2,

A is preferably hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which one or two ring members not directly adjacent are optionally replaced by oxygen and/or sulphur, or is in each case optionally halogen-$C_1$-$C_6$-alkyl-, $C_1$-$C_6$-haloalkyl-, $C_1$-$C_6$-alkoxy, $C_1$-$C_6$-haloalkoxy, cyano- or nitro-substituted phenyl, naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, B is preferably hydrogen, $C_1$-$C_{12}$-alkyl or $C_1$-$C_8$-alkoxy-$C_1$-$C_6$-alkyl or A, B and the carbon atom to which they are bonded are preferably saturated $C_3$-$C_{10}$-cycloalkyl or unsaturated $C_5$-$C_{10}$-cycloalkyl, in which one ring member is optionally replaced by nitrogen, oxygen or sulphur and which is optionally mono- or disubstituted by $C_1$-$C_8$-alkyl, $C_1$-$C_8$-alkoxy, $C_3$-$C_8$-alkenyloxy, $C_1$-$C_6$-alkoxy-$C_1$-$C_6$-alkyl, $C_3$-$C_6$-cycloalkyl-$C_1$-$C_2$-alkoxy, $C_3$-$C_{10}$-cycloalkyl, $C_2$-$C_6$-haloalkoxy, $C_1$-$C_6$-alkoxy-$C_1$-$C_4$-alkoxy, where the aforementioned radicals are also possible nitrogen substituents, or A, B and the carbon atom to which they are bonded are preferably $C_3$-$C_6$-cycloalkyl which is substituted by an optionally $C_1$-$C_4$-alkyl-substituted alkylenediyl group optionally containing one or two oxygen and/or sulphur atoms which are not directly adjacent, or by an alkylenedioxyl or by an alkylenedithioyl group, which group forms a further five- to eight-membered ring with the carbon atom to which it is bonded, or A, B and the carbon atom to which they are bonded are preferably $C_3$-$C_8$-cycloalkyl or $C_5$-$C_8$-cycloalkenyl, in which two substituents together with the carbon atoms to which they are bonded are in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkadienediyl in which one methylene group is optionally replaced by oxygen or sulphur, D is preferably hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_1$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl, in which one ring member is optionally replaced by oxygen or sulphur, or in each case optionally halogen-, $C_1$-$C_6$-alkyl-, $C_1$-$C_6$-haloalkyl-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl), or A and D together are preferably in each case optionally substituted $C_3$-$C_6$-alkanediyl or $C_3$-$C_6$-alkenediyl, in which one methylene group is optionally replaced by a carbonyl group, oxygen or sulphur, and where possible substituents in each case are:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl moiety, $C_3$-$C_6$-alkenediyl moiety or a butadienyl moiety, which is optionally substituted by $C_1$-$C_6$-alkyl or in which two adjacent substituents with the carbon atoms to which they are bonded optionally form a further saturated or unsaturated cycle having 5 or 6 ring atoms (in the case of the compound (I-1), A and D together with the atoms to which they are bonded are then, for example, the AD-1 to AD-10 groups further down), which may contain oxygen or sulphur, or in which one of the following groups

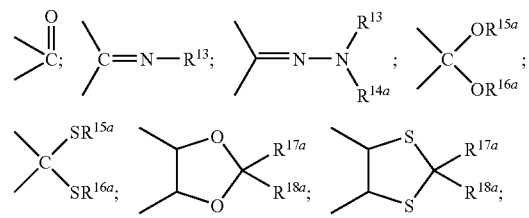

-continued

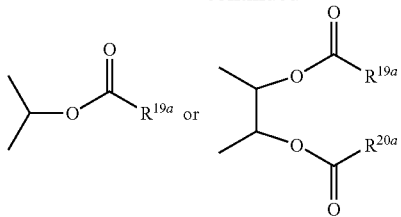

is optionally present, or

A and $Q^1$ together with the carbon atoms to which they are bonded are in each case preferably $C_3$-$C_6$-alkanediyl or $C_4$-$C_6$-alkenediyl each optionally mono- or disubstituted identically or differently by halogen, hydroxyl, by $C_1$-$C_{10}$-alkyl, $C_1$-$C_8$-alkenyl, $C_1$-$C_6$-alkoxy, $C_1$-$C_6$-alkylthio, $C_3$-$C_7$-cycloalkyl each optionally mono- to trisubstituted identically or differently by halogen, or by benzyloxy or phenyl each optionally mono- to trisubstituted identically or differently by halogen, $C_1$-$C_6$-alkyl or $C_1$-$C_6$-alkoxy, and which also optionally contains one of the following groups:

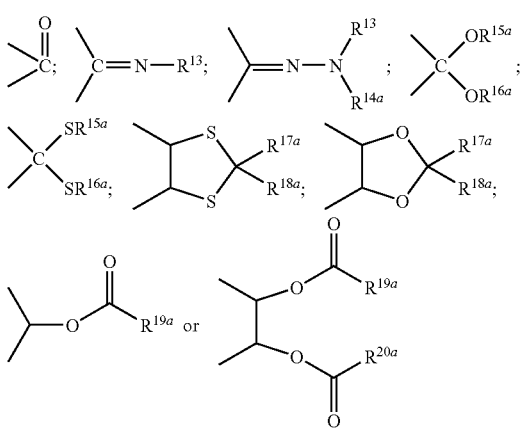

or is bridged by a $C_1$-$C_2$-alkanediyl group or by one oxygen atom, or

B and $Q^2$ together are preferably optionally $C_1$-$C_2$-alkyl-substituted $C_1$-$C_3$-alkanediyl which may optionally be interrupted by oxygen, or D and $Q^1$ together are preferably $C_3$-$C_6$-alkanediyl optionally mono- or disubstituted identically or differently by $C_1$-$C_4$-alkyl, $C_1$-$C_4$-alkoxy, or $Q^1$ is preferably hydrogen, $C_1$-$C_6$-alkyl, $C_1$-$C_6$-alkoxy-$C_1$-$C_2$-alkyl, optionally fluorine-, chlorine-, $C_1$-$C_4$-alkyl-, $C_1$-$C_2$-haloalkyl- or $C_1$-$C_4$-alkoxy-substituted $C_3$-$C_8$-cycloalkyl in which one methylene group is optionally replaced by oxygen or sulphur, or optionally halogen-, $C_1$-$C_4$-alkyl-, $C_1$-$C_2$-haloalkyl-, $C_1$-$C_2$-haloalkoxy-, cyano- or nitro-substituted phenyl, $Q^2$, $Q^4$, $Q^5$ and $Q^6$ are preferably each independently hydrogen or $C_1$-$C_4$-alkyl, $Q^3$ is preferably hydrogen, $C_1$-$C_6$-alkyl, $C_1$-$C_6$-alkoxy, $C_1$-$C_6$-alkoxy-$C_1$-$C_2$-$Q^3$ alkyl, $C_1$-$C_6$-alkylthio-$C_1$-$C_2$-alkyl, optionally $C_1$-$C_4$-alkyl- or $C_1$-$C_4$-alkoxy-substituted $C_3$-$C_8$-cycloalkyl in which one or two methylene groups are optionally replaced by oxygen or sulphur, or optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, or $Q^1$ and $Q^2$ with the carbon atom to which they are bonded are preferably optionally a $C_1$-$C_6$-alkyl-, $C_1$-$C_6$-alkoxy- or $C_1$-$C_2$-haloalkyl-substituted $C_3$-$C_7$ ring in which one ring member is optionally replaced by oxygen or sulphur, $Q^3$ and $Q^4$ together with the carbon atom to which they are bonded are preferably an optionally $C_1$-$C_4$-alkyl-, $C_1$-$C_4$-alkoxy- or $C_1$-$C_2$-haloalkyl-substituted, saturated or unsaturated $C_3$-$C_7$ ring in which one or two ring members are optionally replaced by oxygen or sulphur, A and $Q^3$ together with the carbon atoms to which they are bonded are preferably a saturated or unsaturated, optionally $C_1$-$C_4$-alkyl-, $C_1$-$C_4$-alkoxy- or $C_1$-$C_2$-haloalkyl-substituted $C_3$-$C_7$ ring in which one or two ring members are optionally replaced by oxygen or sulphur, A and $Q^5$ together with the carbon atoms to which they are bonded are preferably a saturated or unsaturated, optionally $C_1$-$C_4$-alkyl-, $C_1$-$C_4$-alkoxy- or $C_1$-$C_2$-haloalkyl-substituted $C_3$-$C_7$ ring in which one ring member is optionally replaced by oxygen or sulphur, G is preferably hydrogen (a) or one of the groups (b)
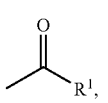

(c)
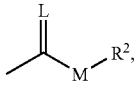

(d)

(e)
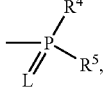

(f)
E or (g)
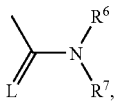

especially (a), (b), (c) or (g)
in which
E is one metal ion equivalent or one ammonium ion,
L is oxygen or sulphur and
M is oxygen or sulphur,
$R^1$ is preferably in each case optionally halogen-substituted $C_1$-$C_{20}$-alkyl, $C_2$-$C_{20}$-alkenyl, $C_1$-$C_8$-alkoxy-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which one or more (preferably not more than two) ring members not directly adjacent are optionally replaced by oxygen and/or sulphur, is optionally halogen-, cyano-, nitro-, $C_1$-$C_6$-alkyl-, $C_1$-$C_6$-alkoxy-, $C_1$-$C_6$-haloalkoxy-, $C_1$-$C_6$-alkylthio- or $C_1$-$C_6$-alkylsulphonyl-substituted phenyl, is optionally halogen-, nitro-, cyano-, $C_1$-$C_6$-alkoxy-, $C_1$-$C_6$-haloalkyl- or $C_1$-$C_6$-haloalkoxy-substituted phenyl-$C_1$-$C_6$-alkyl, is optionally halogen- or $C_1$-$C_6$-alkyl-substituted 5- or 6-membered hetaryl (for example pyrazolyl, thiazolyl, pyridyl, pyrimidyl, furanyl or thienyl), is optionally halogen- or $C_1$-$C_6$-alkyl-substituted phenoxy-$C_1$-$C_6$-alkyl, or is optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ is in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, is optionally halogen-, $C_1$-$C_6$-alkyl- or $C_1$-$C_6$-alkoxy-substituted $C_3$-$C_8$-cycloalkyl or is in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ is preferably optionally halogen-substituted $C_1$-$C_8$-alkyl or in each case optionally halogen-, $C_1$-$C_6$-alkyl-, $C_1$-$C_4$-haloalkyl-, $C_1$-$C_4$-haloalkoxy-, cyano- or nitro-substituted phenyl or benzyl, $R^4$ and $R^5$ are preferably each independently in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_2$-$C_8$-alkenylthio, $C_3$-$C_7$-cycloalkylthio or in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-alkyl- or $C_1$-$C_4$-haloalkyl-substituted phenyl, phenoxy or phenylthio, $R^6$ and $R^7$ are preferably each independently hydrogen, in each case optionally halogen-substituted $C_3$-$C_8$-cycloalkyl, $C_1$-$C_8$-alkoxy, $C_3$-$C_8$-alkenyl, optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl, or together are an optionally $C_1$-$C_4$-alkyl-substituted $C_3$-$C_6$-alkylene radical in which one carbon atom is optionally replaced by oxygen or sulphur, $R^{13}$ is preferably hydrogen, in each case optionally halogen-substituted $C_1$-$C_8$-alkyl or $C_1$-$C_8$-alkoxy (only in the case of the C=N—$R^{13}$ group), optionally halogen-, $C_1$-$C_4$-alkyl- or $C_1$-$C_4$-alkoxy-substituted $C_3$-$C_8$-cycloalkyl in which one methylene group is optionally replaced by oxygen or sulphur, or is in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl, hetaryl-$C_1$-$C_4$-alkyl, or, only in the case of the C=N—$R^{13}$ group, phenyl-$C_1$-$C_4$-alkoxy or hetaryl-$C_1$-$C_4$-alkoxy, $R^{14a}$ is preferably hydrogen or $C_1$-$C_8$-alkyl or $R^{13}$ and $R^{14a}$ together are preferably optionally $C_1$-$C_4$-alkyl-substituted $C_4$-$C_6$-alkanediyl which may optionally be interrupted by oxygen or sulphur, $R^{15a}$ and $R^{16a}$ are the same or different and are preferably each $C_1$-$C_6$-alkyl or $R^{15a}$ and $R^{16a}$ together are preferably a $C_2$-$C_4$-alkanediyl radical or a $C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ are preferably each independently hydrogen, optionally halogen-substituted $C_1$-$C_8$-alkyl or optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are bonded are preferably a carbonyl group or optionally halogen-, $C_1$-$C_4$-alkyl- or $C_1$-$C_4$-alkoxy-substituted $C_5$-$C_7$-cycloalkyl in which one methylene group is optionally replaced by oxygen or sulphur, $R^{19a}$ and $R^{20a}$ are preferably each independently $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions cited as preferred, halogen is fluorine, chlorine, bromine and iodine, especially fluorine, chlorine and bromine.

W is more preferably hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, X is more preferably chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl, $C_1$-$C_2$-haloalkoxy or cyano, Y is more preferably hydrogen, methyl, ethyl, fluorine, chlorine, bromine, iodine, methoxy or ethoxy, Z is more preferably the group

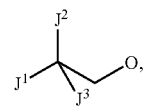

in which $J^1$ and $J^2$ are more preferably each independently hydrogen, fluorine or chlorine, and $J^3$ is fluorine, chlorine, trichloromethyl, difluoromethyl, difluorochloromethyl, dichlorofluoromethyl or trifluoromethyl, CKE is more preferably one of the groups

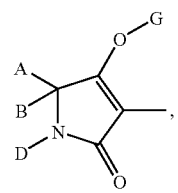

(1)

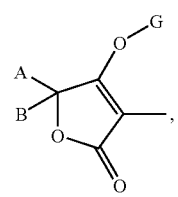

(2)

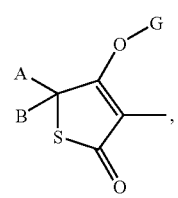

(3)

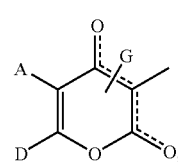

(4)

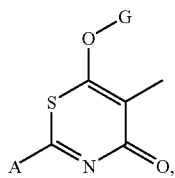

(5)

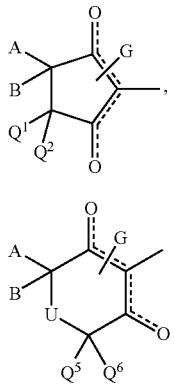

(6)

(7)

(8)

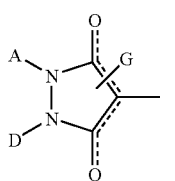

(9)

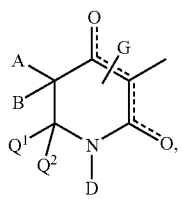

(10)

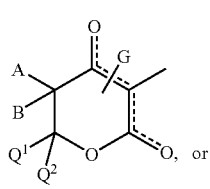

or (11)

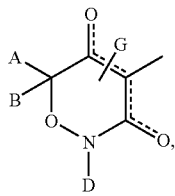

U is more preferably —CH$_2$—, —CH$_2$—CH$_2$—, —O— or

A is more preferably hydrogen, in each case optionally mono- to tri-fluorine- or -chlorine-substituted C$_1$-C$_6$-alkyl, C$_1$-C$_4$-alkoxy-C$_1$-C$_2$-alkyl, optionally mono- to di-C$_1$-C$_2$-alkyl- or —C$_1$-C$_2$-alkoxy-substituted C$_3$-C$_6$-cycloalkyl optionally interrupted by one oxygen atom or (but not in the case of the compounds of the formulae (I-3), (I-4), (I-6), (I-7), (I-9), (I-10) and (I-11)) in each case optionally mono- to di-fluorine-, -chlorine-, -bromine-, —C$_1$-C$_4$-alkyl-, —C$_1$-C$_2$-haloalkyl-, —C$_1$-C$_4$-alkoxy-, —C$_1$-C$_2$-haloalkoxy-, -cyano- or -nitro-substituted phenyl, pyridyl or benzyl, B is more preferably hydrogen, C$_1$-C$_4$-alkyl or C$_1$-C$_2$-alkoxy-C$_1$-C$_2$-alkyl or A, B and the carbon atom to which they are bonded are more preferably saturated or unsaturated C$_3$-C$_7$-cycloalkyl in which one ring member is optionally replaced by nitrogen, oxygen or sulphur and which is optionally mono- to di-C$_1$-C$_6$-alkyl-, —C$_1$-C$_4$-alkoxy-C$_1$-C$_2$-alkyl-, -trifluoromethyl-, —C$_1$-C$_6$-alkoxy-, —C$_3$-C$_6$-alkenyloxy-, -trifluoroethoxy-, —C$_1$-C$_3$-alkoxy-C$_1$-C$_3$-alkoxy- or —C$_3$-C$_6$-cycloalkylmethoxy-substituted, where the aforementioned radicals are also possible nitrogen substituents, with the proviso that Q$^3$ in that case is more preferably hydrogen or methyl, or A, B and the carbon atom to which they are bonded are more preferably C$_5$-C$_6$-cycloalkyl which is substituted by an optionally methyl- or ethyl-substituted alkylenediyl group optionally containing one or two oxygen or sulphur atoms not directly adjacent or by an alkylenedioxy group or by an alkylenedithiol group, which group forms, with the carbon atom to which it is bonded, a further five- or six-membered ring, with the proviso that Q$^3$ in that case is more preferably hydrogen or methyl, or A, B and the carbon atom to which they are bonded are more preferably C$_3$-C$_6$-cycloalkyl or C$_5$-C$_6$-cycloalkenyl in which two substituents together with the carbon atoms to which they are bonded are in each case optionally C$_1$-C$_2$-alkyl- or C$_1$-C$_2$-alkoxy-substituted C$_2$-C$_4$-alkanediyl, C$_2$-C$_4$-alkenediyl or butadienediyl, with the proviso that Q$^3$ in that case is more preferably hydrogen or methyl, D is more preferably hydrogen, in each case optionally mono- to tri-fluorine-substituted C$_1$-C$_6$-alkyl, C$_3$-C$_6$-alkenyl, C$_1$-C$_4$-alkoxy-C$_1$-C$_3$-alkyl, in each case optionally mono- to di-C$_1$-C$_4$-alkyl-, —C$_1$-C$_4$-alkoxy- or —C$_1$-C$_2$-haloalkyl-substituted C$_3$-C$_6$-cycloalkyl in which one methylene group is optionally replaced by oxygen or (only in the case of the compounds of the formula (I-4)) is in each case optionally mono- to di-fluorine-, -chlorine-, -bromine-, —C$_1$-C$_4$-alkyl-, —C$_1$-C$_4$-haloalkyl-, —C$_1$-C$_4$-alkoxy- or —C$_1$-C$_4$-haloalkoxy-substituted phenyl or pyridyl, or A and D together are more preferably optionally mono- to disubstituted C$_3$-C$_5$-alkanediyl in which one methylene group may be replaced by a carbonyl group (but not in the case of the compounds of the formula (I-11)), oxygen or sulphur, where possible substituents are C$_1$-C$_2$-alkyl or C$_1$-C$_2$-alkoxy, or A and D (in the case of the compounds of the formula (I-1)) together with the atoms to which they are bonded are one of the groups AD-1 to AD-10:

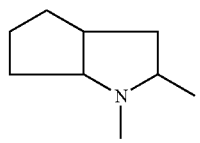

AD-1

AD-2 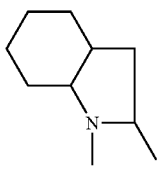

AD-3 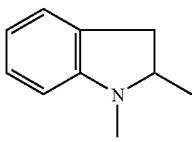

AD-4 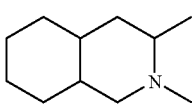

AD-5 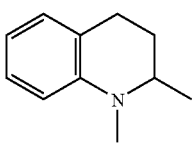

AD-6 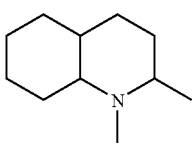

AD-7 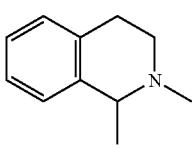

AD-8 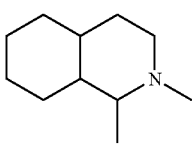

AD-9 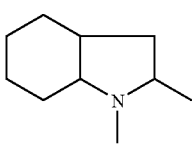

AD-10 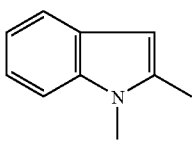

or

A and D together are more preferably $C_3$-$C_5$-alkanediyl which is optionally substituted by an optionally mono- to tetra-$C_1$-$C_4$-alkyl- or —$C_1$-$C_3$-alkoxy-$C_1$-$C_2$-alkyl-substituted alkylenedioxy group containing two oxygen atoms not directly adjacent, to form a further 5- or 6-membered ring, or A and $Q^1$ together are more preferably $C_3$-$C_4$-alkanediyl which is optionally mono- or disubstituted identically or differently by $C_1$-$C_2$-alkyl or $C_1$-$C_2$-alkoxy, and which optionally contains the following group:

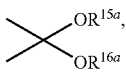

in which $R^{15a}$ and $R^{16a}$ are more preferably the same or different and are each methyl or ethyl, or $R^{15a}$ and $R^{16a}$ together are more preferably a $C_2$-$C_4$-alkanediyl or $C_4$-alkenediyl radical which is optionally substituted by methyl or ethyl, or B and $Q^2$ together are more preferably —$CH_2$—, —$CH_2$—$CH_2$—, —$CH_2$—$CH_2$—$CH_2$—, or —$CH_2$—O—$CH_2$—, or D and $Q^1$ together are more preferably $C_3$-$C_4$-alkanediyl, or $Q^1$ is more preferably hydrogen, $C_1$-$C_4$-alkyl, $C_1$-$C_4$-alkoxy-$C_1$-$C_2$-alkyl, or optionally methyl- or methoxy-substituted $C_3$-$C_6$-cycloalkyl in which one methylene group is optionally replaced by oxygen, $Q^2$ is more preferably hydrogen, methyl or ethyl, $Q^4$, $Q^5$ and $Q^6$ are more preferably each independently hydrogen or $C_1$-$C_3$-alkyl, $Q^3$ is more preferably hydrogen, $C_1$-$C_4$-alkyl, $C_1$-$C_4$-alkoxy, or optionally mono- to di-methyl- or methoxy-substituted $C_3$-$C_6$-cycloalkyl optionally interrupted by one oxygen atom, or $Q^1$ and $Q^2$ with the carbon to which they are bonded are more preferably optionally methyl- or methoxy-substituted $C_3$-$C_6$-cycloalkyl in which one methylene group is optionally replaced by oxygen, with the proviso that A and B in that case are more preferably each independently hydrogen or methyl, or $Q^3$ and $Q^4$ together with the carbon to which they are bonded are more preferably an optionally $C_1$-$C_2$-alkyl- or $C_1$-$C_2$-alkoxy-substituted saturated $C_5$-$C_6$ ring in which one or two ring members are optionally replaced by oxygen or sulphur, with the proviso that A in that case is more preferably hydrogen or methyl, or A and $Q^3$ together with the carbon to which they are bonded are more preferably an optionally $C_1$-$C_2$-alkyl- or $C_1$-$C_2$-alkoxy-substituted saturated $C_5$-$C_6$ ring in which one ring member is optionally replaced by oxygen or sulphur, with the proviso that B, $Q^4$, $Q^5$ and $Q^6$ in that case are more preferably each independently hydrogen or methyl, or A and $Q^5$ together with the carbon atoms to which they are bonded are more preferably an optionally $C_1$-$C_2$-alkyl- or $C_1$-$C_2$-alkoxy-substituted saturated or unsaturated $C_5$-$C_6$ ring, with the proviso that B, $Q^3$, $Q^4$ and $Q^6$ in that case are more preferably each independently hydrogen or methyl, G is more preferably hydrogen (a) or one of the groups (b)

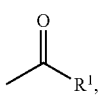

(c)

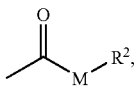

-continued

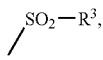

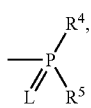

E or

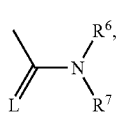

(g), especially (a), (b) or (c),
in which
E is one metal ion equivalent or one ammonium ion,
L is oxygen or sulphur and
M is oxygen or sulphur,
$R^1$ is more preferably in each case optionally mono- to trifluorine- or -chlorine-substituted $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl or optionally mono- to di-fluorine-, -chlorine-, —$C_1$-$C_2$-alkyl- or —$C_1$-$C_2$-alkoxy-substituted $C_3$-$C_6$-cycloalkyl in which one or two ring members not directly adjacent are optionally replaced by oxygen,
is optionally mono- to di-fluorine-, -chlorine-, -bromine-, -cyano-, -nitro-, —$C_1$-$C_4$-alkyl-, —$C_1$-$C_4$-alkoxy-, —$C_1$-$C_2$-haloalkyl- or —$C_1$-$C_2$-haloalkoxy-substituted phenyl,
$R^2$ is more preferably in each case optionally mono- to trifluorine-substituted $C_1$-$C_8$-alkyl, $C_2$-$C_8$-alkenyl or $C_1$-$C_4$-alkoxy-$C_2$-$C_4$-alkyl,
is optionally mono-$C_1$-$C_2$-alkyl- or —$C_1$-$C_2$-alkoxy-substituted $C_3$-$C_6$-cycloalkyl or
is in each case optionally mono- to di-fluorine-, -chlorine-, -bromine-, -cyano-, -nitro-, —$C_1$-$C_4$-alkyl-, —$C_1$-$C_3$-alkoxy-, -trifluoromethyl- or -trifluoromethoxy-substituted phenyl or benzyl,
$R^3$ is more preferably optionally mono- to tri-fluorine-substituted $C_1$-$C_6$-alkyl or optionally mono-fluorine-, -chlorine-, -bromine-, —$C_1$-$C_4$-alkyl-, —$C_1$-$C_4$-alkoxy-, -trifluoromethyl-, -trifluoromethoxy-, -cyano- or -nitro-substituted phenyl,
$R^4$ is more preferably $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio, or in each case optionally mono-fluorine-, -chlorine-, -bromine-, -nitro-, -cyano-, —$C_1$-$C_3$-alkoxy-, —$C_1$-$C_3$-haloalkoxy-, —$C_1$-$C_3$-alkylthio-, —$C_1$-$C_3$-haloalkylthio-, —$C_1$-$C_3$-alkyl- or -trifluoromethyl-substituted phenyl, phenoxy or phenylthio,
$R^5$ is more preferably $C_1$-$C_6$-alkoxy or $C_1$-$C_6$-alkylthio,
$R^6$ is more preferably hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, optionally mono-fluorine-, -chlorine-, -bromine-, -trifluoromethyl-, —$C_1$-$C_4$-alkyl- or —$C_1$-$C_4$-alkoxy-substituted phenyl, optionally mono-fluorine-, -chlorine-, -bromine-, —$C_1$-$C_4$-alkyl-, -trifluoromethyl- or —$C_1$-$C_4$-alkoxy-substituted benzyl,
$R^7$ is more preferably $C_1$-$C_6$-alkyl, $C_3$-$C_6$-alkenyl or $C_1$-$C_6$-alkoxy-$C_1$-$C_4$-alkyl,
$R^6$ and $R^7$ together are more preferably an optionally methyl- or ethyl-substituted $C_{4-5}$-alkylene radical in which one methylene group is optionally replaced by oxygen or sulphur.

In the radical definitions cited as particularly preferred, halogen is fluorine, chlorine and bromine, especially fluorine and chlorine.

W is even more preferably hydrogen, chlorine, methyl or ethyl,

X is even more preferably chlorine, methyl, ethyl, methoxy or ethoxy,

Y is even more preferably hydrogen, methyl or chlorine,

Z is even more preferably the group

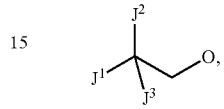

in which $J^1$ and $J^2$ are even more preferably each independently hydrogen or fluorine and $J^3$ is fluorine, chlorine or trifluoromethyl, CKE is even more preferably one of the groups

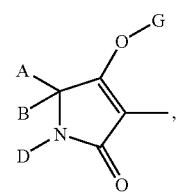

(1)

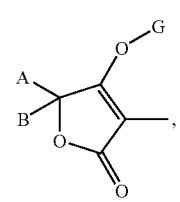

(2)

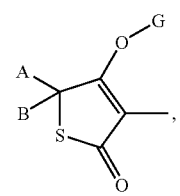

(3)

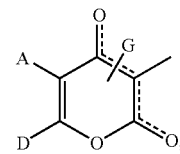

(4)

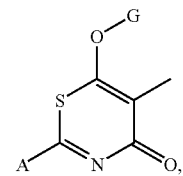

(5)

-continued (6) 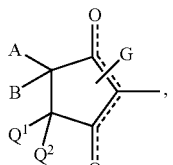

(7) 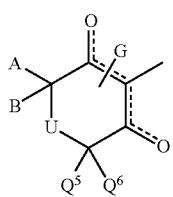

(8) 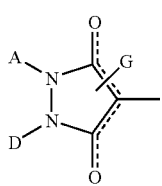

(9) 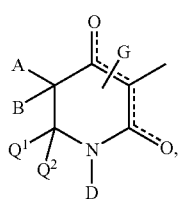

(10) 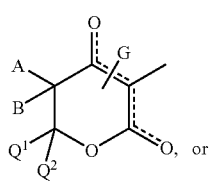

(11) 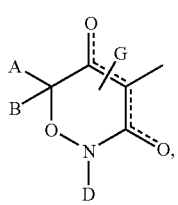

U is even more preferably —CH$_2$—, —CH$_2$—CH$_2$—, —O— or

A is even more preferably hydrogen, in each case optionally mono- to tri-fluorine-substituted C$_1$-C$_4$-alkyl or C$_1$-C$_2$-alkoxy-C$_1$-C$_2$-alkyl, or is cyclopropyl, cyclopentyl or cyclohexyl, and in the case of the compounds of the formula (I-5) is optionally mono- to di-fluorine-, -chlorine-, -bromine-, -methyl-, -ethyl-, -n-propyl-, -isopropyl-, -methoxy-, -ethoxy-, -trifluoromethyl-, -trifluoromethoxy-, -cyano- or -nitro-substituted phenyl, B is even more preferably hydrogen, methyl or ethyl, or A, B and the carbon atom to which they are bonded are even more preferably saturated C$_5$-C$_6$-cycloalkyl in which one ring member is optionally replaced by nitrogen, oxygen or sulphur and which is optionally mono- or di-methyl-, -ethyl-, -methoxymethyl-, -ethoxymethyl-, -methoxyethyl-, -ethoxyethyl-, -trifluoromethyl-, -methoxy-, -ethoxy-, -propoxy-, -butoxy-, -methoxyethoxy-, -ethoxyethoxy-, -allyloxy-, -trifluoroethoxy- or -cyclopropylmethoxy-substituted, where the aforementioned radicals are also possible nitrogen substitutents, with the proviso that Q$^3$ in that case is even more preferably hydrogen, or A, B and the carbon atom to which they are bonded are even more preferably C$_6$-cycloalkyl which is optionally substituted by an alkylidenediyl group optionally interrupted by one oxygen atom or by an alkylenedioxy group optionally containing two oxygen atoms not directly adjacent, to form a further 5- or 6-membered ring (which may be mono- or di-methyl-substituted), with the proviso that Q$^3$ in that case is even more preferably hydrogen, or A, B and the carbon atom to which they are bonded are even more preferably C$_5$-C$_6$-cycloalkyl or C$_5$-C$_6$-cycloalkenyl, in which two substituents together with the carbon atoms to which they are bonded are C$_2$-C$_4$-alkanediyl or C$_2$-C$_4$-alkenediyl or butadienediyl, with the proviso that Q$^3$ in that case is even more preferably hydrogen, D is even more preferably hydrogen, in each case optionally mono- to tri-fluorine-substituted C$_1$-C$_4$-alkyl, C$_3$-C$_4$-alkenyl, C$_1$-C$_4$-alkoxy-C$_1$-C$_3$-alkyl, or is cyclopropyl, cyclopentyl or cyclohexyl, or (in the case of the compounds of the formula (I-4)) is in each case optionally mono-fluorine-, -chlorine-, -methyl-, -ethyl-, -n-propyl-, -isopropyl-, -methoxy-, -ethoxy- or -trifluoromethyl-substituted phenyl or pyridyl, or A and D together are even more preferably optionally monomethyl- or -methoxy-substituted C$_3$-C$_5$-alkanediyl in which one carbon atom is optionally replaced by a carbonyl group (but not in the case of the compound of the formula (I-11)), oxygen or sulphur, or is the AD-1 group, or A and D together are even more preferably C$_3$-C$_5$-alkanediyl which is optionally substituted by an optionally mono- to di-C$_1$-C$_2$-alkyl-substituted alkylenedioxy group containing two oxygen atoms not directly adjacent, to form a further 5-membered ring, or A and Q$^1$ together are even more preferably optionally mono- or di-methyl- or -methoxy-substituted C$_3$-C$_4$-alkanediyl which optionally contains the following group:

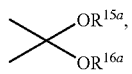

in which R$^{15a}$ and R$^{16a}$ together are even more preferably a C$_2$-C$_4$-alkanediyl or C$_4$-alkenediyl radical, or B and Q$^2$ together are even more preferably —CH$_2$—CH$_2$—CH$_2$—, or —CH$_2$—O—CH$_2$—, or D and Q$^1$ together are even more preferably C$_3$-C$_4$-alkanediyl, or Q$^1$ is even more preferably hydrogen, methyl, ethyl, propyl, isopropyl, cyclopropyl, cyclopentyl or cyclohexyl, Q$^2$ is even more preferably hydrogen, methyl or ethyl, Q$^4$, Q$^5$ and Q$^6$ are even more preferably each independently hydrogen or methyl, Q$^3$ is even more preferably hydrogen, methyl, ethyl, propyl, methoxy or ethoxy, or optionally mono-methyl- or -methoxy-substituted C$_3$-C$_6$-cycloalkyl optionally interrupted by one oxygen atom, or $Q^1$ and $Q^2$ with the carbon atom to which they are bonded are even more preferably optionally methyl- or methoxy-substituted $C_5$-$C_6$-cycloalkyl in which one methylene group is optionally replaced by oxygen, with the proviso that A and B are each hydrogen, or $Q^3$ and $Q^4$ together with the carbon to which they are bonded are even more preferably an optionally mono-methyl- or -methoxy-substituted, saturated $C_5$-$C_6$ ring optionally interrupted by one oxygen atom, with the proviso that A, B, $Q^5$ and $Q^6$ in that case are even more preferably hydrogen, G is even more preferably hydrogen (a) or one of the groups

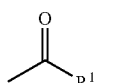    (b)

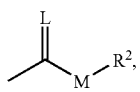    (c)

—$SO_2$—$R^3$ (d) or E (f), in which
L is oxygen or sulphur,
M is oxygen or sulphur and
E is one metal ion equivalent or one ammonium ion,
$R^1$ is even more preferably in each case optionally monochlorine-substituted $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, or in each case optionally mono-fluorine-, -chlorine-, -methyl- or -methoxy-substituted cyclopropyl or cyclohexyl, optionally mono-fluorine-, -chlorine-, -bromine-, -cyano-, -nitro-, -methyl-, -methoxy-, -trifluoromethyl- or -trifluoromethoxy-substituted phenyl,
$R^2$ is even more preferably in each case optionally mono-fluorine-substituted $C_1$-$C_8$-alkyl, $C_2$-$C_6$-alkenyl or $C_1$-$C_4$-alkoxy-$C_2$-$C_3$-alkyl, phenyl or benzyl,
$R^3$ is even more preferably $C_1$-$C_8$-alkyl,
W is especially preferably hydrogen, methyl or ethyl,
X is especially preferably chlorine, methyl or ethyl,
Y is especially preferably hydrogen,
Z is especially preferably $OCH_2$—$CF_3$ in the 3 position,
Z is especially preferably also $OCH_2$—$CF_3$ in the 4 position,
Z is especially preferably likewise $OCH_2$—$CF_3$ in the 5 position,
CKE is especially preferably one of the groups

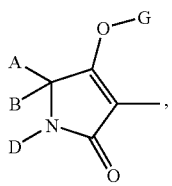    (1)

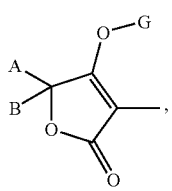    (2)

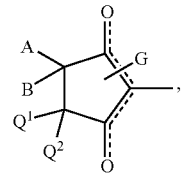    (6)

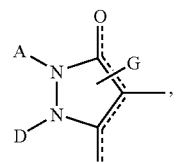    (8)

A is especially preferably methyl or ethyl,
B is especially preferably hydrogen or methyl,
A, B and the carbon atom to which they are bonded are especially preferably saturated $C_5$-$C_6$-cycloalkyl in which one ring member is optionally replaced by oxygen and which is optionally mono- or di-methyl-, -ethyl-, -methoxymethyl-, -methoxy-, -ethoxy-, -propoxy-, -butoxy-, -trifluoroethoxy-substituted, or
A, B and the carbon atom to which they are bonded are especially preferably $C_6$-cycloalkyl which is optionally substituted by an alkylenedioxy group containing two oxygen atoms not directly adjacent, to form a further 5- or 6-membered ring which may be mono- or di-methyl-substituted,
D is especially preferably hydrogen, or
A and D together are especially preferably $C_3$-$C_5$-alkanediyl in which one carbon atom is optionally replaced by oxygen, or
A and D together are especially preferably $C_3$-$C_5$-alkanediyl which is optionally substituted by an optionally mono- to di-methyl-substituted alkylenedioxy group optionally containing two oxygen atoms not directly adjacent, to form a further 5-membered ring (with emphasis, A and D together are $C_3$-$C_5$-alkanediyl which is optionally substituted by an alkylenedioxy group containing two oxygen atoms not directly adjacent, to form a further 5-membered ring), or
A and $Q^1$ together are especially preferably $C_3$-$C_4$-alkanediyl,
$Q^2$ is especially preferably hydrogen,
G is especially preferably hydrogen (a) or one of the groups

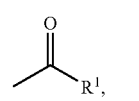    (b)

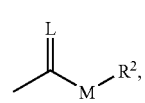    (c)

in which
L is oxygen,
M is oxygen,
$R^1$ is especially preferably $C_1$-$C_6$-alkyl,
$R^2$ is especially preferably $C_1$-$C_6$-alkyl.

The radical definitions and illustrations generalized above or listed in preferred ranges can be combined as desired with one another, i.e. including between the particular ranges and preferred ranges. They apply correspondingly to the end products, and to the precursors and intermediates.

Preference is given in accordance with the invention to the compounds of the formula (I) in which there is a combination of the definitions listed above as preferred (preferably).

Particular preference is given in accordance with the invention to the compounds of the formula (I) in which there is a combination of the definitions listed above as particularly preferred.

Very particular preference is given in accordance with the invention to the compounds of the formula (I) in which there is a combination of the definitions listed above as even more preferred.

Special preference is given in accordance with the invention to the compounds of the formula (I) in which there is a combination of the definitions listed above as especially preferred.

Emphasis is given to compounds of the formula (I) in which G is hydrogen.

Saturated or unsaturated hydrocarbon radicals such as alkyl, alkanediyl or alkenyl may, also in conjunction with heteroatoms, for example in alkoxy, as far as possible, each be straight-chain or branched.

Optionally substituted radicals may, unless stated otherwise, be substituted once or more than once, and the substituents in the case of polysubstitutions may be the same or different.

Apart from the compounds cited in the examples, specific mention should be made of the following compounds where $Z=OCH_2-CF_3$:

TABLE 1

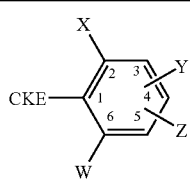

| X | W | Y | Z |
|---|---|---|---|
| $CH_3$ | H | H | 4 |
| $CH_3$ | H | H | 5 |
| Cl | H | H | 4 |
| Cl | H | H | 5 |
| $OCH_3$ | H | H | 4 |
| $OCH_3$ | H | H | 5 |
| $C_2H_5$ | H | H | 4 |
| $C_2H_5$ | H | H | 5 |
| $CH_3$ | $CH_3$ | H | 4 |
| $CH_3$ | $CH_3$ | H | 5 |
| $C_2H_5$ | $CH_3$ | H | 4 |
| $C_2H_5$ | $C_2H_5$ | H | 4 |
| $CH_3$ | Cl | H | 4 |
| $C_2H_5$ | Cl | H | 4 |

Useful inventive active ingredients are especially preferably compounds of the radical combinations for W, X, Y and Z specified in Table 1 with the radical combinations for A, B and D cited in Tables 2a and 2b.

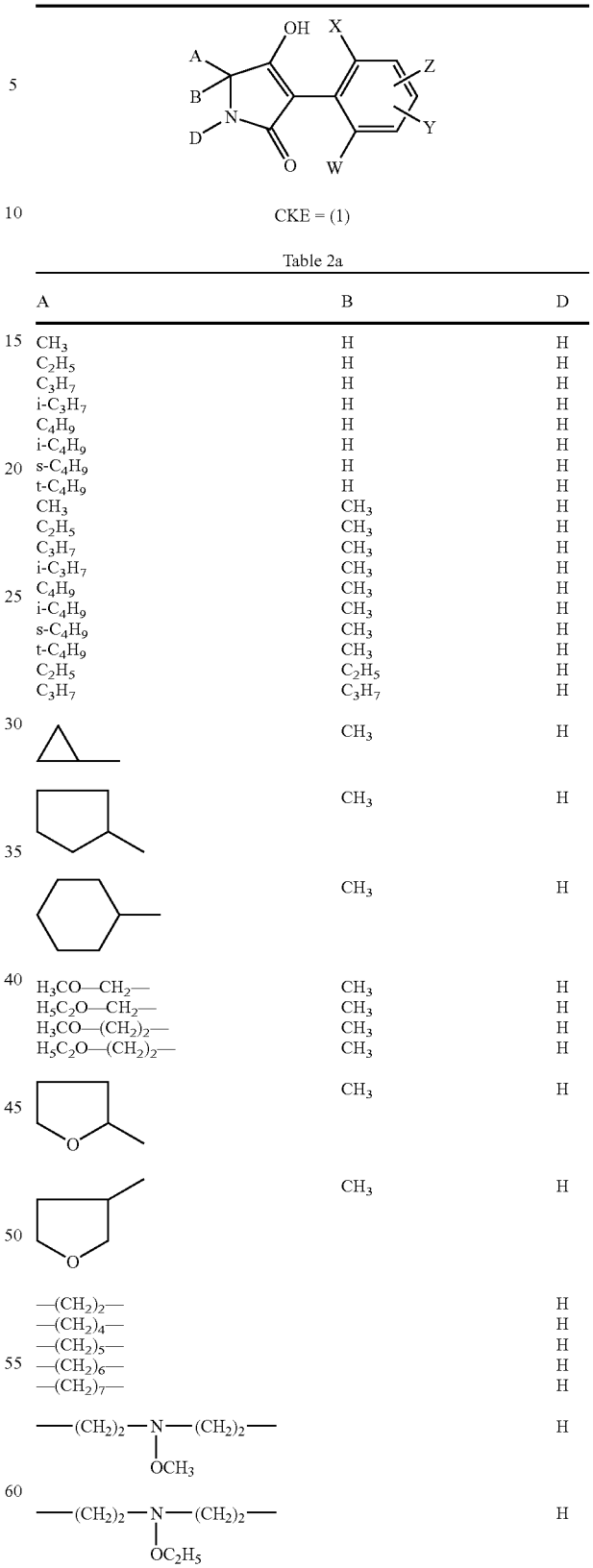

CKE = (1)

Table 2a

| A | B | D |
|---|---|---|
| $CH_3$ | H | H |
| $C_2H_5$ | H | H |
| $C_3H_7$ | H | H |
| $i-C_3H_7$ | H | H |
| $C_4H_9$ | H | H |
| $i-C_4H_9$ | H | H |
| $s-C_4H_9$ | H | H |
| $t-C_4H_9$ | H | H |
| $CH_3$ | $CH_3$ | H |
| $C_2H_5$ | $CH_3$ | H |
| $C_3H_7$ | $CH_3$ | H |
| $i-C_3H_7$ | $CH_3$ | H |
| $C_4H_9$ | $CH_3$ | H |
| $i-C_4H_9$ | $CH_3$ | H |
| $s-C_4H_9$ | $CH_3$ | H |
| $t-C_4H_9$ | $CH_3$ | H |
| $C_2H_5$ | $C_2H_5$ | H |
| $C_3H_7$ | $C_3H_7$ | H |
| cyclopropyl | $CH_3$ | H |
| cyclopentyl | $CH_3$ | H |
| cyclohexyl | $CH_3$ | H |
| $H_3CO-CH_2-$ | $CH_3$ | H |
| $H_5C_2O-CH_2-$ | $CH_3$ | H |
| $H_3CO-(CH_2)_2-$ | $CH_3$ | H |
| $H_5C_2O-(CH_2)_2-$ | $CH_3$ | H |
| tetrahydrofuran-2-yl | $CH_3$ | H |
| tetrahydrofuran-3-yl | $CH_3$ | H |
| $-(CH_2)_2-$ | | H |
| $-(CH_2)_4-$ | | H |
| $-(CH_2)_5-$ | | H |
| $-(CH_2)_6-$ | | H |
| $-(CH_2)_7-$ | | H |
| $-(CH_2)_2-N(OCH_3)-(CH_2)_2-$ | | H |
| $-(CH_2)_2-N(OC_2H_5)-(CH_2)_2-$ | | H |
| $-(CH_2)_2-O-(CH_2)_2-$ | | H |
| $-CH_2-O-(CH_2)_3-$ | | H |
| $-(CH_2)_2-S-(CH_2)_2-$ | | H |

-continued

—CH₂—CHCH₃—(CH₂)₃—  H
—CH₂—CHOCH₃—(CH₂)₂—  H
—CH₂—CHOC₂H₅—(CH₂)₂—  H
—CH₂—CHOC₃H₇—(CH₂)₂—  H
—CH₂—CHOC₄H₉—(CH₂)₂—  H
—CH₂—CHO(CH₂)₂OCH₃—(CH₂)₂—  H

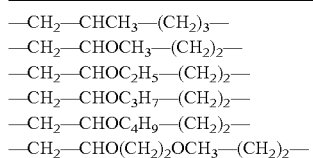  H

—CH₂—CHOCH₃—(CH₂)₃—  H
—CH₂—CHOC₂H₅—(CH₂)₃—  H
—CH₂—CHOC₃H₇—(CH₂)₃—  H
—CH₂—CHOC₄H₉—(CH₂)₃—  H
—CH₂—CHO(CH₂)₂OCH₃—(CH₂)₃—  H

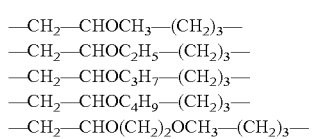  H

—(CH₂)₂—CHCH₃—(CH₂)₂—  H
—(CH₂)₂—CHC₂H₅—(CH₂)₂—  H
—(CH₂)₂—CHC₃H₇—(CH₂)₂—  H
—(CH₂)₂—CHi-C₃H₇—(CH₂)₂—  H
—(CH₂)₂—CHOCH₃—(CH₂)₂—  H
—(CH₂)₂—CHOC₂H₅—(CH₂)₂—  H
—(CH₂)₂—CHOC₃H₇—(CH₂)₂—  H
—(CH₂)₂—CHO—CH₂CF₃—(CH₂)₂—  H
—(CH₂)₂—C(CH₃)₂—(CH₂)₂—  H
—CH₂—(CHCH₃)₂—(CH₂)₂—  H

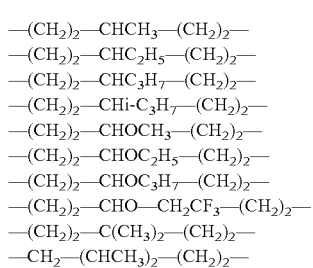  H

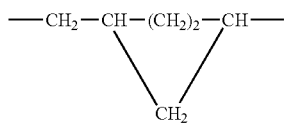  H

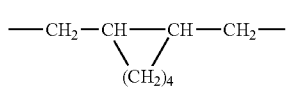  H

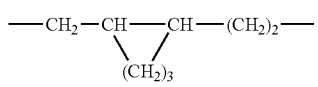  H

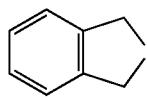  H

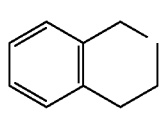  H

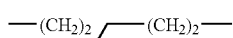  H

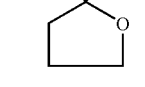  H

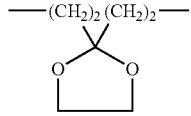  H

-continued

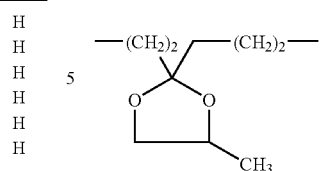  H

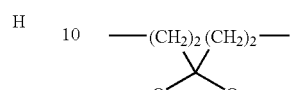  H

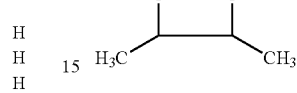  H

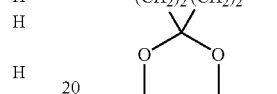  H

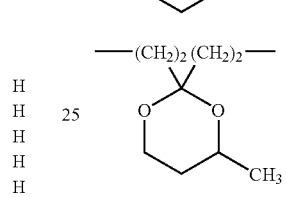  H

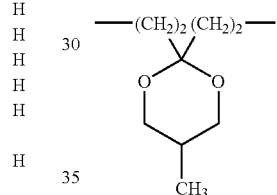  H

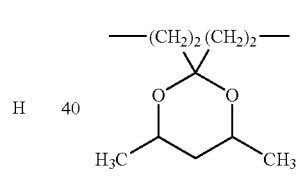  H

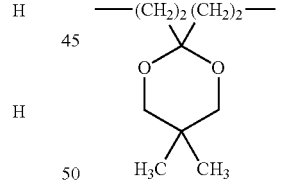  H

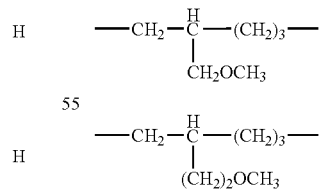  H

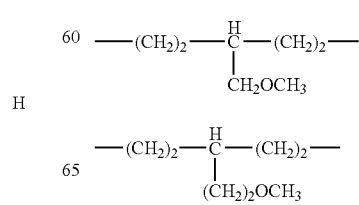  H

TABLE 2b

| A | D | B |
|---|---|---|
| 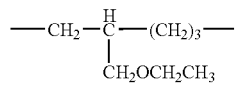 | | H |
| 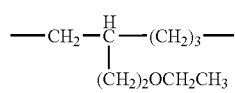 | | H |
| 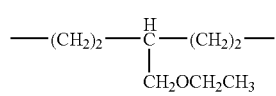 | | H |
| 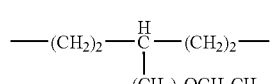 | | H |

TABLE 2b

| A | D | B |
|---|---|---|
| —(CH₂)₃— | | H |
| —(CH₂)₄— | | H |
| —CH₂—CHCH₃—CH₂— | | H |
| —CH₂—CH₂—CHCH₃— | | H |
| —CH₂—CHCH₃—CHCH₃— | | H |
| —CH₂—CH(OCH₃)—CH₂— | | H |
| —CH₂—CH=CH—CH₂— | | H |
| 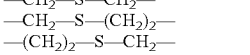 | | H |
| —CH₂—S—CH₂— | | H |
| —CH₂—S—(CH₂)₂— | | H |
| —(CH₂)₂—S—CH₂— | | H |
| 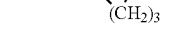 | | H |
| H | CH₃ | H |
| H | C₂H₅ | H |
| H | C₃H₇ | H |
| H | i-C₃H₇ | H |
| H |  | H |
| H | 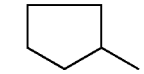 | H |
| H | 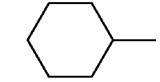 | H |
| CH₃ | CH₃ | H |
| CH₃ | C₂H₅ | H |
| CH₃ | C₃H₇ | H |
| CH₃ | i-C₃H₇ | H |
| CH₃ |  | H |
| CH₃ | 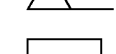 | H |

TABLE 2b-continued

| A | D | B |
|---|---|---|
| CH₃ | 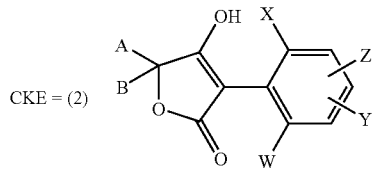 | H |
| C₂H₅ | CH₃ | H |
| C₂H₅ | C₂H₅ | H |
| H | H₃CO—(CH₂)₂— | H |
| H | H₅C₂O—(CH₂)₂— | H |
| H | H₃CO—CH₂—CH(CH₃)— | H |
| H | H₃CO—CHCH₃—CH₂— | H |
| CH₃ | H₃CO—(CH₂)₂— | H |
| CH₃ | H₅C₂O—(CH₂)₂— | H |
| CH₃ | H₃CO—CH₂—CH(CH₃)— | H |
| CH₃ | H₃CO—CHCH₃—CH₂— | H |

Active ingredients emphasized are especially preferred compounds with the radical combinations for W, X, Y and Z specified in Table 1 and the radical combinations specified for A, B and D in Tables 2a and 2b.

Useful inventive active ingredients additionally especially preferably include compounds of radical combinations for W, X, Y and Z specified in Table 1 with the radical combinations for A and B specified in Table 3.

TABLE 3

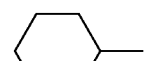

CKE = (2)

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
|  | CH₃ |
|  | CH₃ |
| 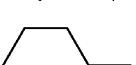 | CH₃ |
| H₃CO—CH₂— | CH₃ |
| H₅C₂O—CH₂— | CH₃ |
| H₃CO—(CH₂)₂— | CH₃ |
| H₅C₂O—(CH₂)₂— | CH₃ |

TABLE 3-continued
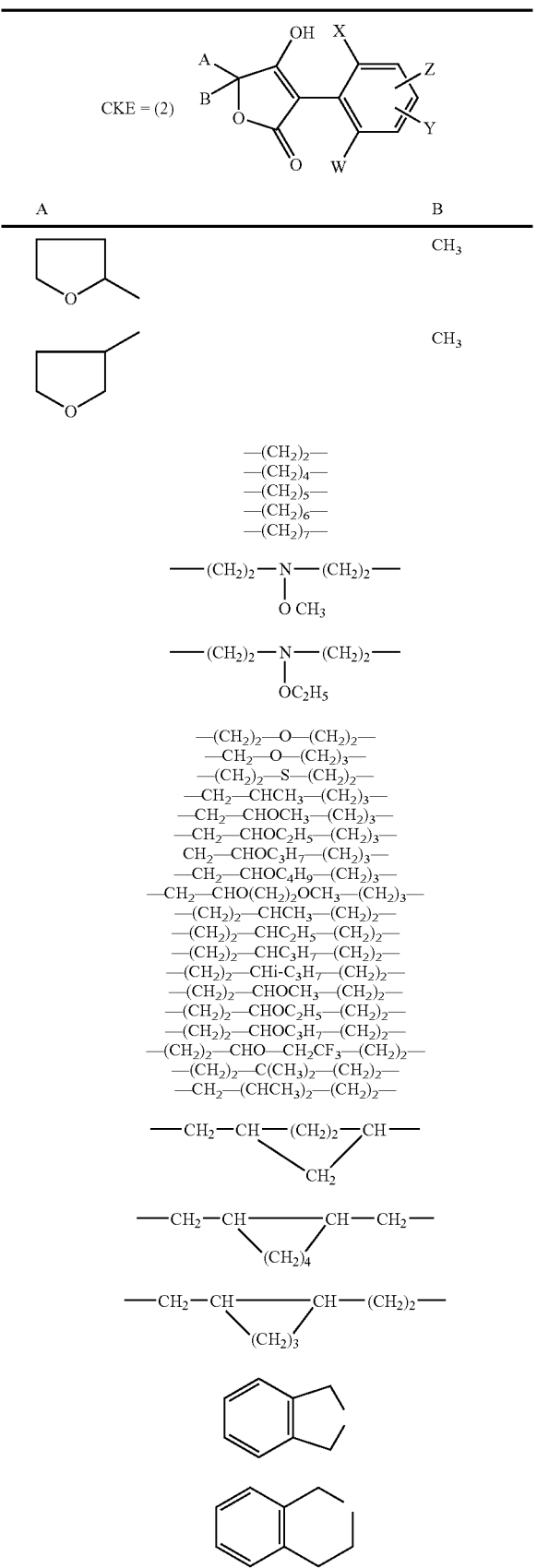
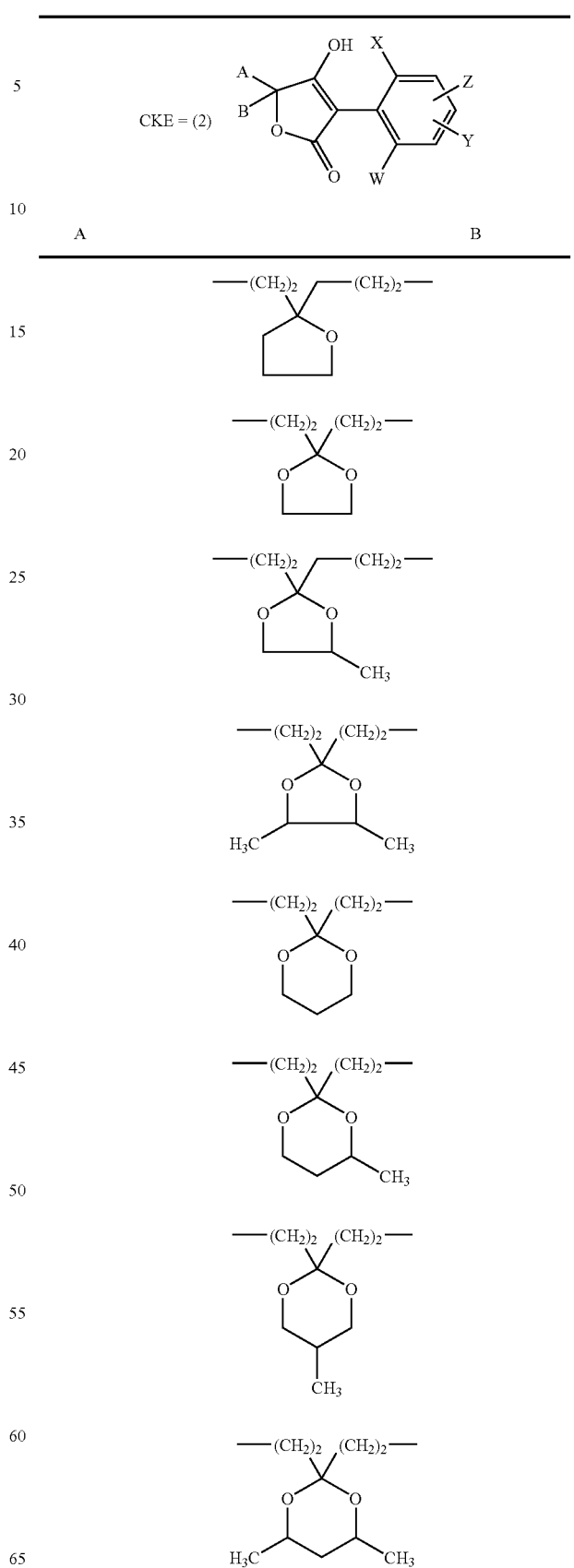

TABLE 3-continued

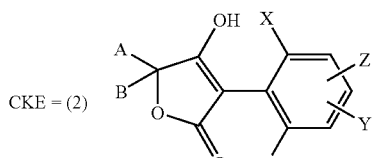

CKE = (2)

A | B
---|---

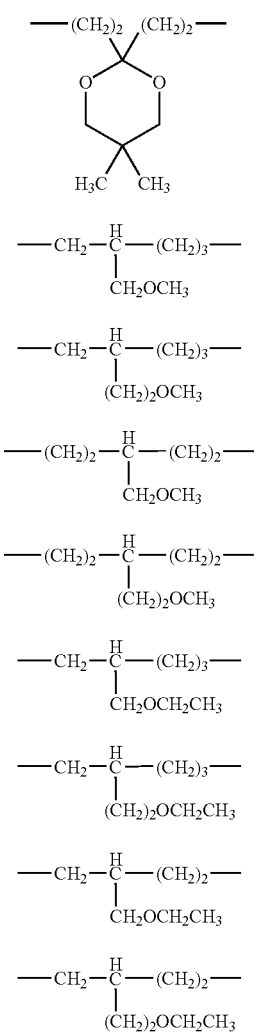

active ingredients and/or particular applications of the corresponding compositions. In other cases, in turn, the salts in question are those of sulphonic acids, where the acids themselves have a paralytic action on insects (U.S. Pat. No. 2,842, 476). A boost to action by ammonium sulphate, for example, is described by way of example for the herbicides glyphosate, phosphinothricin and for phenyl-substituted cyclic ketoenols (U.S. Pat. No. 6,645,914, EP-A2 0 036 106, WO 07/068,427). A corresponding boost to action in the case of insecticides has already been described by WO 07/068,428.

The use of ammonium sulphate as a formulating assistant has also been described for certain active ingredients and applications (WO 92/16108), but its purpose therein is to stabilize the formulation, not to boost the action.

It has now been found, likewise surprisingly, that the action of insecticides and/or acaricides and/or herbicides from the class of the haloalkylmethyleneoxyphenyl-substituted ketoenols of the formula (I) can be boosted significantly through the addition of ammonium salts or phosphonium salts to the application solution or through the incorporation of these salts into a formulation comprising the haloalkylmethyleneoxyphenyl-substituted ketoenols of the formula (I). The present invention therefore provides for the use of ammonium salts or phosphonium salts for boosting the action of crop protection compositions which comprise as their active ingredient herbicidal and/or insecticidal and/or acaricidal haloalkylmethyleneoxyphenyl-substituted ketoenols of the formula (I). The invention likewise provides compositions which comprise herbicidal and/or acaricidal and/or insecticidal haloalkylmethyleneoxyphenyl-substituted ketoenols of the formula (I) and action-boosting ammonium salts or phosphonium salts, including not only formulated active ingredients but also ready-to-use compositions (spray liquors). The invention further provides, finally, for the use of these compositions for controlling insect pests and/or spider mites and/ or unwanted plant growth.

The compounds of the formula (I) possess a broad insecticidal and/or acaricidal and/or herbicidal activity, but in specific cases the activity and/or plant tolerance leaves something to be desired.

The active ingredients can be used in the compositions according to the invention in a broad concentration range. The concentration of the active ingredients in the formulation is typically 0.1%-50% by weight.

Formula (III') provides a definition of the ammonium salts and phosphonium salts which, according to the invention, boost the activity of crop protection compositions comprising fatty acid biosynthase inhibitors Active ingredients emphasized are especially preferably compounds with the radical combinations for W, X, Y and Z specified in Table 1 and the radical combinations specified for A and B in Table 3.

In the literature it has already been described how the action of various active ingredients can be boosted by addition of ammonium salts. The salts in question, however, are detersive salts (for example WO 95/017817) or salts which have relatively long alkyl substituents and/or aryl substituents and which have a permeabilizing action or which increase the active ingredient's solubility (for example EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Moreover, the prior art describes the action only for particular

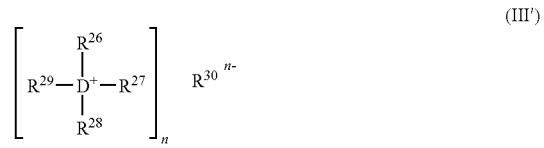

(III')

in which
D is nitrogen or phosphorus,
D is preferably nitrogen,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano, $R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano, $R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl, $R^{26}$, $R^{27}$, $R^{28}$ and $R^{29}$ very particularly preferably represent hydrogen, n is 1, 2, 3 or 4, n is preferably 1 or 2, $R^{30}$ is an organic or inorganic anion, $R^{30}$ is preferably hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate, $R^{30}$ is more preferably lactate, sulphate, nitrate, thiosulphate, thiocyanate, oxalate or formate, $R^{30}$ is most preferably sulphate.

Combinations emphasized in accordance with the invention of active ingredient, salt and penetration enhancer are listed in the table below. "Penetration enhancer as per test" means here that any compound that acts as a penetration enhancer in the cuticle penetration test (Baur et al., 1997, *Pesticide Science* 51, 131-152) is suitable.

The ammonium salts and phosphonium salts of the formula (III') can be used in a broad concentration range to boost the activity of crop protection compositions comprising ketoenols. In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active ingredient concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetration enhancer. It is considered entirely surprising that even in these cases an even greater boost to activity is observed. The present invention therefore likewise provides for the use of a combination of penetration enhancer and ammonium salts and/or phosphonium salts to boost the activity of crop protection compositions which comprise insecticidal and/or acaricidal and/or herbicidal haloalkylmethyleneoxyphenyl-substituted ketoenols of the formula (I) as active ingredient. The invention likewise provides compositions which comprise herbicidal and/or acaricidal and/or insecticidal haloalkylmethyleneoxyphenyl-substituted ketoenols of the formula (I), penetration enhancers and ammonium salts and/or phosphonium salts, including specifically not only formulated active ingredients but also ready-to-use compositions (spray liquors). The invention additionally provides, finally, for the use of these compositions for controlling harmful insects and/or spider mites and/or undesired plant growth.

In the present context, suitable penetration enhancers are all those substances which are usually employed to improve penetration of agrochemically active ingredients into plants. In this context, penetration enhancers are defined in that they penetrate from the aqueous spray liquor and/or the spray coating into the cuticles of the plant, thus increasing the mobility of active ingredients in the cuticles. The method described in the literature (Baur et al., 1997, *Pesticide Science* 51, 131-152) can be used for determining this property.

Examples of useful penetration enhancers include alkanol alkoxylates. Penetration enhancers of the invention are alkanol alkoxylates of the formula (IV')

R—O-(-AO)$_v$—R' (IV')

in which

R is straight-chain or branched alkyl having 4 to 20 carbon atoms,

R' is hydrogen, methyl, ethyl, n-propyl, isopropyl, n-butyl, isobutyl, tert-butyl, n-pentyl or n-hexyl, AO is an ethylene oxide radical, a propylene oxide radical, a butylene oxide radical or is mixtures of ethylene oxide and propylene oxide radicals or butylene oxide radicals, and v is a number from 2 to 30.

One preferred group of penetration enhancers is that of alkanol alkoxylates of the formula

R—O-(-EO—)$_n$—R' (IV'-a)

in which

R is as defined above,

R' is as defined above,

EO is —CH$_2$—CH$_2$—O—, and n is a number from 2 to 20.

A further preferred group of penetration enhancers is that of alkanol alkoxylates of the formula

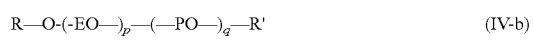
R—O-(-EO—)$_p$—(—PO—)$_q$—R' (IV'-b)

in which

R is as defined above,

R' is as defined above,

EO is —CH$_2$—CH$_2$—O—,

PO is

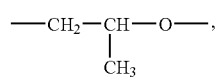
—CH$_2$—CH—O—,
         |
         CH$_3$ p is a number from 1 to 10, and q is a number from 1 to 10.

A further preferred group of penetration enhancers is that of alkanol alkoxylates of the formula

R—O—(—PO—)$_r$-(EO—)$_s$—R' (IV'-c)

in which

R is as defined above,

R' is as defined above,

EO is —CH$_2$—CH$_2$—O—,

PO is

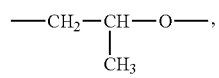
—CH$_2$—CH—O—,
         |
         CH$_3$ r is a number from 1 to 10, and s is a number from 1 to 10.

A further preferred group of penetration enhancers is that of alkanol alkoxylates of the formula

R—O-(-EO—)$_p$—(—BO—)$_q$—R' (IV'-d)

in which
R and R' are as defined above,
EO is —CH$_2$—CH$_2$—O—,
BO is

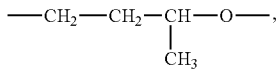

p is a number from 1 to 10 and
q is a number from 1 to 10.

A further preferred group of penetration enhancers is that of alkanol alkoxylates of the formula

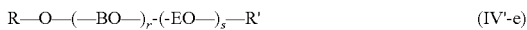 (IV'-e)

in which
R and R' are as defined above,
BO is

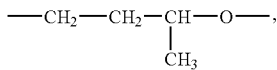

EO is —CH$_2$—CH$_2$—O—,
r is a number from 1 to 10 and
s is a number from 1 to 10.

A further preferred group of penetration enhancers is that of alkanol alkoxylates of the formula

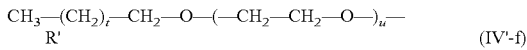 (IV'-f)

in which
R' is as defined above,
t is a number from 8 to 13,
u is a number from 6 to 17.

In the formulae indicated above,
R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

One example of an alkanol alkoxylate of the formula (IV-c) is 2-ethylhexyl alkoxylate of the formula

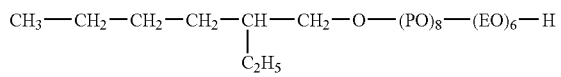 (IV'-c-1)

in which
EO is —CH$_2$—CH$_2$—O—,
PO is

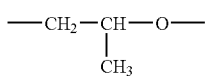

and
the numbers 8 and 6 represent average values.

One example of an alkanol alkoxylate of the formula (IV-d) is the formula

 (IV'-d-1)

in which
EO is CH$_2$—CH$_2$—O—,
BO is

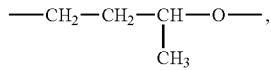

and
the numbers 10, 6 and 2 represent average values.

Particularly preferred alkanol alkoxylates of the formula (IV'-f) are compounds of this formula in which
t is a number from 9 to 12 and
u is a number from 7 to 9.

A very particular preferred alkanol alkoxylate is that of the formula (IV'-f-1)

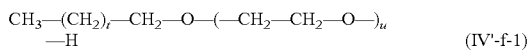 (IV'-f-1)

in which
t is the average value 10.5 and
u is the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetration enhancers also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soya bean oil, or the esters of said oils. Preference is given to rapeseed oil, sunflower oil and their methyl or ethyl esters.

The concentration of penetration enhancer in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and also polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, dyes and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, for example, according to method (A), ethyl N-(2, 6-dimethyl-4-trifluoroethoxyphenyl-acetyl)-1-aminocyclohexanecarboxylate as the starting material, the course of the method according to the invention can be illustrated by the following reaction scheme:

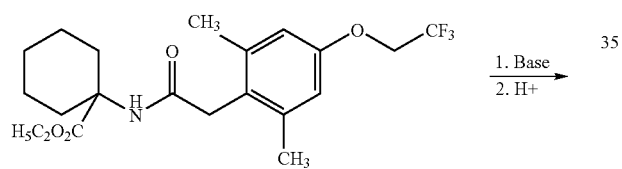

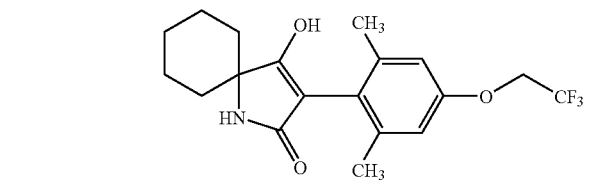

Using, for example, according to method (B), ethyl O-(2, 6-dimethyl-4-trifluoroethoxyphenyl-acetyl)-2-hydroxyisobutyrate, the course of the method according to the invention can be illustrated by the following reaction scheme:

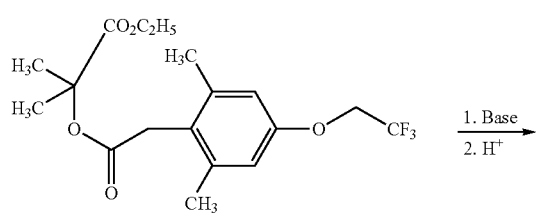

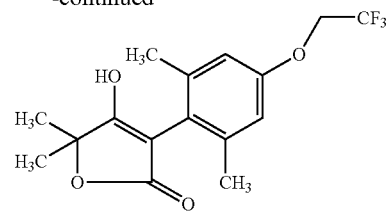

Using, for example, according to method (C), ethyl 2-(2, 6-dimethyl-4-trifluoroethoxyphenyl)-4-(4-methoxy)benzylmercapto-4-methyl-3-oxovalerate, the course of the method according to the invention can be illustrated by the following reaction scheme:

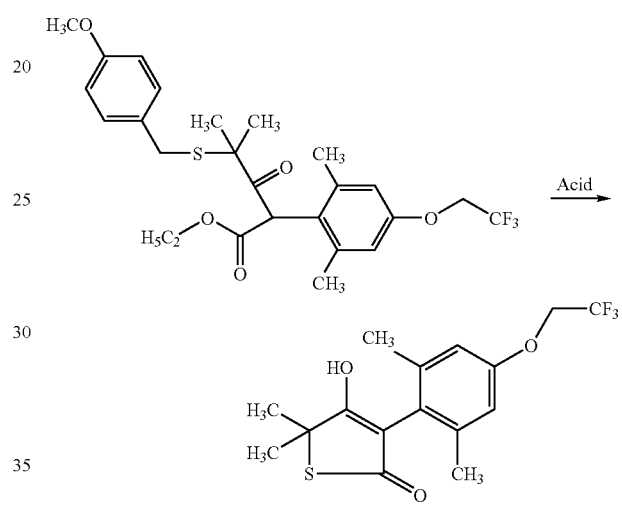

Using, for example, according to method (D), chlorocarbonyl 2,6-dimethyl-4-trifluoroethoxyphenyl ketene and acetone as starting compounds, the course of the method according to the invention can be illustrated by the following reaction scheme:

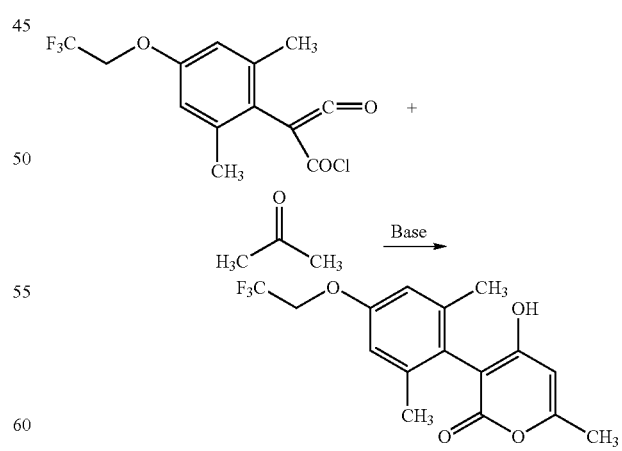

Using, for example, according to method (E), chlorocarbonyl 2,6-dimethyl-4-trifluoroethoxyphenyl ketene and thiobenzamide as starting compounds, the course of the method according to the invention can be illustrated by the following reaction scheme:

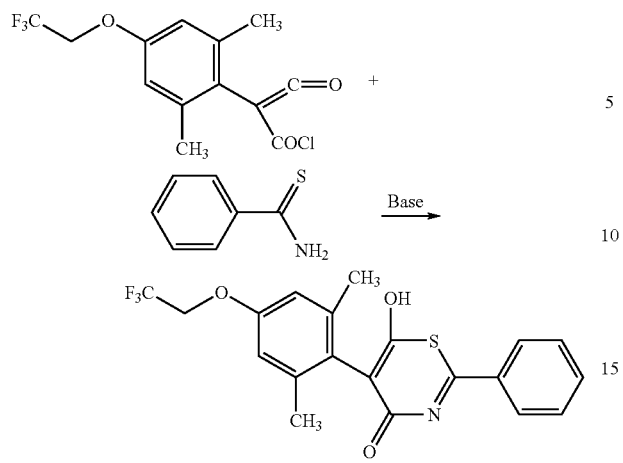

Using, for example, according to method (F), ethyl 5-(2,6-dimethyl-4-trifluoroethoxyphenyl)-2,3-trimethylene-4-oxovalerate, the course of the method according to the invention can be illustrated by the following reaction scheme:

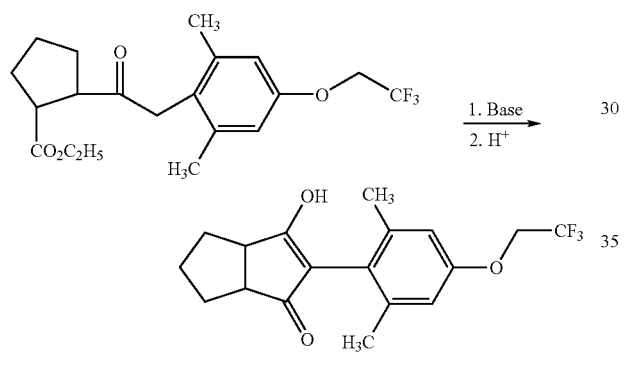

Using, for example, according to method (G), ethyl 6-[(2,6-dimethyl-4-trifluoroethoxy)phenyl]-2-dimethyl-5-oxo-hexanoate, the course of the method according to the invention can be illustrated by the following reaction scheme:

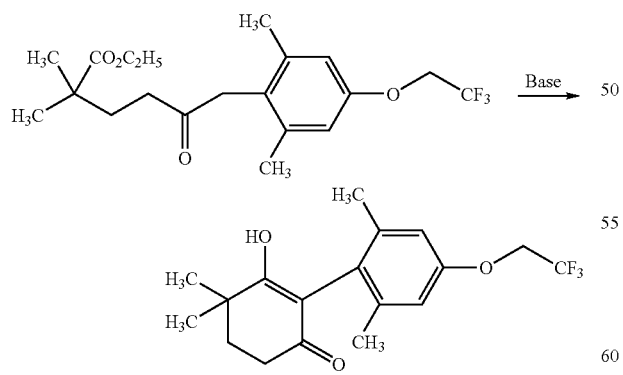

Using, for example, according to method (Hα), hexahydropyridazine and chlorocarbonyl 2,6-dimethyl-4-trifluoroethoxyphenyl ketene as starting compounds, the course of reaction in the method according to the invention can be illustrated by the following reaction scheme:

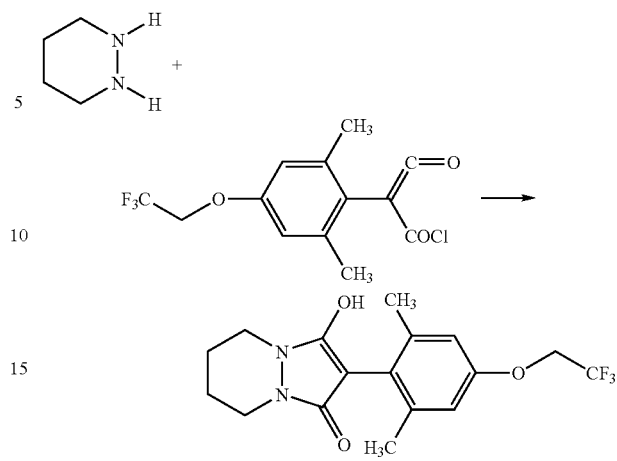

Using, for example, according to method (Hβ), hexahydropyridazine and dimethyl 2-(2,6-dimethyl-4-trifluoroethoxy)phenylmalonate as starting materials, the course of the method according to the invention can be illustrated by the following reaction scheme:

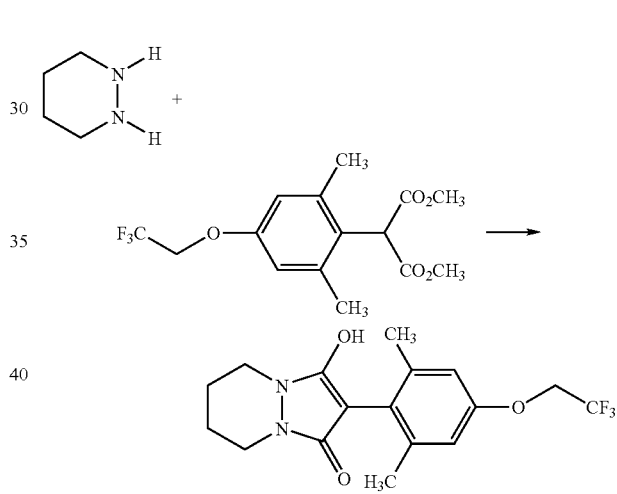

Using, for example, according to method (Hγ), 1-ethoxycarbonyl-2-[(2,6-dimethyl-4-trifluoroethoxy)phenylacetyl]hexahydropyridazine as the starting material, the course of reaction can be illustrated by the following scheme:

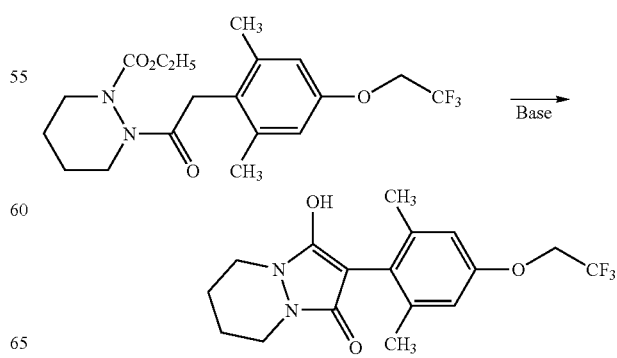

Using, for example, according to method (I), ethyl N-(2,6-dimethyl-4-trifluoroethoxyphenyl-acetyl)-1-aminomethyl-cyclohexanecarboxylate as the starting material, the course of the method according to the invention can be illustrated by the following reaction scheme:

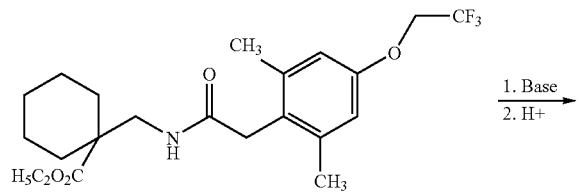

Using, for example, according to method (J), ethyl O-(2,6-dimethyl-4-trifluoroethoxyphenylacetyl)-3-hydroxy-2,2-dimethylpropionate, the course of the method according to the invention can be illustrated by the following reaction scheme:

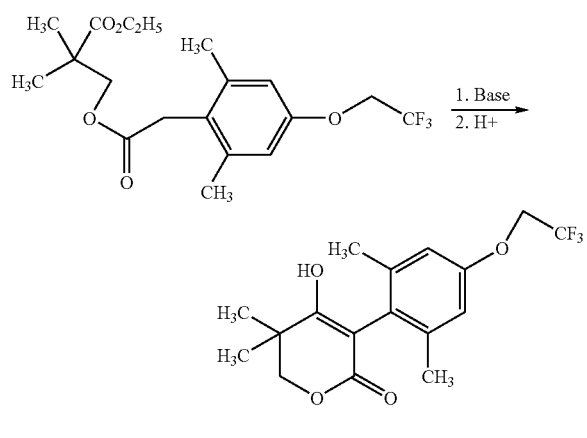

Using, according to method (K), ethyl N-methyl-N-[(2,6-dimethyl-4-trifluoroethoxy)phenylacetyl]-1-aminooxycyclopentanecarboxylate as the starting material, the course of the method according to the invention can be illustrated by the following reaction scheme:

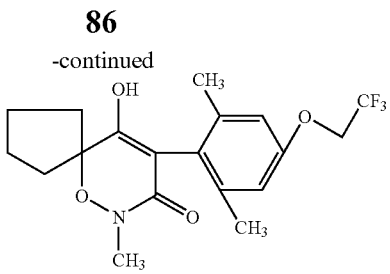

Using, for example, according to method (Lα), 3-(2-methyl-4-trifluoroethoxy-6-ethylphenyl)-5,5-dimethylpyrrolidine-2,4-dione and pivaloyl chloride as starting materials, the course of the method according to the invention can be illustrated by the following reaction scheme:

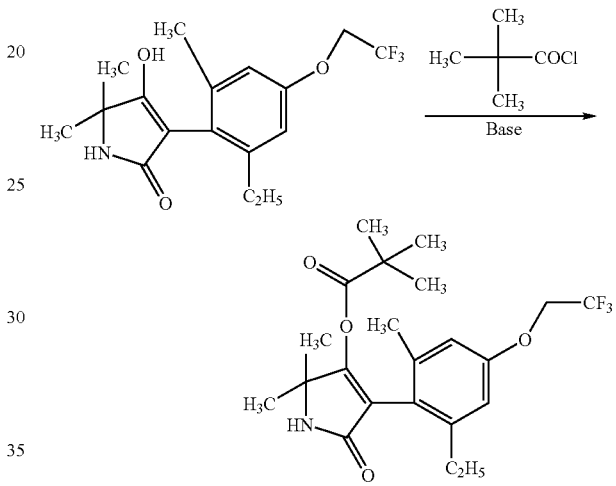

Using, for example, according to method (Lβ), 3-(2,6-dimethyl-4-trifluoroethoxyphenyl)-5,5-dimethylpyrrolidine-2,4-dione and acetic anhydride as starting compounds, the course of the method according to the invention can be illustrated by the following reaction scheme:

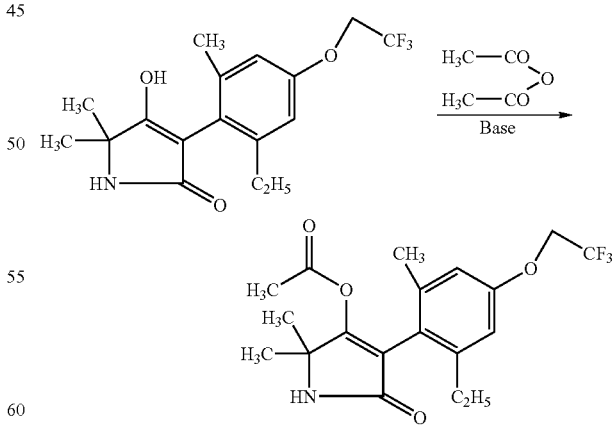

Using, for example, according to method (M), 8-[(2,6-dimethyl-4-trifluoroethoxy)phenyl]-1-azabicyclo[4.3.0$^{1.6}$]nonane-7,9-dione and ethyl chloroformate as starting compounds, the course of the method according to the invention can be illustrated by the following reaction scheme:

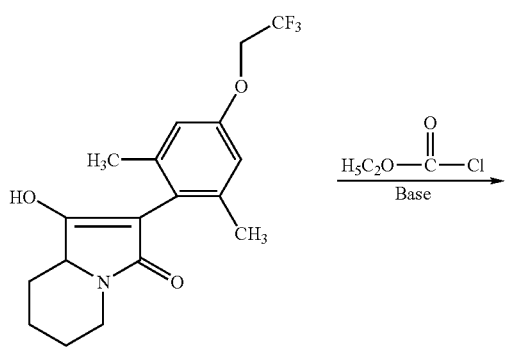

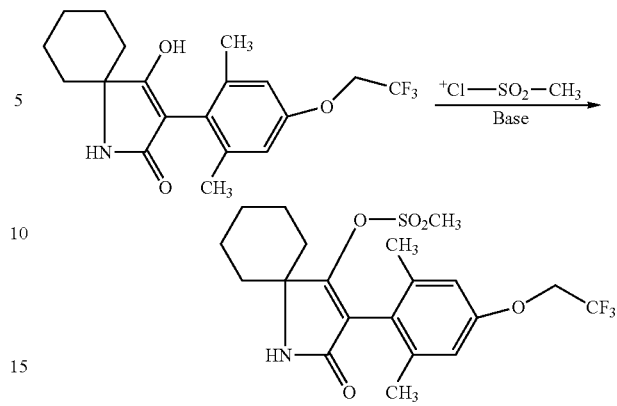

Using, for example, according to method (N), 3-(2,6-dimethyl-4-trifluoroethoxyphenyl)-4-hydroxy-5-methyl-6-(phenyl)pyrone and methyl chloromonothioformate as starting materials, the course of reaction can be illustrated as follows:

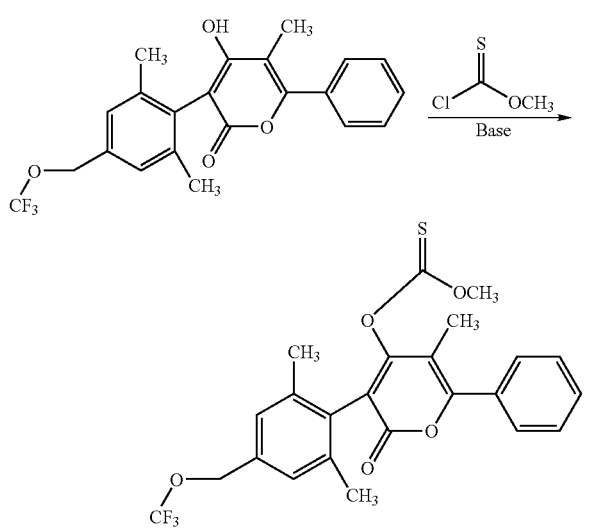

Using, for example, according to method (O), 3-(2,6-dimethyl-4-trifluoroethoxyphenyl)-5,5-penta-methylenepyrrolidine-2,4-dione and methanesulphonyl chloride as starting materials, the course of reaction can be illustrated by the following reaction scheme:

Using, for example, according to method (P), 3-(2,6-dimethyl-4-trifluoroethoxyphenyl)-4-hydroxy-5,5-dimethylpyrrolidine-2,4-dione and 2,2,2-trifluoroethyl methanethiophosphonyl chloride as starting materials, the course of reaction can be illustrated by the following reaction scheme:

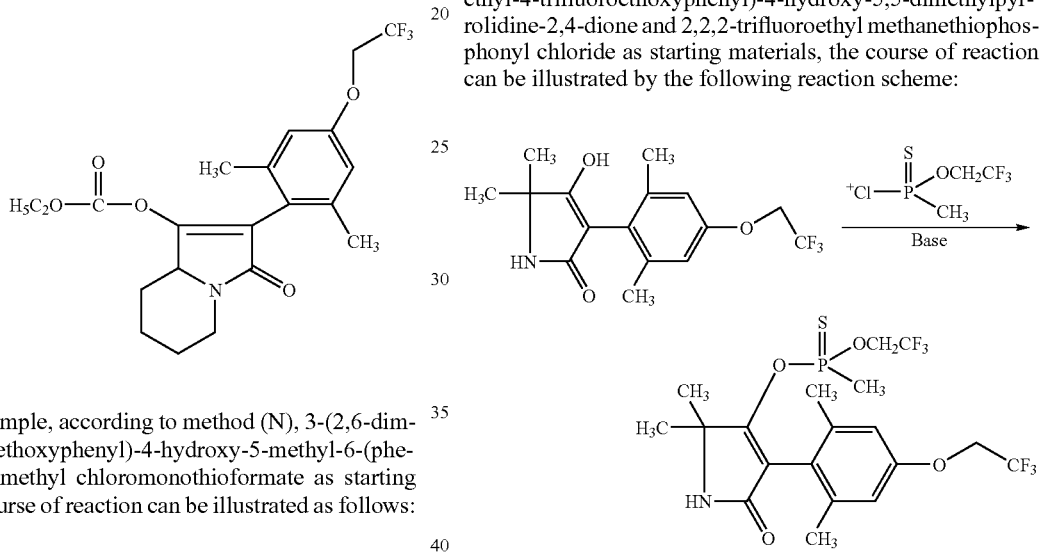

Using, for example, according to method (O), 3-(2-ethyl-4-trifluoroethoxy-6-methylphenyl]-5-cyclopropyl-5-methylpyrrolidine-2,4-dione and NaOH as components, the course of the method according to the invention can be illustrated by the following reaction scheme:

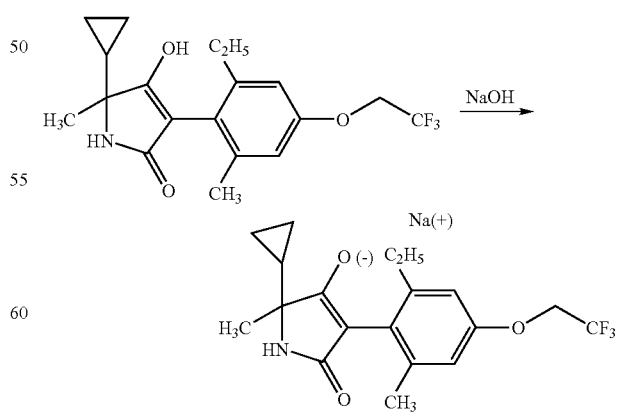

Using, for example, according to method (R) variant α, 3-(2,6-dimethyl-4-trifluoroethoxyphenyl)-4-hydroxy-5,5- tetramethylene-Δ³-dihydrofuran-2-one and ethyl isocyanate as starting materials, the course of reaction can be illustrated by the following reaction scheme:

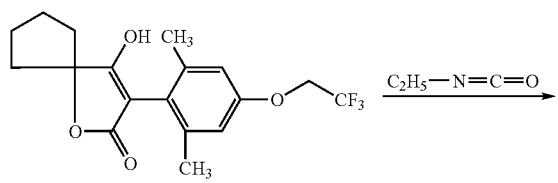

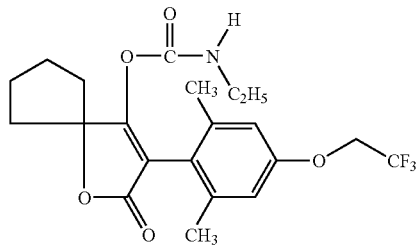

Using, for example, according to method (R) variant β, 3-(2-methyl-4-trifluoroethoxy-6-ethylphenyl)-5-methylpyr-rolidine-2,4-dione and dimethylcarbamyl chloride as starting materials, the course of reaction can be illustrated by the following scheme:

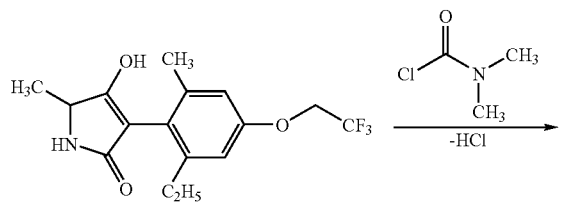

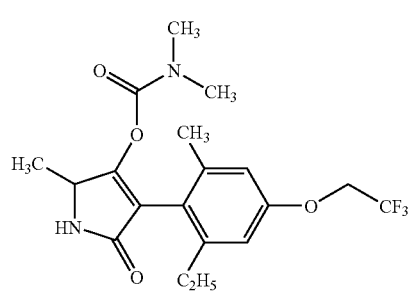

Using, for example, according to method (S), 3-(4-bro-mine-2,6-dimethylphenyl)-5,5-di-methylpyrrolidine-2,4-di-one and trifluoroethanol as starting materials, the course of reaction can be illustrated by the following scheme:

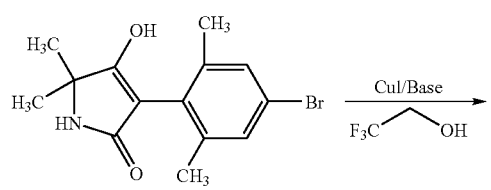

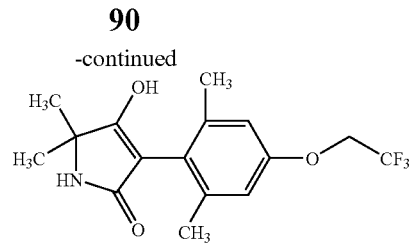

The compounds of the formula (II) required as starting materials in the process according to the invention (a)

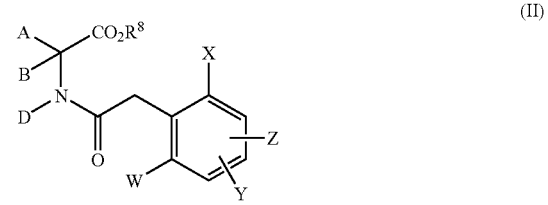

in which

A, B, D, W X, Y, Z and $R^8$ are each as defined above, are novel.

The acylamino acid esters of the formula (II) are obtained, for example, when amino acid derivatives of the formula (XXVII)

in which

A, B, $R^8$ and D are each as defined above, are acylated with substituted phenylacetic acid derivatives of the formula (XXVIII)

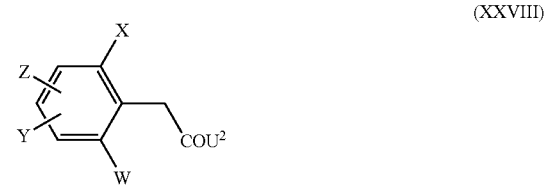

in which

W, X, Y and Z are each as defined above and $U^2$ is a leaving group introduced by carboxylic acid activating reagents such as carbonyldiimidazole, carbonyldiimides (for example dicyclohexylcarbodiimide), phosphorylating reagents (for example $POCl_3$, BOP—Cl), halogenating agents, e.g. thionyl chloride, oxalyl chloride, phosgene or chloroformic esters, (Chem. Reviews 52, 237-416 (1953); Bhattacharya, Indian J. Chem. 6, 341-5, 1968)

or when acylamino acids of the formula (XXIX)

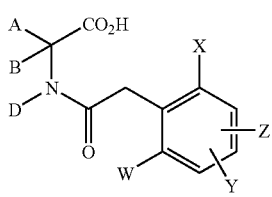

(XXIX)

in which
A, B, D, W, X, Y and Z are each as defined above,
are esterified (Chem. Ind. (London) 1568 (1968)).

The compounds of the formula (XXIX)

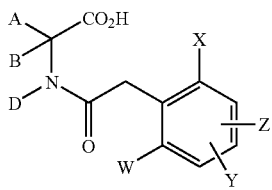

(XXIX)

in which
A, B, D, W, X, Y and Z are each as defined above
are novel.

The compounds of the formula (XXIX) are obtained when amino acids of the formula (XXX)

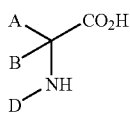

(XXX)

in which
A, B and D are each as defined above,
are acylated with substituted phenylacetic acid derivatives of the formula (XXVIII)

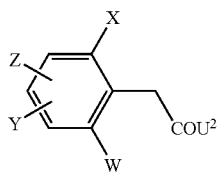

(XXVIII)

in which
W, X, Y and Z are each as defined above and
$U^2$ is as defined above,
for example according to Schotten-Baumann (Organikum, VEB Deutscher Verlag der Wissen-schaften, Berlin 1977, p. 505).

The compounds of the formula (XXVIII) are novel. They can be prepared by processes known in principle (see, for example, H. Henecka, Houben-Weyl, Methoden der Organischen Chemie, Vol. 8, p. 467-469 (1952) WO 97/02243, WO 99/43699), or are obtained in situ with the above-specified reagents.

The compounds of the formula (XXVIII) are obtained, for example, by reacting substituted phenylacetic acids of the formula (XXXI)

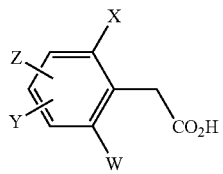

(XXXI)

in which
W, X, Y and Z are each as defined above,
with halogenating agents (e.g. thionyl chloride, thionyl bromide, oxalyl chloride, phosgene, phosphorus trichloride, phosphorus tribromide or phosphorus pentachloride), phosphonylating reagents (for example $POCl_3$, BOP—Cl), carbonyldiimidazole, carbonyldiimides (e.g. dicyclohexylcarbonyldiimide), optionally in the presence of a diluent (for example optionally chlorinated aliphatic or aromatic hydrocarbons such as toluene or methylene chloride or ethers, e.g. tetrahydrofuran, dioxane, methyl tert-butyl ether) at temperatures of −20° C. to 150° C., preferably of −10° C. to 100° C.

Some of the compounds of the formula (XXVII) and (XXX) are known from the patent literature cited at the outset and/or can be prepared by known processes (see, for example, Compagnon, Miocque Ann. Chim. (Paris) [14] 5, p. 11-22, 23-27 (1970)).

The substituted cyclic amino carboxylic acids of the formula (XXX) in which A and B form a ring are generally obtainable by the Bucherer-Bergs synthesis or by the Strecker synthesis and are obtained in different isomeric forms in each case. Thus, under the conditions of the Bucherer-Bergs synthesis, predominantly the isomers (for the sake of simplicity referred to hereinafter as β) in which the R radicals and the carboxyl group are in equatorial positions are obtained, whereas, under the conditions of the Strecker synthesis, predominantly the isomers (for the sake of simplicity, referred to hereinafter as α) in which the amino group and the R radicals are in equatorial positions are obtained.

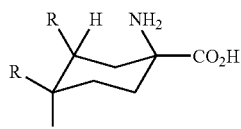 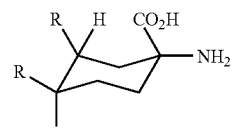

Bucherer-Bergs synthesis (β isomer)   Strecker synthesis (α isomer)

(L. Munday, J. Chem. Soc. 4372 (1961); J. T. Eward, C. Jitrangeri, Can. J. Chem. 53, 3339 (1975).

In addition, the starting materials of the formula (II) used in the above method (A)

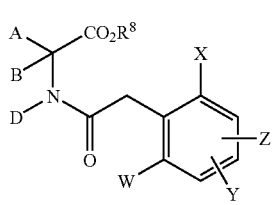

(II)

in which

A, B, D, W, X, Y, Z and R⁸ are each as defined above, can be prepared when aminonitriles of the formula (XXXII)

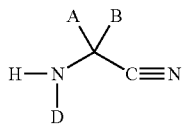
(XXXII)

in which

A, B and D are each as defined above, are reacted with substituted phenylacetic acid derivatives of the formula (XXVIII)

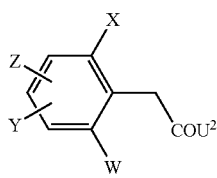
(XXVIII)

in which

W, X, Y, Z and $U^2$ are each as defined above, to give compounds of the formula (XXXIII))

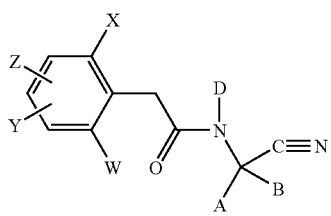
(XXXIII)

in which

A, B, D, W, X, Y and Z are each as defined above, and the latter are subsequently subjected to an acidic alcoholysis.

The compounds of the formula (XXXIII) are likewise novel.

The compounds of the formula (III) required as starting materials in the method (B) according to the invention

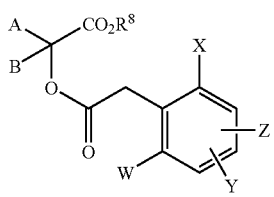
(III)

in which

A, B, W, X, Y, Z and W are each as defined above, are novel.

They can be prepared by methods known in principle.

For example, the compounds of the formula (III) are obtained when 2-hydroxycarboxylic esters of the formula (XXXIV-A)

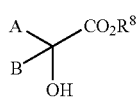
(XXXIV-A)

in which

A, B and $R^8$ are each as defined above, are acylated with substituted phenylacetic acid derivatives of the formula (XXVIII)

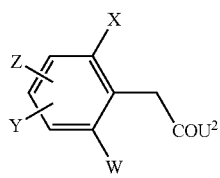
(XXVIII)

in which

W, X, Y, Z and $U^2$ are each as defined above, (Chem. Reviews 52, 237-416 (1953)).

In addition, compounds of the formula (HI) are obtained when substituted phenylacetic acids of the formula (XXXI)

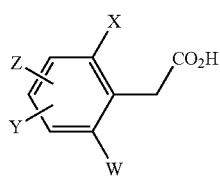
(XXXI)

in which

W, X, Y and Z are each as defined above, are alkylated with α-halocarboxylic esters of the formula (XXXIV-B)

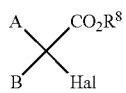
(XXXIV-B)

in which

A, B and $R^8$ are each as defined above and

Hal is chlorine or bromine.

Some of the compounds of the formula (XXXIV-A) are commercially available or known from the disclosures mentioned at the outset.

The compounds of the formula (XXXIV-B) are commercially available.

The compounds of the formula (XXXI) are novel.

For example, the compounds of the formula (XXXI) are obtained

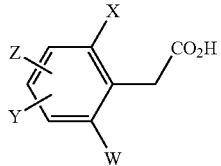
(XXXI)

in which
W, X, Y and Z are each as defined above,
when phenylacetic esters of the formula (XXXV)

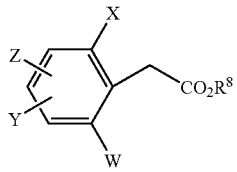
(XXXV)

in which
W, X, Y, Z and are each as defined above,
are hydrolysed in the presence of acids or bases, in the presence of a solvent, under commonly known standard conditions.

The compounds of the formula (XXXV) are novel.
The compounds of the formula (XXXV)

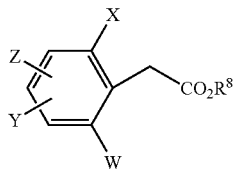
(XXXV)

in which
W, X, Y, Z and $R^8$ are each as defined above,
are obtained by the method analogous to method (S) described in the examples,
when phenylacetic esters of the formula (XXXV-a)

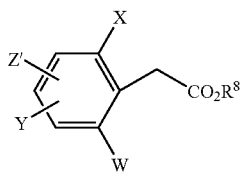
(XXXV-a)

in which
$R^8$, W, X and Y are each as defined above
and Z' is bromine or iodine,
are converted in the presence of haloalkyl alcohols (e.g. trifluoroethanol, in the presence of a base and optionally in the presence of a copper salt (preferably Cu(I)I).

The phenylacetic esters of the formula (XXXV-a) are known in principle, for example, from publications WO 96/35 664, WO 97/02243, WO 97/01535, WO 98/05638 and DE-A-10 301 804, and can be prepared by the processes described there.

The compounds of the formula (IV) required as starting materials in the above method (C)

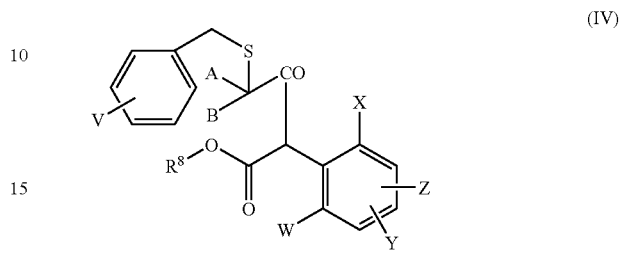
(IV)

in which
A, B, V, W, X, Y, Z and $R^8$ are each as defined above, are novel.

They can be prepared by methods known in principle.

The compounds of the formula (IV) are obtained, for example, when substituted phenylacetic esters of the formula (XXXV)

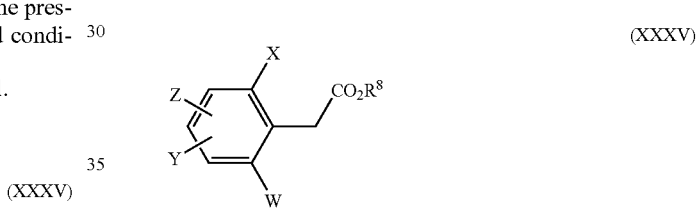
(XXXV)

in which
W, X, Y, Z and $R^8$ are each as defined above,
are acylated with 2-benzylthiocarbonyl halides of the formula (XXXVI)

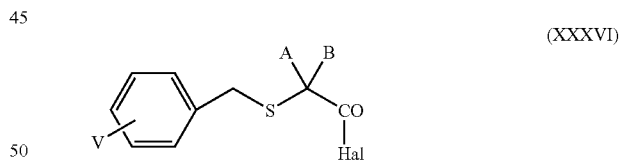
(XXXVI)

in which
A, B and V are each as defined above and
Hal is halogen (especially chlorine or bromine),
in the presence of strong bases (see, for example, M. S. Chambers, E. J. Thomas, D. J. Williams, J. Chem. Soc. Chem. Commun., (1987), 1228).

Some of the benzylthiocarbonyl halides of the formula (XXXVI) are known and/or can be prepared by known processes (J. Antibiotics (1983), 26, 1589).

The halocarbonyl ketenes of the formula (VI) required as starting materials in the above methods (D), (E) and (H-α) are novel. They can be prepared by methods known in principle (cf., for example, Org. Prep. Proced. Int., 7, (4), 155-158, 1975 and DE 1 945 703). For example, the compounds of the formula (VI)

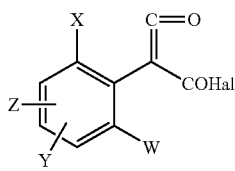

(VI)

in which
W, X, Y and Z are each as defined above and
Hal is chlorine or bromine
are obtained when
substituted phenylmalonic acids of the formula (XXXVII)

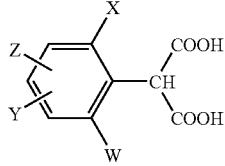

(XXXVII)

in which
W, X, Y and Z are each as defined above,
are reacted with acid halides, for example thionyl chloride, phosphorus(V) chloride, phosphorus(III) chloride, oxalyl chloride, phosgene or thionyl bromide, optionally in the presence of catalysts, for example dimethylformamide, methylstearylformamide or triphenylphosphine, and optionally in the presence of bases, for example pyridine or triethylamine.

The substituted phenylmalonic acids of the formula (XXXVII) are novel. They can be prepared in a simple manner by known processes (cf., for example, Organikum, VEB Deutscher Verlag der Wissenschaften, Berlin 1977, p. 517 ff, EP-A-528 156, WO 96/35 664, WO 97/02 243, WO 97/01535, WO 97/36868 and WO 98/05638).

For instance, phenylmalonic acids of the formula (XXXVII)

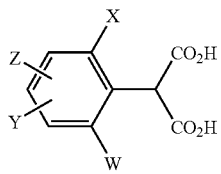

(XXXVII)

in which
W, X, Y and Z are each as defined above,
are obtained when phenylmalonic esters of the formula (XI)

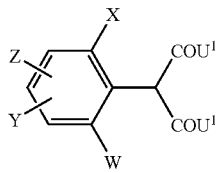

(XI)

in which
W, X, Y and Z are each as defined above,
and U' is $OR^8$,
where $R^8$ is as defined above,
are first hydrolysed in the presence of a base and a solvent and then acidified cautiously (see, for example, EP-A-528 156, WO 96/35 664, WO 97/02 243).

The malonic esters of the formula (XI)

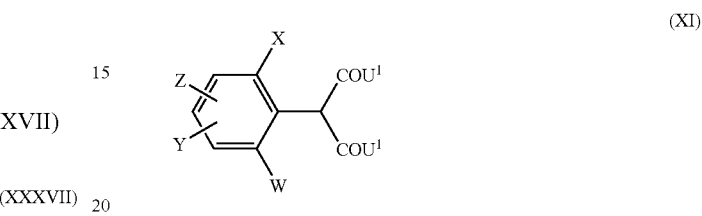

(XI)

in which
W, X, Y and Z are each as defined above,
and $U^1$ is $OR^8$,
where $R^8$ is as defined above
are novel.

They can be prepared by commonly known methods of organic chemistry (cf., for example, Tetrahedron Lett. 27, 2763 (1986), Organikum VEB Deutscher Verlag der Wissenschaften, Berlin 1977, p. 587 ff., WO 96/35664, WO 97/02243, WO 97/01535, WO 97/36868, WO 98/05638 and WO 99/47525).

The carbonyl compounds of the formula (V) required as starting materials for the method (D) according to the invention

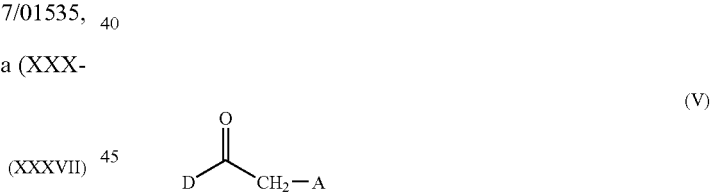

(V)

in which
A and D are each as defined above,
or the silyl enol ethers thereof, of the formula (Va)

(Va)

in which
A, D and $R^8$ are each as defined above,
are commercially available, commonly known compounds, or compounds obtainable by known processes.

The principle of preparation of the ketenyl chlorides of the formula (VI) required as starting materials to perform the method (E) according to the invention has already been described in connection with method D. The thioamides of the formula (VII) required to perform the method (E) according to the invention

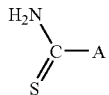
(VII)

in which
A is as defined above,
are compounds which are common knowledge in organic chemistry.

The compounds of the formula (VIII) required as starting materials in the above method (F)

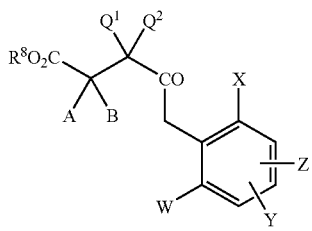
(VIII)

in which
A, B, $Q^1$, $Q^2$, W, X, Y, Z and $R^8$ are each as defined above, are novel.

They can be prepared by methods known in principle.

The 5-aryl-4-ketocarboxylic esters of the formula (VIII) are obtained, for example, when 5-aryl-4-ketocarboxylic acids of the formula (XXXVIII)

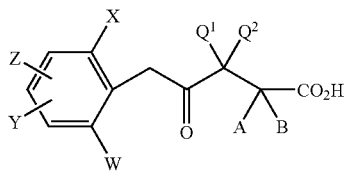
(XXXVIII)

in which
W, X, Y, Z, A, B, $Q^1$ and $Q^2$ are each as defined above,
are esterified (cf., for example, Organikum, 15th edition, Berlin, 1977, page 499) or alkylated (see preparation example).

The 5-aryl-4-ketocarboxylic acids of the formula (XXX-VIII)

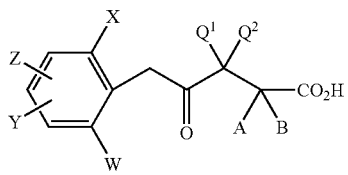
(XXXVIII)

in which
A, B, $Q^1$, $Q^2$, W, X, Y and Z are each as defined above,
are novel, but can be prepared by methods known in principle (WO 96/01 798, WO 97/14667, WO 98/39281).

The 5-aryl-4-ketocarboxylic acids of the formula (XXX-VIII) are obtained, for example, when 2-phenyl-3-oxoadipic esters of the formula (XXXIX)

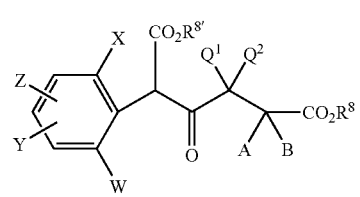
(XXXIX)

in which
A, B, $Q^1$, $Q^2$, W, X, Y and Z are each as defined above and
$R^8$ and $R^{8'}$ are each alkyl (especially $C_1$-$C_8$-alkyl) and
when the compound of the formula (XLI-a) is used, $R^8$ is hydrogen,
are decarboxylated, optionally in the presence of a diluent and optionally in the presence of a base or acid (cf., for example, Organikum, 15th edition, Berlin, 1977, page 519 to 521, WO 96/01798, WO 97/14667, WO 98/39281).

The compounds of the formula (XXXIX)

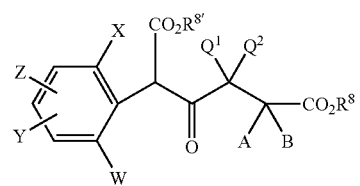
(XXXIX)

in which
A, B, $Q^1$, $Q^2$, W, X, Y, Z, $R^8$ and $R^{8'}$ are each as defined above and
when the compound of the formula (XLI-a) is used, $R^8$ is hydrogen,
are novel.

The compounds of the formula (XXXIX) are obtained, for example,
when dicarboxylic monoester chlorides of the formula (XL)

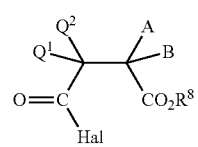
(XL)

in which

A, B, $Q^1$, $Q^2$ and $R^8$ are each as defined above and

Hal is chlorine or bromine, or carboxylic anhydrides of the formula (XLI-a)

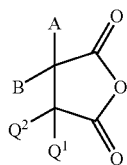
(XLI-a)

in which

A, B, $Q^1$ and $Q^2$ are each as defined above, are acylated with a phenylacetic ester of the formula (XXXV)

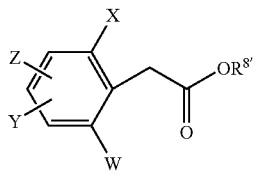
(XXXV)

in which

W, X, Y, Z and $R^8$ are each as defined above, in the presence of a diluent and in the presence of a base (cf., for example, M. S. Chambers, E. J. Thomas, D. J. Williams, J. Chem. Soc. Chem. Commun., (1987), 1228; cf. also the preparation examples).

Some of the compounds of the formulae (XL) and (XLI-a) are known compounds in organic chemistry and/or can be prepared in a simple manner by methods known in principle.

The compounds of the formula (IX) required as starting materials in the above method (G)

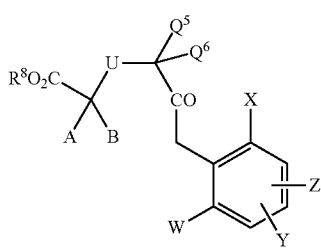
(IX)

in which

A, B, $Q^5$, $Q^6$, U, W, X, Y, Z and $R^8$ are each as defined above, are novel.

They can be prepared by methods known in principle.

6-aryl-5-ketocarboxylic esters of the formula (IX) are obtained, for example, when 6-aryl-5-ketocarboxylic acids of the formula (XLII)

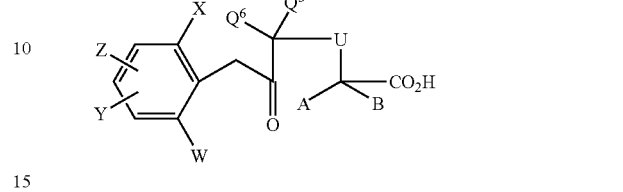
(XLII)

in which

A, B, $Q^5$, $Q^6$, U, W, X, Y and Z are each as defined above, are esterified (cf., for example, Organikum, 15th edition, Berlin, 1977, page 499, WO 99/43649, WO 99/48869).

The 6-aryl-5-ketocarboxylic acids of the formula (XLII)

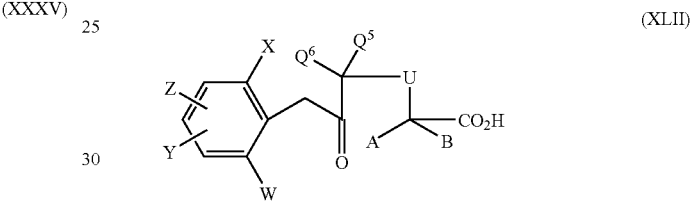
(XLII)

in which

A, B, $Q^5$, $Q^6$, U, W, X, Y and Z are each as defined above, are novel. They can be prepared by methods known in principle (WO 99/43649, WO 99/48869), for example when substituted 2-phenyl-3-oxoheptanedioic esters of the formula (XLIII)

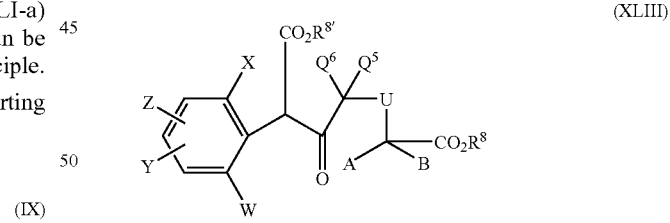
(XLIII)

in which

A, B, $Q^5$, $Q^6$, U, W, X and Z are each as defined above and $R^8$ and $R^{8'}$ are each alkyl (preferably $C_1$-$C_6$-alkyl), and, when the compound of the formula (XLI-b) is used, $R^8$ is hydrogen, are hydrolysed and decarboxylated, optionally in the presence of a diluent and optionally in the presence of a base or acid (cf., for example, Organikum, 15th edition, Berlin, 1977, page 519 to 521, WO 99/43649, WO 99/48869).

The compounds of the formula (XLIII)

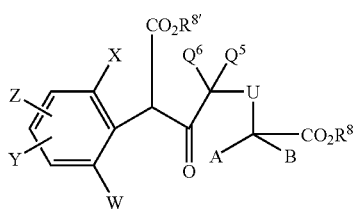

(XLIII)

in which
A, B, $Q^5$, $Q^6$, U, W, X, Y, Z, $R^8$ and $R^{8'}$ are each as defined above,
are novel and are obtainable,
when dicarboxylic esters of the formula (XLIV)

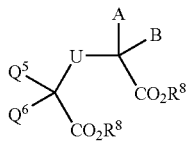

(XLIV)

in which
A, B, $Q^5$, $Q^6$, U and $R^8$ are each as defined above,
or carboxylic anhydrides of the formula (XLI-b)

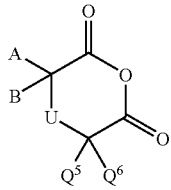

(XLI-b)

in which A, B, $Q^5$, $Q^6$ and U are each as defined above are condensed with a substituted phenylacetic ester of the formula (XXXV)

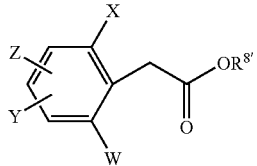

(XXXV)

in which
W, X, Y, Z and R' are each as defined above,
in the presence of a diluent and in the presence of a base.

Some of the compounds of the formula (XLIV) are known and/or can be prepared by known processes.

Some of the hydrazines of the formula (X) required as starting materials for the method (H-α) and (H-β) according to the invention

A—NH—NH—D (X)

in which
A and D are each as defined above,
are known and/or preparable by literature methods (cf., for example, Liebigs Ann. Chem. 585, 6 (1954); Reaktionen der organischen Synthese, C. Ferri, page 212, 513; Georg Thieme Verlag Stuttgart, 1978; Liebigs Ann. Chem. 443, 242 (1925); Chem. Ber. 98, 2551 (1965), EP-A-508 126, WO 92/16510, WO 99/47 525, WO 01/17 972).

The compounds of the formula (XII) required for the method (H-γ) according to the invention

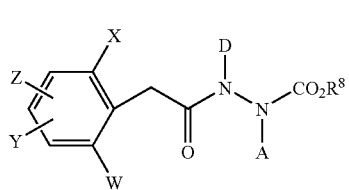

(XII)

in which
A, D, W, X, Y, Z and $R^8$ are each as defined above,
are novel.

The acyl carbazates of the formula (XII) are obtained, for example, when carbazates of the formula (XLV)

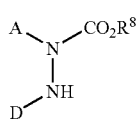

(XLV)

in which
A, $R^8$ and D are each as defined above,
are acylated with substituted phenylacetic acid derivatives of the formula (XXVIII)

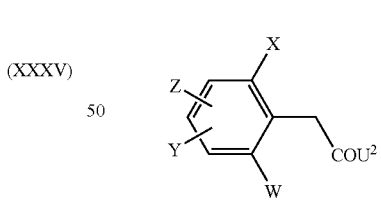

(XXVIII)

in which
W, X, Y, Z, and $U^2$ are each as defined above (Chem. Reviews 52, 237-416 (1953); Bhattacharya, Indian J. Chem. 6, 341-5, 1968).

Some of the carbazates of the formula (XLV) are commercially available and some are known compounds or can be, prepared by methods of organic chemistry known in principle.

The compounds of the formula (XXVIII) have already been described for the precursors for methods (A) and (B).

The compounds of the formula (XIII) required as starting materials in the method (I) according to the invention

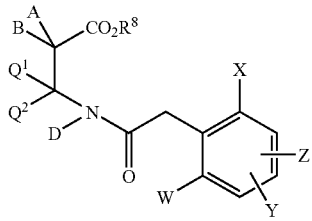
(XIII)

in which

A, B, D, $Q^1$, $Q^2$, W, X, Y, Z and $R^8$ are each as defined above are novel.

The acylamino acid esters of the formula (XIII) are obtained, for example, when amino acid derivatives of the formula (XLVI)

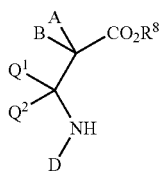
(XLVI)

in which

A, B, $Q^1$, $Q^2$, $R^8$ and D are each as defined above, are acylated with substituted hetarylacetic acid derivatives of the formula (XXVIII)

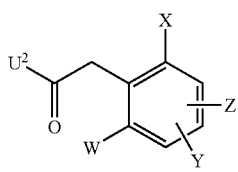
(XXVIII)

in which

W, X, Y, Z and $U^2$ are each as defined above (Chem. Reviews 52, 237-416 (1953); Bhattacharya, Indian J. Chem. 6, 341-5, 1968)

or when acylamino acids of the formula (XLVII)

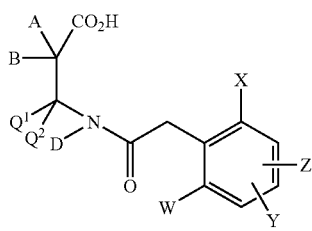
(XLVII)

in which

A, B, D, $Q^1$, $Q^2$, W, X, Y and Z are each as defined above, are esterified (Chem. Ind. (London) 1568 (1968)).

The compounds of the formula (XLVII)

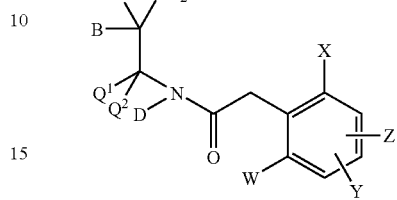
(XLVII)

in which

A, B, D, $Q^1$, $Q^2$, W, X, Y and Z are each as defined above, are novel.

The compounds of the formula (XLVII) are obtained when β-amino acids of the formula (XLVIII)

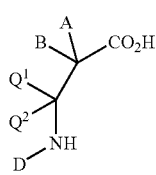
(XLVIII)

in which

A, B, $Q^1$, $Q^2$ and D are each as defined above, are acylated with substituted phenylacetic acid derivatives of the formula (XXVIII)

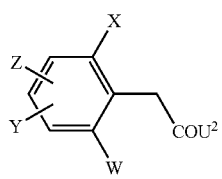
(XXVIII)

in which

W, X, Y, Z and $U^2$ are each as defined above, for example according to Schotten-Baumann (Organikum, VEB Deutscher Verlag der Wissen-schaften, Berlin 1977, p. 505).

Some of the compounds of the formulae (XLVI) and (XLVIII) are known from WO 01/79204 or can be prepared by the method known in principle specified there.

The compounds of the formula (XIV) required as starting materials in the method (J) according to the invention

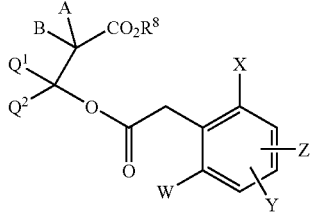

(XIV)

in which
A, B, Q$^1$, Q$^2$, W, X, Y, Z and R$^8$ are each as defined above,
are novel.

The acylhydroxycarboxylic esters of the formula (XIV) are obtained, for example, when hydroxycarboxylic esters of the formula (XLIX)

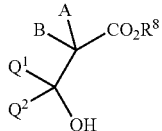

(XLIX)

in which
A, B, Q$^1$, Q$^2$ and R$^8$ are each as defined above,
are acylated with substituted phenylacetic acid derivatives of the formula (XXVIII)

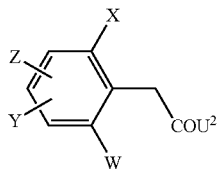

(XXVIII)

in which
W, X, Y, Z and U$^2$ are each as defined above
(see preparation examples of the formula (II)).

Some of the compounds of the formula (XLIX) are known from WO 01/98288 or can be prepared by methods known in principle, for example by Reformatsky synthesis (Organikum, VEB Deutscher Verlag der Wissenschaften, Berlin 1990, 18th ed. p. 501 ff.)

The compounds of the formula (XV) required as starting materials in the method (K) according to the invention

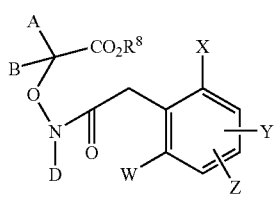

(XV)

in which
A, B, D, W, X, Y, Z and R$^8$ are each as defined above,
are novel.

The acylhydroxylamino acid esters of the formula (XV) are obtained, for example, when amino acid derivatives of the formula (L)

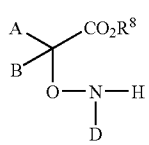

(L)

in which
A, B, R$^8$ and D are each as defined above,
are acylated with substituted phenylacetic acid derivatives of the formula (XXVIII)

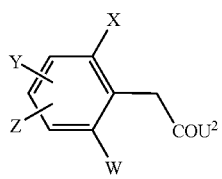

(XXVIII)

in which
W, X, Y, Z and U$^2$ are each as defined above
(Chem. Reviews 52, 237-416 (1953); Bhattacharya, Indian J. Chem. 6, 341-5, 1968).

Some of the hydroxylamino acid esters of the formula (L) required as starting materials to prepare compounds of the formula (H)

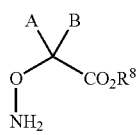

(L)

in which
A, B and R$^8$ are each as defined above are novel and can be prepared by known processes (N. A. Porter et. al. J. Org. Chem. 63 5547 (1998), WO 03/048138).

For example, hydroxylamino acid esters of the formula (L)

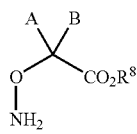

(L)

in which

A, B and $R^8$ are each as defined above are obtained when N-hydroxyphthalimide of the formula (LI)

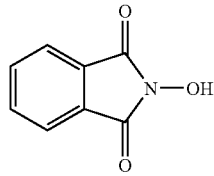

(LI)

is reacted with haloalkyl esters of the formula (LII)

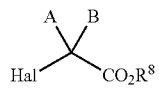

(LII)

in which

A, B and $R^8$ are each as defined above and

Hal is chlorine, bromine or iodine, preferably bromine, to give O-alkoxyphthalimides of the formula (LIII),

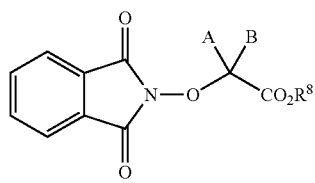

(LIII)

in which

A, B and $R^8$ are each as defined above, and then the compounds of the formula (L) are released, for example by hydrazinolysis.

The compounds of the formula (LII) and (LI) are likewise known and can be prepared by known processes (N. A. Porter et. al. J. Org. Chem. 63, 5547-5554, 1998).

In addition, for example, acylhydroxylamino acid esters of the formula (XV)

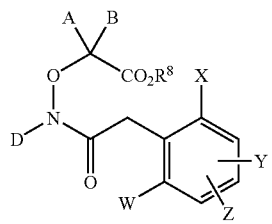

(XV)

in which

A, B, D, W, X, Y, Z and $R^8$ are each as defined above, but D is preferably not hydrogen, are obtained when, for example, phenylacetic acid derivatives of the formula (XXVIII)

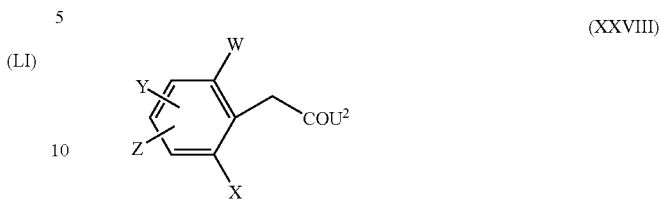

(XXVIII)

in which

W, X, Y, Z and $U^2$ are each as defined above are reacted with hydroxylamines of the formula (LIV)

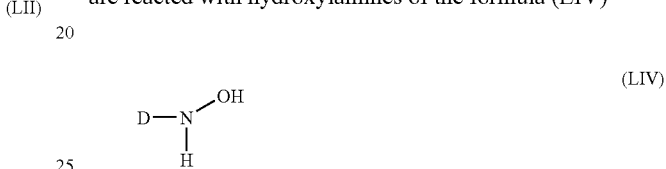

(LIV)

in which

D is as defined above, but is preferably not hydrogen, to give compounds of the formula (LV)

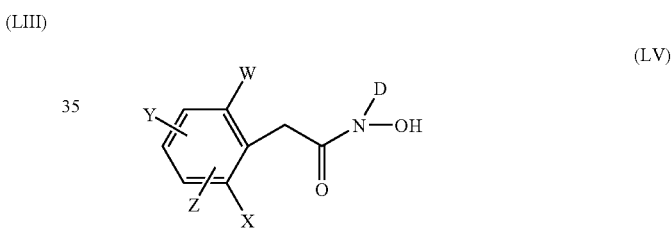

(LV)

in which

D, W, X, Y and Z are each as defined above, and the latter are alkylated with haloalkyl esters of the formula (LII),

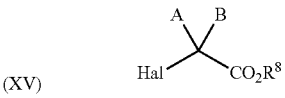

(LII)

in which

A, B and $R^8$ are each as defined above and

Hal is chlorine, bromine and iodine, preferably bromine, to give compounds of the formula (XV) (E. K. Ryo et. al., Bull. Korean Chem. Soc. 20 965 (1999)).

Some of the compounds of the formula (LIV) are commercially available, some are known, and can be prepared by known methods.

Moreover, compounds of the formula (XV) in which D is not hydrogen are obtained when compounds of the formula (XV-a)

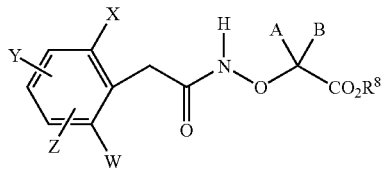

(XV-a)

in which
A, B, W, X, Y, Z and $R^8$ are each as defined above
are alkylated with compounds of the formula (LVI)

D-LG     (LVI)

in which
D is as defined above, but is not hydrogen,
and
LG is a leaving group, for example chlorine, bromine, iodine, mesylate, tosylate or triflate
to give compounds of the formula (XV) (WO 03/048138).

Some of the compounds of the formula (LVI) are commercially available, some are known, and can be prepared by known methods.

The compounds of the formulae (LIII) and (LV) are known and are preparable according to the literature cited at the outset.

The acid halides of the formula (XVI), carboxylic anhydrides of the formula (XVII), chloroformic esters or chloroformic thioesters of the formula (XVIII), chloromonothioformic esters or chlorodi-thioformic esters of the formula (XIX), sulphonyl chlorides of the formula (XX), phosphorus compounds of the formula (XXI) and metal hydroxides, metal alkoxides or amines of the formula (XXII) and (XXIII) and isocyanates of the formula (XXIV) and carbamyl chlorides of the formula (XXV) and haloalkanols of the formula (XXVI) also required as starting materials to perform the methods (L), (M), (N), (O), (P), (O), (R) and (S) according to the invention are commonly known compounds in organic or inorganic chemistry.

The compounds of the formulae (V), (VII), (X), (XXVII), (XXX), (XXXII), (XXXIV-A), (XXXIV-B), (XXXVI), (XL), (XLI-a), (XLI-b), (XLIV), (XLV), (XLVI), (XLVIII), (XLIX), (LI), (LII), (LIV) and (LVI) are additionally known from the patent applications cited at the outset and/or can be prepared by the methods specified there.

The compounds of the formulae (I-1'-I-11') can be prepared analogously to the methods A to R described and some are novel. The compounds of the formula (I-1'-a) are novel and can be prepared by method A. Some of the phenylacetic acids of the formula (XXXI') required to prepare the compounds of the formula (I-1'-a)

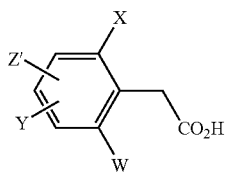

(XXXI')

in which W, X, Y and Z' are each as defined above are novel.

Compounds of the formula (XXXI') in which Z' is in the 3 position and Y is hydrogen are novel.

Method (A) is characterized in that compounds of the formula (II) in which A, B, W, X, Y, Z and $R^8$ are each as defined above are subjected to an intramolecular condensation in the presence of a base.

The diluents used in method (A) according to the invention may be any inert organic solvent. Preference is given to using hydrocarbons, such as toluene and xylene, and also ethers, such as dibutyl ether, tetrahydrofuran, dioxane, glycol dimethyl ether and diglycol dimethyl ether, and additionally polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

The bases (deprotonating agents) used in the performance of method (A) according to the invention may be any customary proton acceptor. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase transfer catalysts, for example triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is additionally possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When performing method (A) according to the invention, the reaction temperatures may be varied within a relatively wide range. In general, the temperatures employed are between 0° C. and 250° C., preferably between 50° C. and 150° C.

Method (A) according to the invention is generally performed under atmospheric pressure.

When performing method (A) according to the invention, the reaction components of the formula (II) and the deprotonating bases are generally employed in about double the equimolar amounts. However, it is also possible to use one component or the other in a greater excess (up to 3 mol).

Method (B) is characterized in that compounds of the formula (III) in which A, B, W, X, Y, Z and $R^8$ are each as defined above are subjected to an intramolecular condensation in the presence of a diluent and in the presence of a base.

The diluents used for the method (B) according to the invention may be any inert organic solvent.

Preference is given to using hydrocarbons, such as toluene and xylene, and also ethers, such as dibutyl ether, tetrahydrofuran, dioxane, glycol dimethyl ether and diglycol dimethyl ether, and additionally polar solvents, such as dimethyl sulphoxide, sulpholane, dimethylformamide and N-methylpyrrolidone. It is also possible to use alcohols, such as methanol, ethanol, propanol, isopropanol, butanol, isobutanol and tert-butanol.

The bases (deprotonating agents) used when performing method (B) according to the invention may be any customary proton acceptor. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is also possible to use alkali metals, such as sodium or potassium. In addition, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When performing method (B) according to the invention, the reaction temperatures may be varied within a relatively wide range. In general, the temperatures employed are between 0° C. and 250° C., preferably between 50° C. and 150° C.

Method (B) according to the invention is generally performed under atmospheric pressure.

When performing method (B) according to the invention, the reaction components of the formula (III) and the deprotonating bases are generally employed in about equimolar amounts. However, it is also possible to use one component or the other in a greater excess (up to 3 mol).

Method (C) is characterized in that compounds of the formula (IV) in which A, B, V, W, X, Y, Z and $R^8$ are each as defined above are intramolecularly cyclized in the presence of an acid and optionally in the presence of a diluent.

The diluents used in method (C) according to the invention may be any inert organic solvent. Preference is given to using hydrocarbons, such as toluene and xylene, and also halogenated hydrocarbons, such as dichloromethane, chloroform, ethylene chloride, chlorobenzene, dichlorobenzene, and also polar solvents, such as dimethyl sulphoxide, sulpholane, dimethylformamide and N-methylpyrrolidone. It is additionally possible to use alcohols such as methanol, ethanol, propanol, isopropanol, butanol, isobutanol, tert-butanol.

The acid used may optionally also serve as the diluent.

The acid used in method (C) according to the invention may be any customary inorganic or organic acid, for example hydrohalic acids, sulphuric acid, alkyl-, aryl- and haloalkyl-sulphonic acids, especially halogenated alkylcarboxylic acids, for example trifluoroacetic acid.

The reaction temperatures when performing method (C) according to the invention may be varied within a relatively wide range. In general, the temperatures employed are between 0° C. and 250° C., preferably between 50° C. and 150° C.

Method (C) according to the invention is generally performed under atmospheric pressure.

When performing method (C) according to the invention, the reaction components of the formula (IV) and the acid are used, for example, in equimolar amounts. However, it is also possible in some cases to use the acid as the solvent or as the catalyst.

Method (D) according to the invention is characterized in that carbonyl compounds of the formula (V) or the enol ether thereof, of the formula (V-a), is reacted with ketenoyl halides of the formula (VI) in the presence of a diluent and optionally in the presence of an acid acceptor.

The diluents used in method (D) according to the invention may be any inert organic solvent. Preference is given to using optionally halogenated hydrocarbons, such as toluene, xylene, mesitylene, chlorobenzene and dichlorobenzene, and also ethers, such as dibutyl ether, glycol dimethyl ether, diglycol dimethyl ether and diphenyl ether, and also polar solvents, such as dimethyl sulphoxide, sulpholane, dimethylformamide or N-methylpyrrolidone.

The acid acceptors used when performing method variant (D) according to the invention may be any customary acid acceptor.

Preference is given to using tertiary amines, such as triethylamine, pyridine, diazabicyclooctane (DABCO), diazabicycloundecane (DBU), diazabicyclononene (DBN), Hünig's base and N,N-dimethylaniline.

The reaction temperatures when performing method variant (D) according to the invention can be varied within a relatively wide range. It is appropriate to work at temperatures between 0° C. and 250° C., preferably between 50° C. and 220° C.

Method (D) according to the invention is appropriately performed under atmospheric pressure.

When performing method (D) according to the invention, the reaction components of the formulae (V) and (VI) in which A, D, W, X, Y and Z are each as defined above and Hal is halogen, and optionally the acid acceptors, are generally used in about equimolar amounts. However, it is also possible to use one or the other component in a greater excess (up to 5 mol).

Method (E) according to the invention is characterized in that thioamides of the formula (VII) are reacted with ketenoyl halides of the formula (VI) in the presence of a diluent and optionally in the presence of an acid acceptor.

The diluents used in method variant (E) according to the invention may be any inert organic solvent. Preference is given to using hydrocarbons, such as toluene and xylene, and also ethers, such as dibutyl ether, glycol dimethyl ether and diglycol dimethyl ether, and also polar solvents, such as dimethyl sulphoxide, sulpholane, dimethylformamide and N-methylpyrrolidone.

The acid acceptors used when performing method (E) according to the invention may be any customary acid acceptor.

Preference is given to using tertiary amines, such as triethylamine, pyridine, diazabicyclooctane (DABCO), diazabicycloundecane (DBU), diazabicyclononene (DBN), Hünig's base and N,N-dimethylaniline.

The reaction temperatures when performing method (E) according to the invention can be varied within a relatively wide range. It is appropriate to work at temperatures between 0° C. and 250° C., preferably between 20° C. and 220° C.

Method (E) according to the invention is appropriately performed under atmospheric pressure.

When performing method (E) according to the invention, the reaction components of the formulae (VII) and (VI) in which A, W, X, Y and Z are each as defined above and Hal is halogen and optionally the acid acceptors are generally used in about equimolar amounts. However, it is also possible to use one or the other component in a greater excess (up to 5 mol).

Method (F) is characterized in that compounds of the formula (VIII) in which A, B, $Q^1$, $Q^2$, W, X, Y, Z and $R^8$ are each as defined above are subjected to an intramolecular condensation in the presence of a base.

The diluents used in method (F) according to the invention may be any organic solvent inert toward the reaction participants. Preference is given to using hydrocarbons, such as toluene and xylene, and also ethers, such as dibutyl ether, tetrahydrofuran, dioxane, glycol dimethyl ether and diglycol dimethyl ether, and also polar solvents, such as collidine, dimethyl sulphoxide; sulpholane, dimethylformamide and N-methylpyrrolidone. It is additionally possible to use alcohols such as methanol, ethanol, propanol, isopropanol, butanol, isobutanol, tert-butanol.

The bases (deprotonating agents) used when performing method (F) according to the invention may be any customary proton acceptor. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, for example triethylbenzylammonium chloride, tetrabutylammonium bromide, Adogen 464 (methyltrialkyl($C_8$-$C_{10}$)ammonium chloride) or TDA 1 (tris(methoxyethoxyethyl)amine). In addition, alkali metals such as sodium or potassium can be used. Additionally usable are alkali metal and alkaline earth metal amides and hydrides, such as sodium amide, sodium hydride and calcium hydride, and additionally also alkali metal alkoxides such as sodium methoxide, sodium ethoxide and potassium tert-butoxide.

The reaction temperatures when performing method (F) according to the invention can be varied within a relatively wide range. In general, the temperatures employed are between −75° C. and 250° C., preferably between −50° C. and 150° C.

Method (F) according to the invention is generally performed under atmospheric pressure.

When performing method (F) according to the invention, the reaction components of the formula (VIII) and the deprotonating bases are generally used in about equimolar amounts. However, it is also possible to use one or the other component in a greater excess (up to 3 mol).

Method (G) is characterized in that compounds of the formula (IX) in which A, B, $Q^5$, $Q^6$, U, W, X, Y, Z and $R^8$ are each as defined above are subjected to an intramolecular condensation in the presence of bases.

The diluents used in method (G) according to the invention may be any organic solvent inert toward the reaction participants. Preference is given to using hydrocarbons, such as toluene and xylene, and also ethers, such as dibutyl ether, tetrahydrofuran, dioxane, glycol dimethyl ether and diglycol dimethyl ether, and also polar solvents, such as dimethyl sulphoxide, sulpholane, dimethylformamide and N-methylpyrrolidone. It is additionally possible to use alcohols such as methanol, ethanol, propanol, isopropanol, butanol, isobutanol, tert-butanol.

The bases (deprotonating agents) used when performing method (G) according to the invention may be any customary proton acceptor.

Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, for example triethylbenzylammonium chloride, tetrabutylammonium bromide, Adogen 464 (methyltrialkyl($C_8$-$C_{10}$)ammonium chloride) or TDA 1 (tris(methoxyethoxyethyl)amine). In addition, alkali metals such as sodium or potassium can be used. Additionally usable are alkali metal and alkaline earth metal amides and hydrides, such as sodium amide, sodium hydride and calcium hydride, and additionally also alkali metal alkoxides such as sodium methoxide, sodium ethoxide and potassium tert-butoxide.

The reaction temperatures when performing method (G) according to the invention can be varied within a relatively wide range. In general, the temperatures employed are between 0° C. and 250° C., preferably between 50° C. and 150° C.

Method (G) according to the invention is generally performed under atmospheric pressure.

When performing method (G) according to the invention, the reaction components of the formula (IX) and the deprotonating bases are generally used in about equimolar amounts. However, it is also possible to use one or the other component in a greater excess (up to 3 mol).

Method (H-α) according to the invention is characterized in that hydrazines of the formula (X) or salts of these compounds are reacted with ketenoyl halides of the formula (VI) in the presence of a diluent and optionally in the presence of an acid acceptor.

The diluents used in method (H-α) according to the invention may be any inert organic solvent. Preference is given to using optionally chlorinated hydrocarbons, for example mesitylene, chlorobenzene and dichlorobenzene, toluene, xylene, and also ethers, such as dibutyl ether, glycol dimethyl ether, diglycol dimethyl ether and diphenylethane, and also polar solvents, such as dimethyl sulphoxide, sulpholane, dimethylformamide or N-methylpyrrolidone.

The acid acceptors used when performing method variant (H-α) according to the invention may be any customary acid acceptor.

Preference is given to using tertiary amines, such as triethylamine, pyridine, diazabicyclooctane (DABCO), diazabicycloundecane (DBU), diazabicyclononene (DBN), Hünig's base and N,N-dimethylaniline.

The reaction temperatures when performing method variant (H-α) according to the invention may be varied within a relatively wide range. It is appropriate to work at temperatures between 0° C. and 250° C., preferably between 50° C. and 220° C.

Method (H-α) according to the invention is appropriately performed under atmospheric pressure.

When performing method (H-α) according to the invention, the reaction components of the formulae (VI) and (X) in which A, D, W, X, Y and Z are each as defined above and Hal is halogen, and optionally the acid acceptors, are generally used in about equimolar amounts. However, it is also possible to use one or the other component in a greater excess (up to 5 mol).

Method (H-β) is characterized in that hydrazines of the formula (X) or salts of this compound, in which A and D are each as defined above, are subjected to a condensation with malonic esters or malonamides of the formula (XI) in which $U^1$, W, X, Y, Z and $R^8$ are each as defined above, in the presence of a base.

The diluents used in method (H-β) according to the invention may be any inert organic solvent. Preference is given to using optionally halogenated hydrocarbons, such as toluene, xylene, mesitylene, chlorobenzene and dichlorobenzene, and also ethers, such as dibutyl ether, tetrahydrofuran, dioxane, diphenyl ether, glycol dimethyl ether and diglycol dimethyl ether, and also polar solvents, such as dimethyl sulphoxide, sulpholane, dimethylformamide, dimethylacetamide and N-methylpyrrolidone, and also alcohols such as methanol, ethanol, propanol, isopropanol, butanol, isobutanol and tert-butanol.

The bases (deprotonating agents) used when performing method (H-β) according to the invention may be any customary proton acceptor. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, for example triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is additionally possible to use alkali metals such as sodium or potassium. It is also possible to use alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

It is also possible to use tertiary amines, such as triethylamine, pyridine, diazabicyclooctane (DABCO), diazabicycloundecane (DBU), diazabicyclononene (DBN), Hünig's base and N,N-dimethylaniline.

The reaction temperatures when performing method (H-β) according to the invention can be varied within a relatively wide range. In general, the temperatures employed are between 0° C. and 280° C., preferably between 50° C. and 180° C.

The method (H-β) according to the invention is generally performed under atmospheric pressure.

When performing method (H-β) according to the invention, the reaction components of the formulae (XI) and (X) are generally used in about equimolar amounts. However, it is also possible to use one or the other component in a greater excess (up to 3 mol).

Method (H-γ) is characterized in that compounds of the formula (XII) in which A, D, W, X, Y, Z and $R^8$ are each as defined above are subjected to an intramolecular condensation in the presence of a base.

The diluents used in method (H-γ) according to the invention may be any inert organic solvent. Preference is given to using hydrocarbons, such as toluene and xylene, and also ethers, such as dibutyl ether, tetrahydrofuran, dioxane, glycol dimethyl ether and diglycol dimethyl ether, and also polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

The bases (deprotonating agents) used when performing method (H-γ) according to the invention may be any customary proton acceptor. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, for example triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is additionally possible to use alkali metals such as sodium or potassium. It is also possible to use alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

The reaction temperatures when performing method (H-γ) according to the invention can be varied within a relatively wide range. In general, the temperatures employed are between 0° C. and 250° C., preferably between 50° C. and 150° C.

Method (H-γ) according to the invention is generally performed under atmospheric pressure.

When performing method (H-γ) according to the invention, the reaction components of the formula (XII) and the deprotonating bases are generally used in about double the equimolar amounts. However, it is also possible to use one or the other component in a greater excess (up to 3 mol).

Method (I) is characterized in that compounds of the formula (XIII) in which A, B, D, $Q^1$, $Q^2$, W, X, Y, Z and $R^8$ are each as defined above are subjected to an intramolecular condensation in the presence of a base.

The diluents used in method (I) according to the invention may be any inert organic solvent. Preference is given to using hydrocarbons, such as toluene and xylene, and also ethers, such as dibutyl ether, tetrahydrofuran, dioxane, glycol dimethyl ether and diglycol dimethyl ether, and also polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

The bases (deprotonating agents) used when performing method (I) according to the invention may be any customary proton acceptor. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, for example triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is additionally possible to use alkali metals such as sodium or potassium. It is also possible to use alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

The reaction temperatures when performing method (I) according to the invention can be varied within a relatively wide range. In general, the temperatures employed are between −80° C. and 180° C., preferably between −50° C. and 120° C.

Method (I) according to the invention is generally performed under atmospheric pressure.

When performing method (I) according to the invention, the reaction components of the formula (XIII) and the deprotonating bases are generally used in about double the equimolar amounts. However, it is also possible to use one or the other component in a greater excess (up to 3 mol).

Method (J) is characterized in that compounds of the formula (XIV) in which A, B, $Q^1$, $Q^2$, W, X, Y, Z and $R^8$ are each as defined above are subjected to an intramolecular condensation in the presence of a base.

The diluents used in method (J) according to the invention may be any inert organic solvent. Preference is given to using hydrocarbons, such as toluene and xylene, and also ethers, such as dibutyl ether, tetrahydrofuran, dioxane, glycol dimethyl ether and diglycol dimethyl ether, and also polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

The bases (deprotonating agents) used when performing method (J) according to the invention may be any customary proton acceptor. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, for example triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is additionally possible to use alkali metals such as sodium or potassium.

It is also possible to use alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

The reaction temperatures when performing method (J) according to the invention may be varied within a relatively wide range. In general, temperatures between 0° C. and 250° C., preferably between 50° C. and 150° C., are employed.

Method (J) according to the invention is generally performed under atmospheric pressure.

When performing method (J) according to the invention, the reaction components of the formula (XIV) and the deprotonating bases are generally used in about double the equimolar amounts. However, it is also possible to use one or the other component in a greater excess (up to 3 mol).

Method (K) is characterized in that compounds of the formula (XV) in which A, B, D, W, X, Y, Z and $R^8$ are each as defined above are subjected to an intramolecular condensation in the presence of a base.

The diluents used in method (K) according to the invention may be any inert organic solvent. Preference is given to using hydrocarbons, such as toluene and xylene, and also ethers, such as dibutyl ether, tetrahydrofuran, dioxane, glycol dimethyl ether and diglycol dimethyl ether, and also polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

The bases (deprotonating agents) used when performing method (K) according to the invention may be any customary proton acceptor. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, for example triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is additionally possible to use alkali metals such as sodium or potassium. It is also possible to use alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When performing method (K) according to the invention, the reaction temperatures can be varied within a relatively wide range. In general, the temperatures employed are between −78° C. and 250° C., preferably between 0° C. and 150° C.

Method (K) according to the invention is generally performed under atmospheric pressure.

When performing method (K) according to the invention, the reaction components of the formula (XV) and the deprotonating bases are generally used in about double the equimolar amounts. However, it is also possible to use one or the other component in a greater excess (up to 3 mol).

Method (L-α) is characterized in that compounds of the formulae (I-1-a) to (I-11-a) are each reacted with carbonyl halides of the formula (XVI), optionally in the presence of a diluent and optionally in the presence of an acid binder.

The diluents used in method (L-α) according to the invention may be all solvents inert toward the acid halides. Preference is given to using hydrocarbons, such as benzine, benzene, toluene, xylene and tetralin, and also halohydrocarbons, such as methylene chloride, chloroform, carbon tetrachloride, chlorobenzene and o-dichlorobenzene, and also ketones, such as acetone and methyl isopropyl ketone, and additionally ethers, such as diethyl ether, tetrahydrofuran and dioxane, and additionally carboxylic esters, such as ethyl acetate, and also strongly polar solvents, such as dimethyl sulphoxide and sulpholane. If the hydrolysis stability of the acid halide permits it, the reaction can also be performed in the presence of water.

Useful acide binders in the reaction in the process according to the invention (L-α) are any customary acid acceptor. Preference is given to using tertiary amines, such as triethylamine, pyridine, diazabicyclooctane (DABCO), diazabicycloundecene (DBU), diazabicyclononene (DBN), Hünig's base and N,N-dimethylaniline, and also alkaline earth metal oxides, such as magnesium and calcium oxide, and also alkali metal and alkaline earth metal carbonates, such as sodium carbonate, potassium carbonate and calcium carbonate, and also alkali metal hydroxides such as sodium hydroxide and potassium hydroxide.

The reaction temperatures in method (L-α) according to the invention may be varied within a relatively wide range. In general, the temperatures employed are between −20° C. and +150° C., preferably between 0° C. and 100° C.

When performing method (L-α) according to the invention, the starting materials of the formulae (I-1-a) to (I-11-a) and the carbonyl halide of the formula (XVI) are generally used each in approximately equivalent amounts. However, it is also possible to use the carbonyl halide in a greater excess (up to 5 mol). The workup is effected by customary methods.

Method (L-β) is characterized in that compounds of the formulae (I-1-a) to (I-11-a) are reacted with carboxylic anhydrides of the formula (XVII), optionally in the presence of a diluent and optionally in the presence of an acid binder.

The diluents used in method (L-β) according to the invention are preferably those diluents which are also preferably considered when acid halides are used. Otherwise, a carboxylic anhydride used in excess may function simultaneously as a diluent.

Useful acid binders optionally added in method (L-β) are preferably those acid binders which are preferably also considered when acid halides are used.

The reaction temperatures in method (L-β) according to the invention can be varied within a relatively wide range. In general, the temperatures employed are between −20° C. and +150° C., preferably between 0° C. and 100° C.

When performing method (L-β) according to the invention, the starting materials of the formulae (I-1-a) to (I-11-a) and the carboxylic anhydride of the formula (XVII) are generally each used in approximately equivalent amounts. However, it is also possible to use the carboxylic anhydride in a greater excess (up to 5 mol). The workup is effected by customary methods.

In general, diluent and excess carboxylic anhydride and the carboxylic acid formed are removed by distillation or by washing with an organic solvent or with water.

Method (M) is characterized in that compounds of the formulae (I-1-a) to (I-11-a) are in each case reacted with chloroformic esters or chloroformic thioesters of the formula (XVIII), optionally in the presence of a diluent and optionally in the presence of an acid binder.

Suitable acid binders for the reaction in method (M) according to the invention are any customary acid acceptor. Preference is given to using tertiary amines, such as triethylamine, pyridine, DABCO, DBU, DBA, Hünig's base and N,N-dimethylaniline, and also alkaline earth metal oxides, such as magnesium oxide and calcium oxide, and also alkali metal and alkaline earth metal carbonates, such as sodium carbonate, potassium carbonate and calcium carbonate, and also alkali metal hydroxides, such as sodium hydroxide and potassium hydroxide.

Suitable diluents for use in method (M) according to the invention are any solvents which are inert towards the chloroformic esters or chloroformic thioesters. Preference is given to using hydrocarbons, such as benzine, benzene, toluene, xylene and tetralin, and also halogenated hydrocarbons, such as methylene chloride, chloroform, carbon tetrachloride, chlorobenzene and o-dichlorobenzene, and also ketones, such as acetone and methyl isopropyl ketone, and also ethers, such as diethyl ether, tetrahydrofuran and dioxane, and additionally carboxylic esters, such as ethyl acetate, and also strongly polar solvents, such as dimethyl sulphoxide and sulpholane.

When performing method (M) according to the invention, the reaction temperatures can be varied within a relatively wide range. If the method is performed in the presence of a diluent and an acid binder, the reaction temperatures are generally between $-20°$ C. and $+100°$ C., preferably between $0°$ C. and $50°$ C.

Method (M) according to the invention is generally performed under atmospheric pressure.

When performing method (M) according to the invention, the starting materials of the formulae (I-1-a) to (I-11-a) and the appropriate chloroformic ester or chloroformic thioester of the formula (XVIII) are generally each employed in approximately equivalent amounts. However, it is also possible to use one component or the other in a greater excess (up to 2 mol). Workup is performed by customary methods. In general, precipitated salts are removed and the reaction mixture that remains is concentrated by removing the diluent under reduced pressure.

Method (N) according to the invention is characterized in that compounds of the formulae (I-1-a) to (I-11-a) are in each case reacted with compounds of the formula (XIX) in the presence of a diluent and optionally in the presence of an acid binder.

In preparation method (N), about 1 mol of chloromonothioformic ester or chlorodithioformic ester of the formula (XIX) is reacted per mole of the starting compound of the formulae (I-1-a) to (I-11-a) at from 0 to $120°$ C., preferably from 20 to $60°$ C.

Suitable diluents which are added optionally are any inert polar organic solvent, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-1-a) to (I-11-a) is prepared by addition of strong deprotonating agents, for example sodium hydride or potassium tert-butoxide, the further addition of acid binders may be dispensed with.

If acid binders are used, these are customary inorganic or organic bases; examples include sodium hydroxide, sodium carbonate, potassium carbonate, pyridine and triethylamine.

The reaction may be performed at atmospheric pressure or under elevated pressure, preference being given to working at atmospheric pressure. Workup is performed by customary methods.

Method (O) according to the invention is characterized in that compounds of the formulae (I-1-a) to (I-11-a) are in each case reacted with sulphonyl chlorides of the formula (XX), optionally in the presence of a diluent and optionally in the presence of an acid binder.

In preparation method (O), about 1 mol of sulphonyl chloride of the formula (XX) is reacted per mole of the starting compound of the formulae (I-1-a) to (I-11-a) at from $-20$ to $150°$ C., preferably from 20 to $70°$ C.

Useful diluents which are optionally added are any inert polar organic solvent, such as ethers, amides, nitriles, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-1-a) to (I-11-a) is prepared by addition of strong deprotonating agents (for example sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction may be performed at atmospheric pressure or under elevated pressure and is preferably performed at atmospheric pressure. Workup is performed by customary methods.

Method (P) according to the invention is characterized in that compounds of the formulae (I-1-a) to (I-11-a) are reacted with phosphorus compounds of the formula (XXI), optionally in the presence of a diluent and optionally in the presence of an acid binder.

In preparation method (P), to obtain compounds of the formulae (I-1-e) to (I-11-e), from 1 to 2, preferably from 1 to 1.3, mol of the phosphorus compound of the formula (XXI) are reacted per mole of the compounds (I-1-a) to (I-11-a), at temperatures between $-40°$ C. and $150°$ C., preferably between $-10$ and $110°$ C.

Suitable diluents which are added optionally are any inert polar organic solvent, such as ethers, amides, nitriles, alcohols, sulphides, sulphones, sulphoxides, etc.

Preference is given to using acetonitrile, dimethyl sulphoxide, tetrahydrofuran, dimethyl-formamide, methylene chloride.

Suitable acid binders which are optionally added are customary inorganic or organic bases, such as hydroxides, carbonates or amines. Examples include sodium hydroxide, sodium carbonate, potassium carbonate, pyridine and triethylamine.

The reaction can be performed at atmospheric pressure or under elevated pressure and is preferably performed at atmospheric pressure. Workup is performed by customary methods of organic chemistry. The resulting end products are preferably purified by crystallization, chromatographic purification or "incipient distillation", i.e. removal of the volatile components under reduced pressure.

Method (Q) is characterized in that compounds of the formulae (I-1-a) to (I-11-a) are reacted with metal hydroxides or metal alkoxides of the formula (XXII) or amines of the formula (XXII), optionally in the presence of a diluent.

Suitable diluents for use in method (Q) according to the invention are, preferably, ethers, such as tetrahydrofuran, dioxane, diethyl ether, or else alcohols, such as methanol, ethanol, isopropanol, and also water.

Method (Q) according to the invention is generally performed under atmospheric pressure.

The reaction temperatures are generally between $-20°$ C. and $100°$ C., preferably between $0°$ C. and $50°$ C.

Method (R) according to the invention is characterized in that compounds of the formulae (I-1-a) to (I-11-a) are reacted in each case with (R-α) compounds of the formula (XXIV), optionally in the presence of a diluent and optionally in the presence of a catalyst, or (R-β) with compounds of the formula (XXV), optionally in the presence of a diluent and optionally in the presence of an acid binder.

In preparation method (R-α), about 1 mol of isocyanate of the formula (XXIV) is reacted per mole of starting compound of the formulae (I-1-a) to (I-11-a), at from 0 to 100° C., preferably from 20 to 50° C.

Suitable diluents which are added optionally are any inert organic solvent, such as ethers, amides, nitriles, sulphones or sulphoxides.

Optionally, catalysts may be added to accelerate the reaction. Suitable for use as catalysts are, very advantageously, organotin compounds, for example dibutyltin dilaurate. The reaction is preferably performed at atmospheric pressure.

In preparation method (R-β), about 1 mol of carbamoyl chloride of the formula (XXV) is reacted per mole of starting compound of the formulae (I-1-a) to (I-11-a), at from −20 to 150° C., preferably at from 0 to 70° C.

Suitable diluents which are added optionally are any inert polar organic solvent, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-1-a) to (I-11-a) is prepared by addition of strong deprotonating agents (for example sodium hydride or potassium tert-butoxide), the further addition of acid binders may be dispensed with.

If acid binders are used, they are customary inorganic or organic bases, for example sodium hydroxide, sodium carbonate, potassium carbonate, triethylamine or pyridine.

The reaction can be performed at atmospheric pressure or under elevated pressure and is preferably performed at atmospheric pressure. Workup is performed by customary methods.

Method (S) is characterized in that compounds of the formulae (I-1') to (I-11') in which A, B, D, G, $Q^1$, $Q^2$, U, $Q^5$, $Q^6$, W, X and Y are each as defined above and Z' is preferably bromine or iodine are reacted with alcohols of the formula ZOH in which Z is as defined above, in the presence of a base and of a Cu(I) salt (e.g. CuBr or CuI).

The diluents used in method (S) according to the invention may be any organic solvent inert toward the reaction participants. Preference is given to using hydrocarbons, such as toluene and xylene, and also ethers, such as dibutyl ether, tetrahydrofuran, dioxane, glycol dimethyl ether and diglycol dimethyl ether, and also polar solvents, such as collidine, dimethyl sulphoxide, sulpholane, dimethyl-formamide, dimethylacetamide and N-methylpyrrolidone, esters such as methyl acetate, ethyl acetate, propyl acetate, and alcohols of the formula WOH, for example methanol, ethanol, propanol, isopropanol, butanol and isobutanol.

The bases (deprotonating agents) used when performing method (S) according to the invention may be any customary proton acceptor. Preference is given to using alkali metals such as sodium or potassium. It is additionally possible to use alkali metal and alkaline earth metal amides and hydrides, such as sodium amide, sodium hydride and calcium hydride, and preferably also alkali metal alkoxides such as sodium methoxide, sodium ethoxide, sodium isopropoxide, sodium tert-butoxide and potassium tert-butoxide.

The reaction temperature when performing method (S) according to the invention may be varied within a relatively wide range. In general, the temperatures employed are between 0° C. and 250° C., preferably between 50° C. and 150° C.

Method (S) according to the invention is generally performed under atmospheric pressure.

When performing method (S) according to the invention, the reaction component of the formula (I-1') to (I-11') is generally reacted with excesses of the alcohols ZOH and of the bases of up to 20 mol, preferably 3 to 5 mol. The copper(I) salts are generally used in catalytic amounts; 0.001 to 0.5 mol, preferably 0.01 to 0.2 mol. However, it is also possible to use them in equimolar amounts.

The inventive active ingredients are suitable, given good plant compatibility, favourable toxicity to warm-blooded animals and good environmental compatibility, for protecting plants and plant organs; for increasing harvest yields, improving the quality of the harvest and for controlling animal pests, especially insects, aracnids, helminthes, nematodes and molluscs, which are encountered in agriculture, in horticulture, in animal breeding, in forests, in gardens and leisure facilities, in the protection of stored products and materials, and in the hygiene sector. They can preferably be used as crop protection compositions. They are active against normally sensitive and resistant species, and against all or some stages of development. The abovementioned pests include:

From the phylum Mollusca, for example from the class of the Lamellibranchiata, for example *Dreissena* spp.

From the class of the Gastropoda, for example *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the phylum Arthropoda, for example from the order of the Isopoda, for example *Armadillidium vulgare, Oniscus asellus, Porcellio scaber.*

From the class of the Arachnida, for example *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

From the order of the Symphyla, for example *Scutigerella* spp.

From the order of the Chilopoda, for example *Geophilus* spp., *Scutigera* spp.

From the order of the Collembola, for example *Onychiurus armatus.*

From the order of the Diplopoda, for example *Blaniulus guttulatus.*

From the order of the Zygentoma, for example *Lepisma saccharina, Thermobia domestica.*

From the order of the Orthoptera, for example *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of the Isoptera, for example *Coptotermes* spp., *Cornitermes cumulans, Cryptotermes* spp., *Incisitermes* spp., *Microtermes obesi, Odontotermes* spp., *Reticulitermes* spp., From the order of the Heteroptera, for example *Anasa tristis*, *Antestiopsis* spp., *Boisea* spp., *Blissus* spp., *Calocoris* spp., *Campylomma livida*, *Cavelerius* spp., *Cimex lectularius*, *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Anoplura (*Phthiraptera*), for example *Damalinia* spp., *Haematopinus* spp., *Linognathus* spp., *Pediculus* spp., *Ptirus pubis*, *Trichodectes* spp.

From the order of the Homoptera, for example *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cocadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Coleoptera, for example *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lisso-rhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sphenophorus* spp., *Stegobium paniceum*, *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Hymenoptera, for example *Acromyrmex* spp., *Athalia* spp., *Atta* spp., *Diprion* spp., *Hoplocampa* spp., *Lasius* spp., *Monomorium pharaonic*, *Solenopsis invicta*, *Tapinoma* spp., *Vespa* spp.

From the order of the Lepidoptera, for example *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichophaga tapetzella*, *Trichoplusia* spp., *Tuta absoluta*, *Virachola* spp.

From the order of the Diptera, for example *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp., *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp. *Lucilia* spp., *Lutzomia* spp., *Mansonia* spp., *Musca* spp.,

*Nezara* spp., *Oestrus* spp., *Oscinella frit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium* spp, *Stomoxys* spp., *Tabanus* spp., *Tannia* spp., *Tetanops* spp., *Tipula* spp.

From the order of the Thysanoptera, for example *Anaphothrips obscurus*, *Baliothrips biformis*, *Drepanothris reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Siphonaptera, for example *Ceratophyllus* spp., *Ctenocephalides* spp., *Tunga penetrans*, *Xenopsylla cheopis*.

From the phyla of the Plathelminthes and Nematodes as animal parasites, for example from the class of the Helminthes, for example *Ancylostoma duodenale*, *Ancylostoma ceylanicum*, *Acylostoma braziliensis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp: *Opisthorchis* spp., *Onchocerca volvulus*, *Ostertagia* spp., *Paragonimus* spp., *Schistosomen* spp, *Strongyloides fuelleborni*, *Strongyloides stercoralis*, *Stronyloides* spp., *Taenia saginati*; *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

From the phylum of the Nematodes as plant pests, for example *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

From the subphylum of the Protozoa, for example *Eimeria*.

If appropriate, the inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*Mycoplasma*-like organisms) and RLO (*Rickettsia*-like organisms). If appropriate, they can also be employed as intermediates or precursors for the synthesis of other active ingredients.

All plants and plant parts can be treated in accordance with the invention. Plants should be understood to mean, in the present context, all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts should be understood to mean all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Inventive treatment of the plants and plant parts with the active ingredients is effected directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

The active ingredients can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active ingredient, synthetic materials impregnated with active ingredient, fertilizers and microencapsulations in polymeric substances.

These formulations are produced in a known manner, for example by mixing the active ingredients with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

According to the invention, "carrier" means a natural or synthetic, organic or inorganic substance which may be solid or liquid, with which the active ingredients are mixed or combined for better applicability, especially for application to plants or plant parts. The solid or liquid carrier is generally inert and should be usable in agriculture.

Useful solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use dyes such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally contain between 0.01 and 98% by weight of active ingredient, preferably between 0.5 and 90%.

The inventive active ingredient can be used in its commercially available formulations and in the use forms, prepared from these formulations, as a mixture with other active ingredients, such as insecticides, attractants, sterilizing agents, bactericides, acaricides, nematicides, fungicides, growth-regulating substances, herbicides, safeners, fertilizers or semiochemicals.

A mixture with other known active ingredients, such as herbicides, fertilizers, growth regulators, safeners, semiochemicals, or else with agents for improving the plant properties, is also possible.

When used as insecticides, the inventive active ingredients may additionally be present in their commercially available formulations and in the use forms, prepared from these formulations, as a mixture with synergistic agents. Synergistic agents are compounds which increase the action of the active ingredients, without it being necessary for the synergistic agent added to be active itself.

When used as insecticides, the inventive active ingredients can furthermore be present in their commercially available formulations and in the use forms, prepared from these formulations, as a mixture with inhibitors which reduce degradation of the active ingredient after use in the environment of the plant, on the surface of parts of plants or in plant tissues.

The active ingredient content of the use forms prepared from the commercially available formulations can vary within wide limits. The active ingredient concentration of the use forms can be from 0.00000001 to 95% by weight of active ingredient, preferably between 0.00001 and 1% by weight.

The compounds are employed in a customary manner appropriate for the use forms.

The inventive active ingredients act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The inventive active ingredients of the formula (I) are also suitable for controlling arthropods which infest agricultural productive livestock, for example cattle, sheep, goats, horses, pigs, donkeys, camels, buffalo, rabbits, chickens, turkeys, ducks, geese and bees, other pets, for example dogs, cats, caged birds and aquarium fish, and also so-called test animals, for example hamsters, guinea pigs, rats and mice. By controlling these arthropods, cases of death and reductions in productivity (for meat, milk, wool, hides, eggs, honey etc.) should be diminished, so that more economic and easier animal husbandry is possible by use of the inventive active ingredients.

The inventive active ingredients are used in the veterinary sector and in animal husbandry in a known manner by enteral administration in the form of, for example, tablets, capsules, portions, drenches, granules, pastes, boluses, the feed-through process and suppositories, by parenteral administration, for example by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for cattle, poultry, pets and the like, the active ingredients of the formula (I) can be used as formulations (for example powders, emulsions, free-flowing compositions), which comprise the active ingredients in an amount of 1 to 80% by weight, directly or after 100- to 10 000-fold dilution, or they can be used as a chemical bath.

It has additionally been found that the inventive compounds have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina*.

Industrial materials in the present connection should be understood to mean non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The inventive compounds can likewise be employed for protecting objects which come into contact with saltwater or brackish water, in particular hulls, screens, nets, buildings, moorings and signalling systems, against fouling.

Furthermore, the inventive compounds, alone or in combinations with other active ingredients, may be employed as antifouling agents.

In domestic, hygiene and stored-product protection, the active ingredients are also suitable for controlling animal pests, in particular insects, arachnids and mites, which are found in enclosed spaces for example dwellings, factory halls, offices, vehicle cabins and the like. They can be employed alone or in combination with other active ingredients and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active ingredients, such as phosphoric esters, carbamates, pyrethroids, neonicotinoids, growth regulators or active ingredients from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The inventive compounds of the formula (I) (active ingredients) have marked herbicidal activity against a broad spectrum of economically important mono- and dicotyledonous annual harmful plants. Even perennial harmful plants which are difficult to control, which produce shoots from rhizomes, rootstocks or other permanent organs, are well-controlled by the active ingredients.

The application rate of active ingredient can vary within a relatively wide range. Essentially, it depends on the nature of the desired effect. In general, the application rates are between 1 g and 10 kg of active ingredient per hectare of soil area, preferably between 5 g and 5 kg per ha.

The advantageous effect of the compatibility with crop plants of the inventive active ingredient combinations is particularly pronounced at certain concentration ratios. However, the weight ratios of the active ingredients in the active ingredient combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active ingredient of the formula (I).

The inventive active ingredient combinations are generally applied in the form of finished formulations. However, the active ingredients present in the active ingredient combinations can, as individual formulations, also be mixed during use, i.e. be applied in the form of tank mixes.

For certain applications, in particular in the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulphate or ammonium thiocyanate.

The novel active ingredient combinations can be used as such, in the form of their formulations or the use forms prepared therefrom by further dilution, such as ready-to-use solutions, suspensions, emulsions, powders, pastes and granules. Application is in the customary manner, for example by watering, spraying, atomizing, dusting or scattering.

The application rates of the active ingredient combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

Depending on their properties, the safeners for use in accordance with the invention can be used to pretreat the seed of the crop plant (seed dressing) or can be introduced into the seed furrows prior to sowing or be used separately prior to the herbicide or together with the herbicide, before or after emergence of the plants.

Examples of plants include important crop plants, such as cereals (wheat, barley, rice), maize, soya beans, potatoes, cotton, oilseed rape, beet, sugar cane and also fruit plants (with the fruits apples, pears, citrus fruits and grapevines), greater emphasis being given to cereals, maize, soya beans, potatoes, cotton and oilseed rape.

All plants and plant parts can be treated with the inventive active ingredients. In this context, plants should be understood to mean all plants and plant populations such as wanted and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts should be understood to mean all parts and organs of plants above and below the ground, such as shoot, leaf, flower and root, examples which may be mentioned being leaves, needles, stalks, stems, flowers, fruit bodies, fruits and seed and also roots, tubers and rhizomes. The plant parts also include harvested material, and also vegetative and generative propagation material, for example cuttings, tubers, rhizomes, offshoots and seeds.

The inventive treatment of the plants and plant parts with the active ingredients is effected directly or by allowing the compounds to act on their surroundings, habitat or storage space by the customary treatment methods, for example by immersion, spraying, evaporation, fogging, broadcasting, painting on or injection and, in the case of propagation material, especially in the case of seed, also by applying one or more coats.

The present invention therefore also provides a method of controlling undesired plants or for regulating the growth of plants, preferably in crops of plants, wherein one or more inventive compound(s) is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the inventive compounds can be applied for example pre-planting (if appropriate also by incorporation into the soil), pre-emergence or post-emergence. Examples of individual representatives of the monocotyledonous and dicotyledonous weed flora which can be controlled by the inventive compounds will be mentioned, though there is no intention to impose a restriction to particular species mentioned.

Monocotyledonous Harmful Plants of the Genera:

*Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous Weeds of the Genera:

*Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The plants listed can be treated in accordance with the invention in a particularly advantageous manner with the compounds of the general formula I or the inventive active ingredient mixtures. The preferred ranges stated above for the active ingredients or mixtures also apply to the treatment of these plants. Particular emphasis is given to the treatment of plants with the compounds or mixtures specifically mentioned in the present text.

If the inventive compounds are applied to the soil surface before germination, either the emergence of the weed seedlings is prevented completely or the weeds grow until they have reached the cotyledon stage, but then stop their growth and, finally, die completely after three to four weeks have elapsed.

When the active ingredients are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the inventive compounds display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, are damaged only to an insignificant extent, or not at all, depending on the structure of the respective inventive compound and its application rate. This is why the present compounds are highly suitable for the selective control of undesired vegetation in plant crops such as agriculturally useful plants or ornamentals.

Moreover, the inventive compounds (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since for example lodging can be reduced, or prevented completely, hereby.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated in accordance with the invention. Plant cultivars should be understood to mean plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

Owing to their herbicidal and plant-growth-regulatory properties, the active ingredients can also be employed for controlling harmful plants in crops of known genetically modified plants or genetically modified plants which are yet to be developed. As a rule, the transgenic plants are distinguished by especially advantageous properties, for example by resistances to certain pesticides, mainly certain herbicides, resistances to plant diseases or causative organisms of plant diseases, such as certain insects, nematodes or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known. Further particular properties may be tolerance or resistance to abiotic stresses, for example heat, cold, drought, salt and ultraviolet radiation. The active ingredients can also be used in transgenic plants which are notable for higher yields, for example for improved photosynthesis performance or improved nutrient uptake.

It is preferred to use the inventive compounds of the formula (I) or salts thereof in economically important transgenic crops of useful plants and ornamentals, for example of cereals such as wheat, barley, rye, oats, sorghum and millet, rice, cassava and maize or else crops of sugar beet, cotton, soya bean, oilseed rape, potato, tomato, peas and other vegetables.

It is preferred to employ the compounds of the formula (I) as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP 0221044, EP 0131624). For example, the following have been described in several cases:

recombinant modifications of crop plants for the purpose of modifying the starch synthesized in the plants (for example WO 92/011376 A, WO 92/14827 A, WO 91/19806 A), transgenic crop plants which are resistant to certain herbicides of the glufosinate type (cf., for example, EP 0242236 A, EP 242246 A) or of the glyphosate type (WO 92/000377 A) or of the sulphonylurea type (EP 0257993 A, U.S. Pat. No. 5,013,659), or are resistant to combinations or mixtures of these herbicides by virtue of "gene stacking", such as transgenic crop plants, for example maize or soya with the trade name or the designation Optimum™ GAT™ (Glyphosate ALS Tolerant). Additionally described have been transgenic plants which are resistant to synthetic auxins (e.g. 2,4 D), HRAC mode of action Class O and aryloxy-phenoxy propionate (fops, HRAC, Class A) (DHT, Dow Agroscience Herbicide Tolerance Trait)

transgenic crop plants, for example cotton which is capable of producing *Bacillus thuringiensis* toxins (Bt toxins), which make the plants resistant to certain pests (EP 0142924 A, EP 0193259 A), transgenic crop plants with a modified fatty acid composition (WO 91/13972 A), genetically modified plants which have new insect resistances, for example based on the expression of toxins from *Photorhabdus, Xenorhabdus* symbionts from entomopathogenic nematodes and toxins from spiders, scorpions, ants, parasitic wasps, genetically modified crop plants with novel constituents or secondary metabolites, for example novel phytoalexins, which bring about an increased disease resistance (EP 309862 A, EP0464461 A), genetically modified plants with reduced photorespiration which feature higher yields and higher stress tolerance (EP 0305398 A), transgenic crop plants which produce pharmaceutically or diagnostically important proteins ("molecular pharming"), transgenic crop plants which are distinguished by higher yields or better quality, transgenic crop plants which are distinguished by increased tolerances to abiotic and biotic stresses, transgenic crop plants which are distinguished by a combination, for example of the abovementioned novel properties ("gene stacking").

A large number of molecular biology techniques by means of which novel transgenic plants with modified properties can be produced are known in principle; see, for example, 1. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product.

To this end, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the inventive compounds (I) in transgenic crops which are resistant to growth regulators, for example 2, 4 D, dicamba, or to herbicides which inhibit essential plant enzymes, for example acetyl CoA carboxylases, acetolactate synthases (ALS), EPSP synthases, glutamine synthases (GS) or hydroxyphenylpyruvate dioxygenases (HPPD), or to herbicides from the group of the FOPs, sulphonylureas, glyphosates, glufosinates or benzoylisoxazoles and analogous active ingredients, or to any combinations of these active ingredients.

It is particularly preferred to employ the inventive compounds in transgenic crop plants which are resistant to a combination of glyphosates and glufosinates, glyphosates and sulphonylureas or imidazolinones. It is very particularly preferred to employ the inventive compounds in transgenic crop plants, for example maize or soya, with the trade name or the designation Optimum™ GAT™ (Glyphosate ALS Tolerant). In addition, it is particularly preferred to employ the inventive compounds in transgenic plants which are resistant to synthetic auxins (e.g. 2,4 D) with "HRAC mode of action Class O" and aryloxy-phenoxy propionate (fops) with "HRAC mode of action Class A" (e.g. DHT, Dow Agroscience Herbicide Tolerance Trait).

When the inventive active ingredients are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also provides for the use of the inventive compounds of the formula (I) as herbicides for controlling harmful plants in transgenic crop plants.

The inventive compounds can be used in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxiddukte" [Interface-Active Ethylene Oxide Adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active ingredients, such as, for example, insecticides, acaricides, berbicides, fungicides, and also with safeners, fertilizers and/or growth regulators, for example in the form of a finished formulation or as a tank mix.

Wettable powders are preparations which can be dispersed uniformly in water and, as well as the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleylmethyltauride. To prepare the wettable powders, the active herbicidal ingredients are ground finely, for example in customary apparatus such as hammer mills, blower mills and air-jet mills and simultaneously or subsequently mixed with the formulation assistants.

Emulsifiable concentrates are prepared by dissolving the active ingredient in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulphonates such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active ingredient onto adsorptive granulated inert material or by applying active ingredient concentrates by means of adhesives, for example polyvinyl alcohol, sodium polyacrylate or else mineral oils, onto the surface of carriers such as sand, kaolinites or of granulated inert material. It is also possible to granulate suitable active ingredients in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of inventive compounds.

In wettable powders, the active ingredient concentration is, for example, from about 10 to 90% by weight; the remainder to 100% by weight consists of customary formulation constituents. In the case of emulsifiable concentrates, the active ingredient concentration may be from about 1 to 90% by weight, preferably from 5 to 80% by weight. Dust-type formulations contain from 1 to 30% by weight of active ingredient, preferably usually from 5 to 20% by weight of active ingredient; sprayable solutions contain from about 0.05 to 80% by weight, preferably from 2 to 50% by weight of active ingredient. In water-dispersible granules, the active ingredient content depends partly on whether the active compound is present in solid or liquid form and which granulation assistants, fillers, etc. are used. In the granules dispersible in water, the content of active ingredient is, for example, between 1 and 95% by weight, preferably between 10 and 80% by weight.

In addition, the active ingredient formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The inventive treatment method is preferably used on genetically modified organisms, for example plants or plant parts.

Genetically modified plants, known as transgenic plants, are plants in which a heterologous gene has been integrated stably into the genome.

The expression "heterologous gene" essentially means a gene which is provided or assembled outside the plant and which, when introduced in the nuclear, chloroplastic or mitochondrial genome, gives the transformed plant new or improved agronomic or other properties by expressing a protein or polypeptide of interest or by downregulating or silencing other gene(s) which are present in the plant (using for example antisense technology, cosuppression technology or RNA interference [RNAi] technology). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active ingredients and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active ingredient combinations according to formula (I) may also have a strengthening effect in plants. Accordingly, they are suitable for mobilizing the defense system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are understood as mean, in the present context, also those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood to mean phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active ingredients.

Plants which are also preferably treated in accordance with the invention are resistant to one or more biotic stress factors, i.e. said plants have an improved defense against animal and microbial pests, such as nematodes, insects, mites, phytopathogenic fungi, bacteria, viruses and/or viroids.

In addition to the aforementioned plants and plant varieties, it is also possible in accordance with the invention to treat those which are resistant to one or more abiotic stress factors.

Abiotic stress conditions may include, for example, drought, cold exposure, heat exposure, osmotic stress, waterlogging, increased soil salinity, increased exposure to minerals, ozone conditions, strong light conditions, limited availability of nitrogen nutrients, limited availability of phosphorus nutrients or shade avoidance.

Plants and plant varieties which may also be treated in accordance with the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated in accordance with the invention are hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated in accordance with the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such, EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the above-mentioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme of prephenate dehydrogenase in addition to a gene encoding an HPPD-tolerant enzyme.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Further herbicide-resistant plants are plants which have been rendered tolerant to ACCase inhibitors.

Further plants tolerant to imidazolinone and/or sulphonylurea can be obtained by induced mutagenesis, selection in cell cultures in the presence of the herbicide or mutation breeding.

Plants or plant varieties (obtained by plant biotechnology methods such as genetic engineering) which may also be treated in accordance with the invention are insect-resistant transgenic plants, i.e. plants made resistant to attack by certain target insects. Such plants can be obtained by genetic transformation, or by selection of plants containing a mutation imparting such insect resistance.

The term "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, e.g. proteins of the Cry protein classes Cry1Ab, Cry1Ac, Cry1F, Cry2Ab, Cry3Ae, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by corn event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb1 protein in corn events MON863 or MON88017, or the Cry3A protein in corn event MIR 604;
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g. proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated in accordance with the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants.
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may likewise be treated in accordance with the invention have an altered quantity, quality and/or storage stability of the harvested product and/or altered properties of specific ingredients of the harvested product, for example:

1) transgenic plants which synthesize a modified starch whose physicochemical characteristics, in particular the amylose content or the amylose/amylopectin ratio, the degree of branching, the average chain length, the side chain distribution, the viscosity behaviour, the gelling strength, the starch grain size and/or the starch grain morphology, is altered compared to the synthesized starch in wild type plant cells or plants, such that this modified starch is better suited for certain applications.

2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan.
3) transgenic plants which produce hyaluronan.

Plants or plant cultivars (which can be obtained by plant biotechnology methods such as genetic engineering) which may likewise be treated in accordance with the invention are plants, such as cotton plants, with altered fibre characteristics. Such plants can be obtained by genetic transformation, or by selection of plants containing a mutation imparting such altered fibre characteristics and include:
  a) plants, such as cotton plants, which contain an altered form of cellulose synthase genes;
  b) plants, such as cotton plants, which contain an altered form of rsw2 or rsw3 homologous nucleic acids;
  c) plants, such as cotton plants, with an increased expression of sucrose phosphate synthase;
  d) plants, such as cotton plants, with an increased expression of sucrose synthase;
  e) plants, such as cotton plants, wherein the timing of the plasmodesmatal gating at the basis of the fibre cell is altered, for example through downregulation of fibre-selective β-1,3-glucanase;
  f) plants, such as cotton plants, which have fibres with altered reactivity, for example through the expression of the N-acetylglucosaminetransferase gene including nodC and chitin synthase genes.

Plants or plant cultivars (that can be obtained by plant biotechnology methods such as genetic engineering) which may also be treated in accordance with the invention are plants, such as oilseed rape or related *Brassica* plants, with altered oil profile characteristics. Such plants can be obtained by genetic transformation or by selection of plants containing a mutation imparting such altered oil characteristics and include:
  a) plants, such as oilseed rape plants, which produce oil having a high oleic acid content;
  b) plants, such as oilseed rape plants, which produce oil having a low linolenic acid content;
  c) plants, such as oilseed rape plants, which produce oil having a low level of saturated fatty acids.

Particularly useful transgenic plants which may be treated in accordance with the invention are plants which comprise one or more genes which encode one or more toxins, are the following which are sold under the trade names: YIELD GARD® (for example maize, cotton, soya beans), Knock-Out® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated in accordance with the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

The term "active ingredients" or "compounds" always also includes the active ingredient combinations mentioned here too.

PREPARATION EXAMPLES
Example (I-1-a-1)

Method A

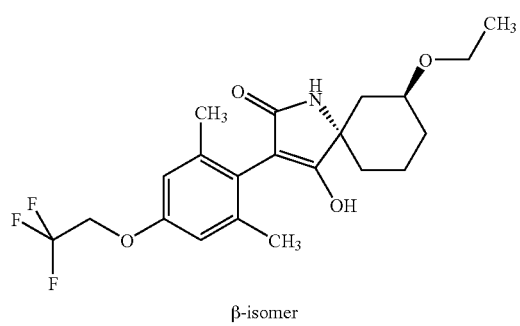 [SMILES: CCO[C@H]1CCC[C@@]2(C1)NC(=O)C(c1c(C)cc(OCC(F)(F)F)cc1C)=C2O]

β-isomer 0.41 g (0.58 mmol) of the compound according to example II-1-a-1 in a solution of 2 ml of DMF is added dropwise at room temperature within 30 min to a solution of 5 ml of DMF and 164 mg (2.5 eq) of potassium t-butoxide, and stirred at this temperature for 18 h. The mixture is adjusted to pH=1 with 1N hydrochloric acid and the residue obtained is filtered off. Column chromatography purification (RP-silica gel, acetonitrile/water gradient) gives the inventive product (I-1-a-1)=200 mg (38% of theory).

$^1$H NMR (400 MHz, d$_6$-DMSO): δ=6.75 (s, 2H, Ar—H), 4.70 (q, 2H, CH$_2$—CF$_3$), 3.57 (m, 1H, CH—OCH$_2$), 3.45 (m, 2H, OCH$_2$CH$_3$), 2.08 (d, 3H, ArCH$_3$), 1.98 (m), 1.70 (m), 1.29 (m, together 8H, cyclohexyl), 1.10 (t, 3H, CH$_3$) ppm.

Example I-1-a-2

Method S

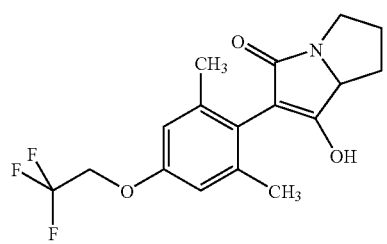 [SMILES: Cc1cc(OCC(F)(F)F)cc(C)c1C1=C(O)C2CCCN2C1=O]

0.5 g (1.55 mmol) of the compound (I-1-a-1') (known in generic terms from WO 97/02243) is admixed with 0.348 g (2 eq) of potassium t-butoxide and dissolved in 5 ml of DMA (solution 1). In addition, 0.296 g (1 eq) of copper(I) iodide and 1.35 g (6.7 eq) of 2,2,2-trifluoroethanol in 5 ml of DMA (dimethylacetamide) are suspended under inert gas and admixed with 1.17 g (6.7 eq) of potassium t-butoxide. After the exothermic reaction has ended, the mixture is admixed with solution 1 and stirred under microwave irradiation at 145° C. for 2 h. The reaction mixture is freed of the solvent under reduced pressure and admixed with 200 ml of water, and the remaining residue is removed and discarded. The aqueous phase is adjusted to pH 1 with 1N hydrochloric acid and the residue formed is filtered off. Column chromatography purification (RP-silica gel, water/acetonitrile gradient) gives 0.13 g=24% of theory of inventive compound I-1-a-2 with an m.p. of 202-205° C.

In analogy to example (I-1-a-1) and example (I-1-a-2), and according to the general information regarding preparation, the following compounds of the formula (I-1-a) are obtained:

(I-1-a)

[Structure of compound I-1-a with substituents W, X, Y, Z on phenyl ring, and A, B, D groups on pyrrolidinone ring with OH group; Z = CJ²J¹-CH₂-OJ³]

| Ex. No. | W | X | Y | Z | J¹ | J² | J³ | D | A | B | Analysis | Isomer |
|---|---|---|---|---|---|---|---|---|---|---|---|---|
| I-1-a-3 | CH₃ | C₂H₅ | H | 4- | F | F | F | H | | —(CH₂)₂—CH(OCH₃)—(CH₂)₂— | 1H-NMR (400 MHz, CDCl₃): 4.34 (q, 2H, CH₂—CF₃), 3.23 (m, 1H, CH—OCH₃) | cis |
| I-1-a-4 | C₂H₅ | C₂H₅ | H | 4- | F | F | F | H | | —(CH₂)₂—CH(OCH₃)—(CH₂)₂— | 1H-NMR (400 MHz, CDCl₃): 4.47 (q, 2H, CH₂—CF₃), 3.29 (m, 1H, CH—OCH₃) | cis |
| I-1-a-5 | CH₃ | C₂H₅ | H | 4- | F | F | F | H | | —CH₂—CH(OCH₂CH₃)—(CH₂)₃— | 1H-NMR (400 MHz, CDCl₃): 4.32 (q, 2H, CH₂—CF₃), 3.86 (m, 1H, CH—OCH₂) | trans |
| I-1-a-6 | CH₃ | C₂H₅ | H | 4- | F | F | F | H | | —(CH₂)₂—C(—OCH₂—CH₂O—)—(CH₂)₂— | 1H-NMR (400 MHz, CDCl₃): 4.34 (q, 2H, CH₂—CF₃), 3.96 (m, 4H, OCH₂CH₂O) | |
| I-1-a-7 | CH₂ | C₂H₅ | H | 4- | F | F | F | H | | —(CH₂)₂—C(—OCH₂—CH(CH₃)—O—)—(CH₂)₂— | 1H-NMR (400 MHz, CDCl₃): 4.33 (q, 2H, CH₂—CF₃), 1.27 (dd, 3H, OCHCH₃) | |
| I-1-a-8 | CH₃ | C₂H₅ | H | 4- | F | F | F | H | | —(CH₂)₂—CH(CH₃)—(CH₂)₂— | 1H-NMR (400 MHz, CDCl₃): 4.34 (q, 2H, CH₂—CF₃), 0.97 (d, 3H, CH—CH₃) | |
| I-1-a-9 | C₂H₅ | C₂H₅ | H | 4- | F | F | F | H | CH₃ | | 1H-NMR (400 MHz, d₆-DMSO): 3.43 (m, 4H, CH₂—O and CH₂—CF₃) | |
| I-1-a-10 | CH₃ | C₂H₅ | H | 4- | F | F | F | H | | —(CH₂)₂—C(—O—CH(CH₃)—CH₂—CH(CH₃)—O—)—(CH₂)₂— | 1H-NMR (400 MHz, CDCl₃): 4.33 (q, 2H, CH₂—CF₃), 4.08 and 3.93 (each m, each 1H, OCHCH₃) | trans:cis approx. 4:1 |
| I-1-a-11 | CH₃ | C₂H₅ | H | 4- | F | F | F | H | C₂H₅ | | 1H-NMR (400 MHz, CDCl₃): 4.34 (q, 2H, CH₂—CF₃), 0.90 (t, 3H CH₂—CH₃) | |
| I-1-a-12 | CH₃ | C₂H₅ | H | 4- | F | F | F | H | | —CH₂—CH(CH₂—OCH₃)—(CH₂)₃— | 1H-NMR (400 MHz, CDCl₃): 4.34 (q, 2H, CH₂—CF₃), 3.36 (m, CH₂—O—CH₃) | trans |
| I-1-a-13 | CH₃ | C₂H₅ | H | 4- | F | F | F | H | | —CH₂—CH(OCH₃)—(CH₂)₃— | 1H-NMR (400 MHz, CDCl₃): 4.33 (q, 2H, CH₂—CF₃), 3.73 (m, CH—O—CH₃) | trans |
| I-1-a-14 | CH₃ | C₂H₅ | H | 4- | F | F | F | H | | —CH₂—CH(OC₃H₇)—(CH₂)₃— | 1H-NMR (400 MHz, CDCl₃): 4.34 (q, 2H, CH₂—CF₃), 3.86 (m, CH—O—CH₂) | trans |
| I-1-a-15 | CH₃ | C₂H₅ | H | 4- | F | F | F | H | CH₃ | | 1H-NMR (400 MHz, CDCl₃): 4.34 (q, 2H, CH₂—CF₃), 3.86 (m, CH—O—CH₂) | |
| I-1-a-16 | CH₃ | C₂H₅ | H | 4- | F | F | F | H | | —(CH₂)₂—CH(CH₂—OCH₃)—(CH₂)₂— | 1H-NMR (400 MHz, CDCl₃): 4.34 (q, 2H, CH₂—CF₃) | |
| I-1-a-17 | CH₃ | CH₃ | H | 4- | F | F | F | H | | —(CH₂)₂—CH(CH₃)—(CH₂)₂— | 1H-NMR (400 MHz, d₆-DMSO): 4.66 (q, 2H, CH₂—CF₃), 3.14 (d, CH₂—O—CH₃), 1.45 (d, 6H, C(CH₃)₂) | β |
| I-1-a-18 | CH₃ | CH₃ | H | 4- | F | F | F | H | | —(CH₂)₂—CH(CH₃)—(CH₂)₂— | 1H-NMR (400 MHz, d₆-DMSO): 4.68 (q, | β |

-continued (I-1-a)

where Z =

| Ex. No. | W | X | Y | Z | J¹ | J² | J³ | D | A | B | Analysis | Isomer |
|---|---|---|---|---|---|---|---|---|---|---|---|---|
| I-1-a-19 | CH₃ | CH₃ | H | 4- | F | F | F | H | | —CH₂—CH(OC₃H₇)—(CH₂)₃— | 2H, CH₂—CF₃), 0.91 (d, CH—CH₃) | trans |
| I-1-a-20 | CH₃ | CH₃ | H | 4- | F | F | F | H | —(CH₂)₄— | H | 1H-NMR (400 MHz, d₆-DMSO): 7.65 (q, 2H, CH₂—CF₃), 3.33 (m, CH—O—CH₂) | |
| I-1-a-21 | CH₃ | C₂H₅ | H | 4- | F | F | F | H | —(CH₂)₃— | H | 1H-NMR (400 MHz, d₆-DMSO): 4.68 (q, 2H, CH₂—CF₃), 4.05 (m, CH—N) | |
| I-1-a-22 | CH₃ | C₂H₅ | H | 4- | F | F | F | H | —(CH₂)₄— | H | 1H-NMR (400 MHz, d₆-DMSO): 4.68 (q, 2H, CH₂—CF₃), 4.15 (m, CH—N) | |
| I-1-a-23 | H | C₂H₅ | H | 4- | F | F | F | H | | —(CH₂)₂—CHOCH₃—(CH₂)₂— | 1H-NMR (400 MHz, d₆-DMSO): 4.68 (q, 2H, CH₂—CF₃), 4.05 (m, CH—N) | β |
| I-1-a-24 | C₂H₅ | Cl | H | 4- | F | F | F | H | | —CH₂—CH(OC₄H₉)—(CH₂)₃— | 1H-NMR (300 MHz, CDCl₃): 4.34 (q, 2H, O—CH₂—CF₃), 3.16 (m, 1H, CH—O—CH₃) | trans |
| I-1-a-25 | CH₃ | CH₃ | H | 4- | F | F | F | H | | —CH₂—CH(OCH₃)—(CH₂)₂— | | cis |
| I-1-a-26 | CH₃ | CH₃ | H | 4- | F | F | F | H | | —(CH₂)₂—O—(CH₂)₂— | 1H-NMR (400 MHz, d₆-DMSO): 1.43-1.60 (m, 4H, CH₂), 1.88-2.00 (m, 4H, CH₂), 2.06 (s, 6H, 2 × Ar—CH₃), 3.27 (s, 3H, OCH₃), 4.61-4.66 (q, 2H, OCH₂CF₃), 6.73 (s, 2H, ArH) | — |
| I-1-a-27 | H | CH₃ | H | 5- | F | F | F | H | | —(CH₂)₂—CH(OCH₃)—(CH₂)₂— | 1H-NMR (400 MHz, d₆-DMSO): 1.27-1.30(2m, 2H, CH₂), 2.07 (s, 6H, 2 × Ar—CH₃), 3.67-3.73 (zt, 2H, OCH₂), 3.82-3.87 (m, 2H, OCH₂), 4.62-4.69 (q, 2H, OCH₂CF₃), 6.74 (s, 2H, ArH) | cis |
| I-1-a-28 | CH₃ | CH₃ | H | 3- | F | F | F | H | | —(CH₂)₂—CH(OC₂H₅)—(CH₂)₂— | 1H-NMR (400 MHz, d₆-DMSO): 1.97 (s, 3H, Ar—CH₃), 3.27 (s, 3H, OCH₃), 4.59-4.66 (m, 2H, CH₂CF₃), 6.75 (d, 1H, ArH), 6.86-6.89 (m, 1H, ArH), 7.13 (d, 1H, ArH) | cis |
| I-1-a-29 | CH₃ | CH₃ | H | 3- | F | F | F | H | | —(CH₂)₂—CH(OCH₃)—(CH₂)₂— | 1H-NMR (400 MHz, d₆-DMSO): 1.11 (t, 3H, CH₃—CH₂O), 1.97, 2.03 (2s, each 3H, ArCH₃), 3.47-3.52 (q, 2H, O—CH₂CH₃), 4.58-4.65 (q, 2H, O—CH₂CF₃), 6.92 (d, 1H, ArH), 6.99 (d, 1H, ArH) | cis/trans approx. 10:1 |
| | | | | | | | | | | | 1H-NMR (400 MHz, d₆-DMSO): 1.97 2.03 (2s, each 3H, Ar—CH₃), 3.27 (s, 3H, OCH₃), 4.58-4.65 (m, 2H, O—CH₂CF₃), | |

-continued (I-1-a)

where Z = [structure with J², J¹, J³, 5, O]

| Ex. No. | W | X | Y | Z | J¹ | J² | J³ | D | A | B | Analysis | Isomer |
|---|---|---|---|---|---|---|---|---|---|---|---|---|
| I-1-a-30 | H | CH₃ | H | 5- | F | F | F | H | | —(CH₂)₂—O—(CH₂)₂— | 6.90 (d, 1H, ArH), 6.99 (d, 1H, ArH) 1H-NMR (400 MHz, d₆-DMSO): 3.59-3.69 (m, 2H, OCH₂), 3.81-3.85 (m, 2H, OCH₂), 4.54-4.61 (m, 2H, O—C$\underline{H_2}$CF₃), 6.74-6.76 (m, 1H, ArH), 6.82-6.83 (d, 1H, ArH), 7.04-7.06 (d, 1H, ArH) | — |
| I-1-a-31 | CH₃ | CH₃ | H | 3- | F | F | F | H | | —(CH₂)₂—O—(CH₂)₂— | 1H-NMR (400 MHz, d₆-DMSO): 1.28-1.33 (m, 2H, CH₂—CH₂—O), 1.98, 2.04 (2s, each 3H, ArCH₃), 3.67-3.74 (m, 2H, O—CH₂), 3.84-3.88 (m, 2H, O—CH₂), 4.59-4.65 (m, 2H, O—C$\underline{H_2CF_3}$) | — |
| I-1-a-32 | CH₃ | CH₃ | H | 4- | F | F | F | H | | —(CH₂)₂—COCH₃—(CH₂)₂—<br>|<br>C₂H₅ | 269 | Mixture |
| I-1-a-33 | CH₃ | CH₃ | H | 4- | F | F | F | H | | —CH₂—CH—(CH₂)₂—<br>|<br>CH₂—OCH₃ | 190-193 | cis |
| I-1-a-34 | CH₃ | CH₃ | H | 4- | F | F | F | H | | —CH₂—CH—(CH₂)₂—<br>|<br>CH₂OCH₃ | 94-100 | trans |
| I-1-a-35 | CH₃ | C₂H₅ | H | 4- | F | F | F | H | | —CH₂—CH—(CH₂)₂—<br>|<br>CH₂OCH₃ | d) | trans |
| I-1-a-36 | CH₃ | CH₃ | H | 4- | F | F | F | H | | —(CH₂)₂—COCH₃—(CH₂)₂—<br>|<br>CH₃ | a) | trans |

-continued (I-1-a)

where Z = [structure with J², J³, J¹, and position 5 with O]

| Ex. No. | W | X | Y | Z | J¹ | J² | J³ | D | A | B | Analysis | Isomer |
|---|---|---|---|---|---|---|---|---|---|---|---|---|
| I-1-a-37 | CH₃ | C₂H₅ | H | 4- | F | F | F | H | | —(CH₂)₂—COCH₃—(CH₂)—<br>　　　　　　　　　｜<br>　　　　　　　　　CH₃ | 196 | cis |
| I-1-a-38 | CH₃ | C₂H₅ | H | 4- | F | F | F | H | | —(CH₂)₂—COCH₃—(CH₂)—<br>　　　　　　　　　｜<br>　　　　　　　　　CH₃ | 189 | trans |
| I-1-a-39 | CH₃ | CH₃ | H | 4- | F | F | F | H | | —(CH₂)₂—CH—(CH₂)₂—<br>　　　　　　｜<br>　　　　　　OCH₂CF₃ | 258-264 | Mixture β |
| I-1-a-40 | CH₃ | C₂H₅ | H | 4- | F | F | F | H | | —(CH₂)₂—CH—(CH₂)₂—<br>　　　　　　｜<br>　　　　　　CH₂OCH₃ | 236 | Mixture β |
| I-1-a-41 | CH₃ | C₂H₅ | H | 4- | F | F | F | H | | —CH₂—CH—(CH₂)₂—<br>　　　　　｜<br>　　　　　CH₂OCH₃ | e) | cis |
| I-1-a-42 | H | CH₃ | H | 4- | F | F | F | H | | —(CH₂)₂—CHOCH₃—(CH₂)₂ | 101-102 | cis |
| I-1-a-43 | CH₃ | CH₃ | H | 3- | F | F | F | H | | —(CH₂)₂—COCH₃—(CH₂)₂—<br>　　　　　　　　　｜<br>　　　　　　　　　CH₃ | 139 | trans |

-continued

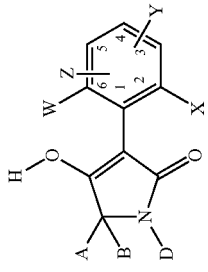
(I-1-a)

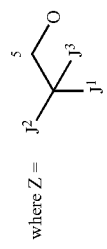
where Z =

| Ex. No. | W | X | Y | Z | J¹ | J² | J³ | D | A | B | Analysis | Isomer |
|---|---|---|---|---|---|---|---|---|---|---|---|---|
| I-1-a-44 | H | CH₃ | H | 5- | F | F | F | H | CH₃ | —CH₂—CH—(CH₂)₂—<br>          CH₂OCH₃ | b) | cis |
| I-1-a-45 | H | CH₃ | H | 5- | F | F | F | H | CH₃ | —CH₂—CH—(CH₂)₂—<br>          CH₂OCH₃ | c) | trans |
| I-1-a-46 | CH₃ | C₂H₅ | H | 4- | F | F | F | H | —CH₂—C(—O—CH₂—<br>     CH₂—O—)—CH₂— | | 201-204 | H | a) $^1$H NMR (400 MHz, d₆-DMSO): δ = 1.09 (s, 3H, CH₃), 1.12-1.15 (dm, 2H, CH₂), 1.61-1.69 (tm, 2H, CH₂), 1.74-1.78 (dm, 2H, CH₂), 2.06 (s, 6H, ArCH₃), 3.11 (s, 3H, OCH₃), 4.61-4.68 (q, 2H, OCH₂CF₃), 6.73 (s, 2H, ArH), 7.81 (br, 1H, NH) ppm
b) $^1$H NMR (600 MHz, d₆-DMSO): δ = 1.12 (t, 3H, CH₂CH₃), 1.43-1.64 (3m, 3H), 2.21-2.25 (m, 1H), 2.34-2.36 (m, 1H), 3.32-3.45 (2m, 4H), OCH₂—CH₂—O—CH₂), 4.66-4.70 (q, 2H, OCH₂CF₃), 6.75 (d, 1H, ArH), 6.88-6.90 (m, 1H, ArH), 7.14-7.15 (d, 1H, ArH), 7.79 (sbr, 1H, NH)
c) $^1$H NMR (400 MHz, d₆-DMSO): δ = 1.11 (t, 3H, CH₂—CH₃), 1.47-1.49 (m, 1H), 1.59-1.68 (m, 1H), 2.09 (s, 3H, Ar—CH₃), 3.22-3.36 (cm, 2H, OCH₂), 3.41-3.47 (q, 2H, OCH₂—CH₃), 4.59-4.66 (q, 2H, O—CH₂—CF₃), 6.75 (d, 1H, ArH), 6.86-6.89 (m, 1H, ArH), 7.12-7.14 (d, 1H, ArH), 7.69 (s, br, 1H, NH)
d) $^1$H NMR (400 MHz, CDCl₃): δ = 3.42 (dd, 2H, OCH₃), 4.32 (m, 2H, OCH₂CF₃)
e) $^1$H-NMR (400 MHz, CDCl₃): δ = 3.52 (dd, 2H, OCH₃), 4.32 (m, 2H, OCH₂CF₃)

Example (I-1-b-1)

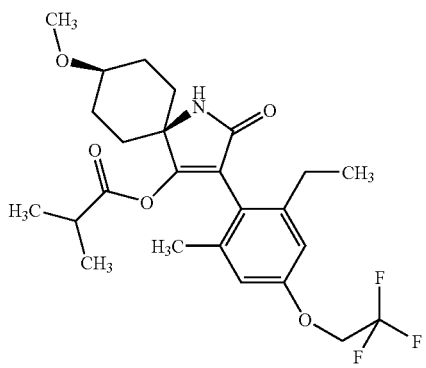 [SMILES: CCc1cc(OCC(F)(F)F)cc(C)c1C1=C(OC(=O)C(C)C)[C@]2(CC[C@H](OC)CC2)NC1=O]

Example (I-1-c-1)

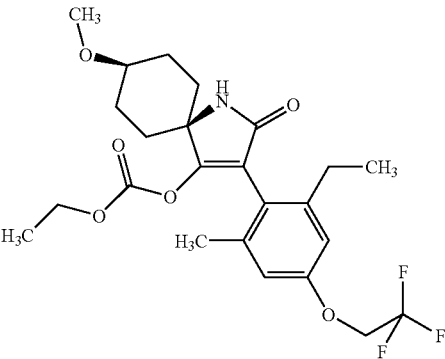

0.15 g (0.36 mmol) of the compound according to example (I-1-a-3) is initially charged with 0.44 g (1.2 eq) of triethylamine and 1.5 mg of DMAP in 8 ml of EtOAc[1]), and the mixture is stirred at 50° C. for 10 min. Subsequently 0.043 g (1.1 eq) of isobutyryl chloride in 2 ml of EtOAc[1]) is added dropwise over 20 min and then the mixture is left to stir at 50° C. for 6 h and then at RT overnight. The mixture is admixed with 10 ml of sodium hydrogencarbonate solution, the organic phase is removed, the aqueous phase is reextracted with 20 ml of EtOAc[1]), and the combined organic phases are dried over sodium sulphate. The residue which remains after the concentration is taken up in a mixture of EtOAc[1]) and n-heptane, and filtered again. This gives 0.07 g of inventive compound (I-1-b-1)=40% of theory.

$^1$H NMR (400 MHz, CDCl$_3$): δ=6.61 (pseudo d, 2H, Aryl-H), 6.37 (s, 1H, NH), 4.35 (q, 2H, CH$_2$—CF$_3$), 3.37 (s, 3H, OCH$_3$), 3.24 (m, 1H, CH—OCH$_3$), $\overline{2.51}$ (m, 3H, CH$_2$—Ar and CH(CH$_3$)$_2$), 2.20. $\overline{(s}$, 3H, ArylCH$_3$), 2.19, 1.79, 1.38 (each m, together 8H cyclohexyl), 1.13 (t, 3H, Aryl CH$_2$CH$_3$), 1.00 (dd, 6H, (CH$_3$)$_2$) ppm.
[1])Ethyl acetate In analogy to example (I-1-b-1), example (I-1-b-2) is obtained.

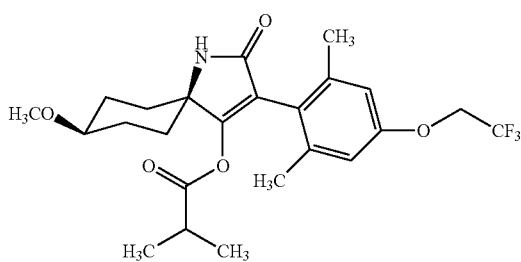

M.p. 198-199° C.

0.15 g (0.36 mmol) of the compound according to example (I-1-a-3) is initially charged with 0.44 g (1.2 eq) of triethylamine in 8 ml of dichloromethane and stirred at RT for 5 min. Subsequently, 0.043 g (1.1 eq) of ethyl chloroformate is added dropwise over 20 min and then the mixture is left to stir at RT overnight. It is admixed with 5 ml of 10% sodium carbonate solution, and the organic phase is removed and dried. The residue which remained after the concentration was purified by column chromatography (silica gel, EtOAc[1])/n-heptane gradient). This gives 0.12 g=68% of theory of inventive compound (I-1-c-1).

$^1$H NMR (400 MHz, CDCl$_3$): δ=6.66 (pseudo d, 2H, Aryl-H), 6.37 (s, 1H, NH), 4.34 (q, 21-1, C$\underline{H_2}$—CF$_3$), 4.01 (q, 2H, OCH$_2$CH$_3$), 3.40 (s, 3H, OCH$_3$), 3.25 (m, 1H, C$\underline{H}$—OCH$_3$), 2.49 (m, 2H, CH$_2$—Ar), 2.21 (s, 3H, ArylCH$_3$), 2.22, 1.96, 1.75, 1.40 (each m, together 8H cyclohexyl), 1.13 (m, 6H, aryl CH$_2$CH$_3$ and OCH$_2$CH$_3$) ppm.

In analogy to example (I-1-c-1), and according to the general information regarding preparation, the following compounds of the formula (I-1-c) are obtained:

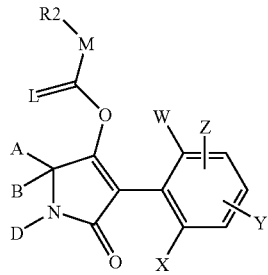

(I-1-c)

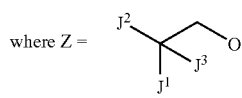

where Z =

| Ex. No. | W | X | Y | Z | $J^1$ | $J^2$ | $J^3$ | D | A | B | L | M | $R^2$ | Analysis | Isomer |
|---|---|---|---|---|---|---|---|---|---|---|---|---|---|---|---|
| I-1-c-2 | $CH_3$ | $CH_3$ | H | 4- | F | F | F | H | | —$CH_2$—CH(O$C_2H_5$)—($CH_2$)$_3$— | O | O | $C_2H_5$ | $^1$H NMR (400 MHz, CDCl$_3$): 4.34 (q, 2H, C$\underline{H}_2$—CF$_3$), 4.01 (q, 2H, OC$\underline{H}_2$), $\overline{3.42}$ (m, 3H, C$\underline{H}$—OC$\underline{H}_2$) | trans |
| I-1-c-3 | $CH_3$ | $CH_3$ | H | 4- | F | F | F | H | | —$CH_2$—CH(O$C_4H_9$)—($CH_2$)$_3$— | O | O | $C_2H_5$ | | trans |
| I-1-c-4 | $C_2H_5$ | $C_2H_5$ | H | 4- | F | F | F | H | | —($CH_2$)$_2$—CH(OCH$_3$)—($CH_2$)$_2$— | O | O | $C_2H_5$ | $^1$H NMR (400 MHz, CDCl$_3$): 4.33 (q, 2H, C$\underline{H}_2$—CF$_3$), 4.01 (q, 2H, OC$\underline{H}_2$), $\overline{3.22}$ (m, 1H, C$\underline{H}$—OCH$_3$) | cis |
| I-1-c-5 | $CH_3$ | $C_2H_5$ | H | 4- | H | F | F | H | | —($CH_2$)$_2$—CH(OCH$_3$)—($CH_2$)$_2$— | O | O | $C_2H_5$ | $^1$H NMR (400 MHz, CDCl$_3$): 4.16 (dt, 2H, C$\underline{H}_2$—CHF$_2$), 4.03 (q, 2H, OC$\underline{H}_2$), $\overline{3.23}$ (m, 1H, C$\underline{H}$—OCH$_3$) | cis |
| I-1-c-6 | $CH_3$ | $CH_3$ | H | 3- | F | F | F | H | | —($CH_2$)$_2$—CH(O$C_2H_5$)—($CH_2$)$_2$— | O | O | $C_2H_5$ | $^1$H NMR (400 MHz, d$_6$-DMSO): 0.99, 1.11 (2t, each 2H, O—CH$_2$—C$\underline{H}_3$), 1.98, 2.05 ($\overline{2s}$, each 3H, ArCH$_3$), 3.29 (zm, 1H, C$\underline{H}$OC$_2$H$_5$), $\overline{3.46}$-$\overline{3.52}$ (q, 2H, CHO—C$\underline{H}_2$CH$_3$), 3.94-3.99 (q, 2H, OCH$_2$C$\overline{H_3}$), 4.61-4.67 (m, 2H, OC$\underline{H}_2$CF$_3$) | cis |
| I-1-c-7 | $CH_3$ | $C_2H_5$ | H | 4- | F | F | F | | —$CH_2$—C(—O—$CH_2$—CH$_2$—O—)—$CH_2$— | H | O | O | $C_2H_5$ | $^1$H NMR (400 $\overline{MHz}$, CDCl$_3$): 6.70 and 6.66 (each s, 1H, Ar—H), 4.89 (s, 1H, CH—N), 4.32 (dt, 2H, CH$_2$—CF$_3$), 4.17 (q, 2H, OC$\overline{H}_2$) | |

Example II-1

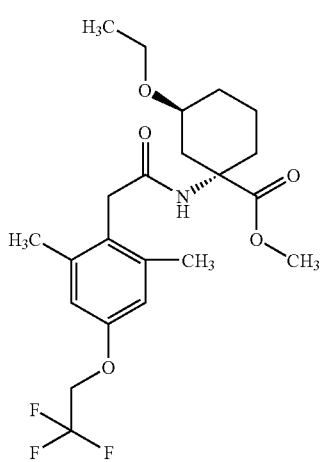

1.5 g (5.7 mmol) of the compound according to example (XXXI-1) are admixed with 3.4 g (5 eq) of thionyl chloride and one drop of DMF. The mixture is heated to boiling under reflux until the evolution of gas has ended, then the reaction solution is concentrated and admixed with 4 ml of dichloromethane (solution 1). 1.5 g (1.1 eq) of methyl trans-3-ethoxy-1-aminocyclohexancarboxylate and 0.7 g (1.2 eq) of triethylamine are dissolved in 50 ml of dichloromethane, and solution 1 is added dropwise within 1 h. After stirring for 18 h, the mixture is admixed with 10 ml of water, and the organic phase is removed, concentrated and purified by column chromatography. This gives 0.56 g (=23% of theory) of example II-a-1.

1H NMR (400 MHz, CDCl$_3$): δ=4.36 (q, 2H, CH$_2$—CF$_3$), 3.71 (s, 3H, OCH$_3$), 3.40 (m, 2H, CH—OCH$_2$) ppm.

In analogy to example (II-1), and according to the general information regarding preparation, the following compounds of the formula (II) are obtained:

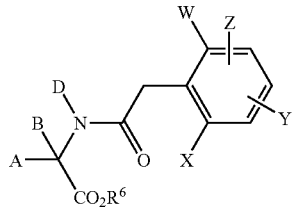

(II)

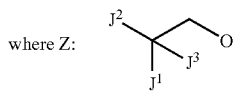

where Z:

| Ex. No. | W | X | Y | Z | J¹ | J² | J³ | D | A | B | R⁸ | Analysis | Isomer |
|---|---|---|---|---|---|---|---|---|---|---|---|---|---|
| II-2 | $CH_3$ | $CH_3$ | H | 4- | F | F | F | H |  | —$CH_2$—CH(O$C_4H_9$)—($CH_2$)$_3$— | $CH_3$ | $^1$H NMR (400 MHz, CDCl$_3$): 4.34 (q, 2H, $CH_2$—CF$_3$), 3.70 (s, 3H, OCH$_3$), 3.32 (m, 2H, CH—O$CH_2$) | trans |
| II-3 | $CH_3$ | $CH_3$ | H | 4- | F | F | F | H |  | —($CH_2$)$_2$—CH($CH_2$OCH$_3$)—($CH_2$)$_2$— | $CH_3$ | $^1$H NMR (300 MHz, CDCl$_3$): 4.34 (q, 2H, $CH_2$—CF$_3$), 3.70 (s, 3H, OCH$_3$), 3.11 (m, 2H, $CH_2$—OCH$_3$) | β |
| II-4 | $CH_3$ | $CH_3$ | H | 4- | F | F | F | H |  | —($CH_2$)$_2$—CH(OCH$_3$)—($CH_2$)$_2$— | $CH_3$ | $^1$H NMR (400 MHz, d$_6$-DMSO): 2.23 (s, 6H, Ar—CH$_3$), CH$_3$), 3.23 (s, 3H, OCH$_3$), 3.50 (s, 2H, CH$_2$CO), 3.52 (s, 3H, CO$_2$CH$_3$), 4.58-4.65 (q, 2H, O—$CH_2$CF$_3$), 6.69 (s, 2H, Ar$H$) | cis |
| II-5 | $CH_3$ | $CH_3$ | H | 4- | F | F | F | H |  | —($CH_2$)$_2$—O—($CH_2$)$_2$— | $CH_3$ | $^1$H NMR (400 MHz, d$_6$-DMSO): 1.84-1.97 (m, 4H, CH$_2$), 2.23 (s, 6H, Ar—CH$_3$), 3.51 (s, 2H, CO—CH$_2$), 3.55 (s, 3H, CO$_2$CH$_3$), 4.58-4.65 (q, 2H, Ar$H$) | — |

The following compounds of the formula (I-1'-a) which were used to prepare compounds of the formula (I-1-a) are novel and can be prepared according to method A:

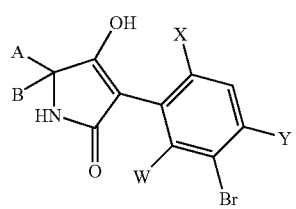

(I-1'-a)

| Ex. No. | W | X | Y | A | B | M.p. | Isomer |
|---|---|---|---|---|---|---|---|
| I-1'-a-1 | $C_2H_5$ | $C_2H_5$ | H |  | —($CH_2$)$_2$—CHOCH$_3$—($CH_2$)$_2$— | 225-228 |  |
| I-1'-a-2 | $C_2H_5$ | $C_2H_5$ | H |  | —($CH_2$)$_2$—O—($CH_2$)$_2$— | 278 | cis — |

The phenylacetic acids of the formula (XXXI') required to prepare the compound (I-1'-a) are obtained, for example, by bromination in glacial acetic acid.

Example (XXXI'-1)

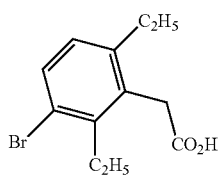
(XXXI'-1)

3.85 g (20 mmol) of 2,6-diethylphenylacetic acid are initially charged in 40 ml of glacial acetic acid. At 10° C.-15° C., 3.2 g (20 mmol) of bromine in 12 ml of glacial acetic acid are added dropwise within approx. 40 min. After approx. 2 hours, another 1.1 g of bromine in 4 ml of glacial acetic acid are added, and the mixture is stirred at room temperature overnight. After evaporating off the glacial acetic acid under reduced pressure, the residue is taken up in 40 ml of 2N sodium hydroxide solution and washed with MTB ether, and the aqueous phase is acidified, extracted with dichloromethane, dried and concentrated under reduced pressure.

This gives 4.3 g (72% of theory) of the compound (XXXI'-1).

$^1$H NMR (400 MHz, $d_6$-DMSO): δ=1.08, 1.12 (2t, each 3H, $CH_2$—$CH_3$), 2.54-2.60 (q, 2H, $CH_2CH_3$), 2.76-2.81 (q, 2H, $CH_2CH_3$), 3.70 (s, 2H, $CH_2CO$), 6.98, 7.41 (2d, each 1H, Ar—H) ppm.

Example (I-2-a-1)

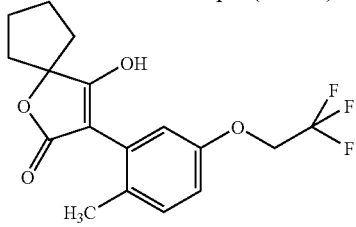
(I-2-a-1)

1.36 g (34 mmol) of sodium hydride (60%) are initially charged in 30 ml of THF, and 3.10 g (31 mmol) of trifluoroethanol are added dropwise, after the evolution of gas has ended 6.48 g (34 mmol) of copper(I) iodide are added, a solution of 2.00 g (6.18 mmol) of (I-2-a-1') (known in generic terms from WO 98/05638) dissolved in 20 ml of THF is slowly added dropwise, and the mixture is boiled at reflux for 2.5 h.

For workup, the cooled mixture is admixed with water, acidified with dil. HCl and extracted by shaking with ether and ethyl acetate, and the organic phase is dried, filtered and concentrated.

This gives 1.57 g (70% of theory) of example (I-2-a-1); log P(HCOOH) 2.59.

1H NMR ($CD_3CN$): δ=1.80-2.20 (m, 8H), 2.15 (s, 3H), 3.35 (m, 2H), 7.15 (m, 1H), 7.30 (m, 1H), 7.35 (m, 1H) ppm.

Example (I-2-a-2)

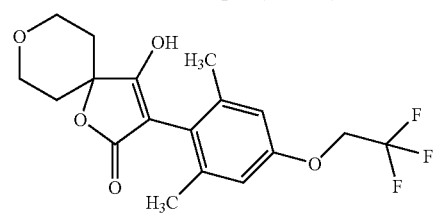 [SMILES: Cc1cc(OCC(F)(F)F)cc(C)c1C1=C(O)C2(CCOCC2)OC1=O]

0.294 g (2.62 mmol) of potassium tert-butoxide is initially charged in 7 ml of $DMF^2$ and cooled to 0° C., a solution of 0.732 g (1.75 mmol) of example (III-1) in 3 ml of $DMF^2$ is added dropwise at 0-10° C., and the mixture is stirred at room temperature overnight.

For workup, the $DMF^{2)}$ is evaporated off by rotary evaporation, the residue is stirred in water, the alkaline phase is extracted with methyl tert-butyl ether, and the aqueous phase is acidified with hydrochloric acid, extracted with dichloromethane, dried, filtered and concentrated. The crude product is purified by means of chromatography on silica gel (eluent: ethyl acetate/cyclohexane).
$^{2)}$ Dimethylformamide 0.416 g (57% of theory) of example (I-2-a-1), log P(HCOOH) 2.45.

1H NMR ($d_6$-DMSO): δ=1.50 (m, 2H), 2.10 (s, 6H), 2.20 (m, 2H), 3.65 (m, 2H), 3.95 (m, 2H), 6.80 (s, 2H) ppm.

In analogy to examples (I-2-a-1) and (I-2-a-2), and according to the general information regarding preparation, the following compounds of the formula (I-2-a) are obtained:

(I-2-a)

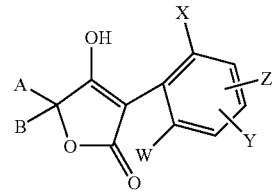

where Z = 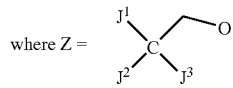

| Ex. No. | W | X | Y | Z | $J^1$ | $J^2$ | $J^3$ | A | B | Analysis | Isomer |
|---|---|---|---|---|---|---|---|---|---|---|---|
| I-2-a-3 | H | $CH_3$ | H | 3- | F | F | F | —$(CH_2)_2$—$CHOCH_3$—$(CH_2)_2$— | | a) | cis |
| I-2-a-4 | H | $CH_3$ | H | 3- | F | F | F | —$(CH_2)_2$—$CHOCH_3$—$(CH_2)_2$— | | b) | trans |
| I-2-a-5 | $CH_3$ | $CH_3$ | H | 4- | F | F | F | —$(CH_2)_2$—$CHOCH_3$—$(CH_2)_2$— | | c) | cis |
| I-2-a-6 | $CH_3$ | $CH_3$ | H | 4- | F | F | F | —$(CH_2)_2$—$CHOCH_3$—$(CH_2)_2$— | | d) | trans | a) 1H NMR($d_6$-DMSO): δ = 1.50 (m, 2H), 1.65 (m, 2H), 2.05 (m, 4H), 2.10 (s, 3H), 3.25 (m, 1H), 3.30 (s, 3H), 4.65 (m, 2H), 6.80 (m, 1H), 6.95 (m, 1H), 7.15 (m, 1H) ppm.
b) 1H NMR($d_6$-DMSO): δ = 1.40 (m, 2H), 1.70 (m, 2H), 1.95 (m, 2H), 2.10 (s, 3H), 2.15 (m, 2H), 3.30 (s, 3H), 3.50 (m, 1H), 4.65 (m, 2H), 6.80 (m, 1H), 6.95 (m, 1H), 7.15 (m, 1H) ppm.
c) 1H NMR($d_6$-DMSO): δ = 1.45 (m, 2H), 1.65 (m, 2H), 2.00 (m, 4H), 2.05 (s, 3H), 3.20 (m, 1H), 3.28 (s, 3H), 4.65 (m, 2H), 6.75 (m, 2H) ppm.
d) 1H NMR($d_6$-DMSO): δ = 1.41 (m, 2H), 1.75 (m, 2H), 1.95 (m, 2H), 2.06 (s, 3H), 2.15 (m, 2H), 3.25 (s, 3H), 3.52 (m, 1H), 4.65 (m, 2H), 6.75 (m, 2H) ppm.

Example (I-2-b-1)

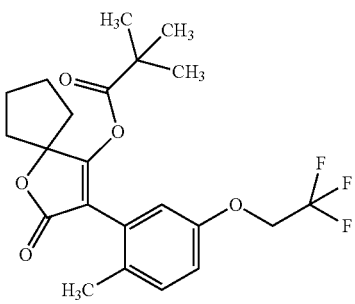 [SMILES: Cc1ccc(OCC(F)(F)F)cc1C1=C(OC(=O)C(C)(C)C)C2(CCCC2)OC1=O]

56 mg (0.16 mmol) of example I-2-a-1 are initially charged in 10 ml of dichloromethane, 18 mg (0.18 mmol) of triethylamine are added at room temperature, 21 mg (0.17 mmol) of pivaloyl chloride are added dropwise at 0-10° C. and the mixture is stirred at room temperature for 1 h.

For workup, the mixture is extracted by shaking with dil. citric acid and 5% NaOH, and the organic phase is dried and concentrated.

This gives 61 mg (83% of theory) of example (I-2-b-1), log P(HCOOH) 4.69.

1H NMR ($d_6$-DMSO): δ=1.10 (s, 9H), 1.80-2.20 (m, 81-1), 2.15 (s, 3H), 4.65 (m, 2H), 6.75 (m, 1H), 7.00 (m, 1H), 7.20 (m, 1H) ppm.

Example (III-1)

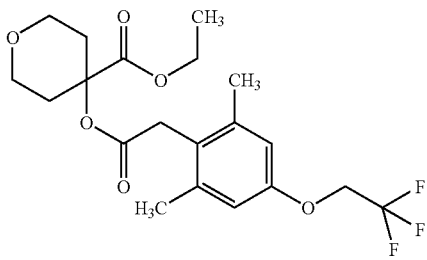 [SMILES: CCOC(=O)C1(OC(=O)Cc2c(C)cc(OCC(F)(F)F)cc2C)CCOCC1]

0.621 g (3.56 mmol) of ethyl 1-hydroxytetrahydropyrancarboxylate and 1.00 g (3.56 mmol) of 2,6-dimethyl-4-trifluoroethoxyphenylacetyl chloride are boiled under reflux in 20 ml of toluene for 12 h.

For workup, the toluene is evaporated off by rotary evaporation, the residue is partitioned between methyl t-butyl ether and 5% sodium hydroxide solution, and the organic phase is dried and concentrated.

This gives 0.732 g (47% of theory) of the compound (III-1), log P(HCOOH) 3.78.

1H NMR ($d_6$-DMSO): δ=1.15 (m, 3H), 1.80-2.00 (m, 4H), 2.25 (s, 6H), 3.40-3.70 (m, 4H), 4.05 (m, 2H), 4.65 (m, 2H), 6.75 (m, 2H) ppm.

Example I-6-a-1

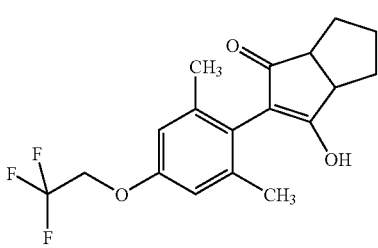 [SMILES: Cc1cc(OCC(F)(F)F)cc(C)c1C1=C(O)C2CCCC2C1=O]

300 mg (0.934 mmol) of the compound according to example (I-6'-a-1) are dissolved in 5 ml of collidine and admixed with 702 mg (6.26 mmol) of potassium tert-butoxide (solution 1). In a separate flask, 178 mg (0.934 mmol) of copper(I) iodide, 841 mg (8.4 mmol) of trifluoroethanol and 210 mg (1.87 mmol) of potassium tert-butoxide are dissolved in 5 ml of collidine. Solution 1 is added dropwise thereto, the vessel is rinsed with 2 ml of DMF and the reaction mixture is stirred at 145° C. in a microwave for 1 hour. The solvent is drawn off under reduced pressure, and the residue is taken up in water and filtered through Celite. 10 ml of ammonium chloride solution are added to the filtrate which is acidified with 2N hydrochloric acid. The solid which precipitates out is filtered off with suction and dried.

Yield: 185 mg (58% of theory).

$^1$H NMR, (400 MHz, $CDCl_3$): 1.38-1.48 (m, 1H), 1.70 (mc, 3H), 2.05 and 2.10 (each s, each 3H), 3.15 (mc, 2H), 4.31 (q, 2H), 6.65 (s, 2H) ppm.

The compound of the formula (I-6'-a-1) which is used to prepare the compound of the formula (I-6-a-1) is novel and can be prepared according to method F:

Example (I-6'-a-1)

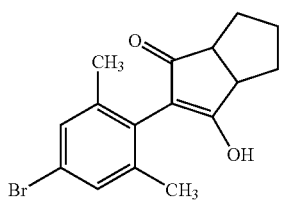

$^1$H NMR (400 MHz, $CDCl_3$): 1.43 (mc, 1H), 1.68 (mc. 3H), 2.08 and 2.11 (each s, each 3H), 2.98 and 3.28 (each mc, each 1H), 7.18 (s, 2H) ppm.

Example I-6-c-1

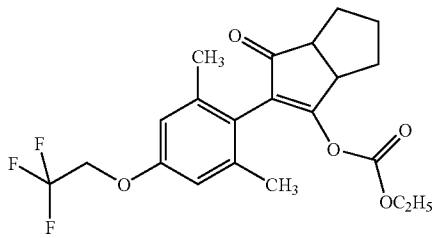 [SMILES: CCOC(=O)OC1=C(c2c(C)cc(OCC(F)(F)F)cc2C)C(=O)C2CCCC12]

69 mg (0.2 mmol) of the compound according to example (I-6-a-1) are dissolved in 5 ml of dichloromethane and admixed with 24 mg (0.22 mmol) of ethyl chloroformate and 62 mg (0.6 mmol) of triethylamine. The mixture is left at room temperature for 30 minutes. It is concentrated and purified by means of preparative HPLC (RP-18, acetonitrile/water gradient (1% trifluoroacetic acid)).

Yield: 57 mg.

$^1$H NMR (400 MHz $CDCl_3$): 1.21 (t, 3H), 1.50 (mc, 1H), 1.65-1.88 (m, 3H), 1.94 (mc, 1H), 2.06 and 2.09 (each s, each 3H), 3.11 and 3.80 (each mc, each 1H), 4.12 (mc, 2H), 4.30 (q, 2H), 6.62 (s, 2H) ppm.

Example I-8-a-1

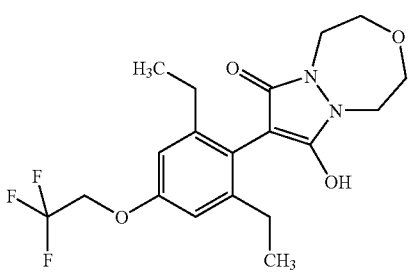 [SMILES: CCc1cc(OCC(F)(F)F)cc(CC)c1-c1c(O)n2n(c1=O)CCOCC2]

0.3 g of 8-(4-bromine-2,6-diethylphenyl)-9-hydroxy-1,2,4,5-tetrahydro-7H-pyrazolo[1,2-d][1,4,5]oxadiazepin-7-one (known from WO99/047525 ex.: 1.087) is dissolved under a nitrogen atmosphere with 2 eq (0.176 g) of potassium t-butoxide in 5 ml of collidine (solution 1).

Subsequently, 150 mg of copper(I) iodide, 0.69 g of 2,2,2-trifluoroethanol and 6.7 eq (0.591 g) of potassium t-butoxide are suspended in 5 ml of collidine under a nitrogen atomsphere. Solution 1 is added thereto and the mixture is left to stir at 145° C. for 1 h under microwave conditions.

The solvent is removed under reduced pressure and the remaining residue is taken up in water. The remaining residue is filtered off and the mother liquor is adjusted to pH=1 with 1N hydrochloric acid. After extracting with ethyl acetate and drying over sodium sulphate, the mixture is concentrated to obtain 0.275 g of inventive compound I-8-a-1.

In analogy to example (I-8-a-1), and according to the general information regarding preparation, the following compounds of the formula (I-8-a) are obtained:

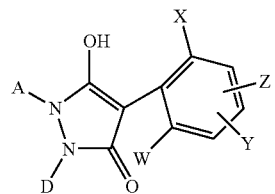

(I-8-a)

where Z = 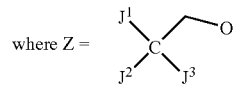

| Ex. No. | W | X | Y | Z | $J^1$ | $J^2$ | $J^3$ | A | D | Analysis |
|---|---|---|---|---|---|---|---|---|---|---|
| I-8-a-1 | $C_2H_5$ | $C_2H_5$ | H | 4- | F | F | F | | —$(CH_2)_2$—O—$(CH_2)_2$— | $^1$H NMR (400 MHz $CDCl_3$): 6.72 (m, 2H, Ar—H) 4.32 (m, 2H, $CF_3$—$CH_2$), 3.75 (m, 2H, $CH_2$—N) |
| I-8-a-2 | $C_2H_5$ | $CH_3$ | H | 4- | F | F | F | | —$(CH_2)_2$—O—$(CH_2)_2$— | $^1$H NMR (400 MHz $CDCl_3$): 6.70 (d, 1H, Ar—H) 6.60 (d, 1H, Ar—H), 4.32 m, 2H, $CF_3$—$CH_2$), 3.80 (m, 2H, $CH_2$—N) |
| I-8-a-3 | $CH_3$ | $CH_3$ | H | 4- | F | F | F | | —$(CH_2)_2$—O—$(CH_2)_2$— | $^1$H NMR (400 MHz $CDCl_3$): 6.72 (d, 1H, Ar—H) 6.62 (d, 1H, Ar—H), 4.32 (m, 2H, $CF_3$—$CF_2$), 3.82 (m, 2H), $CH_2$—N) |
| I-8-a-4 | $C_2H_5$ | $CH_3$ | H | 4- | F | F | F | | —$(CH_2)_4$— | $^1$H NMR (400 MHz $CDCl_3$): δ = 3.68 (m, 4H, $\underline{CH_2}$N), 4.32 (m, 2H, O$\underline{CH_2}$$CF_3$) |
| I-8-a-5 | $C_2H_5$ | $C_2H_5$ | H | 4- | F | F | F | | —$(CH_2)_4$— | $^1$H NMR (400 MHz $CDCl_3$): 6.68(d, 2H, Ar—H), 4.33 (m, 2H, $CF_3$—$CH_2$), 3.62 (m, 4H, $CH_2$—N) |
| I-8-a-6 | $CH_3$ | $CH_3$ | H | 4- | F | F | F | | —$(CH_2)_4$— | $^1$H NMR (400 MHz $CDCl_3$): 6.68 (d, 2H, Ar—H), 4.33 (m, 2H, $CF_3$—$CH_2$), 3.62 (m, 2H, $CH_2$—N) |

Example I-8-b-1

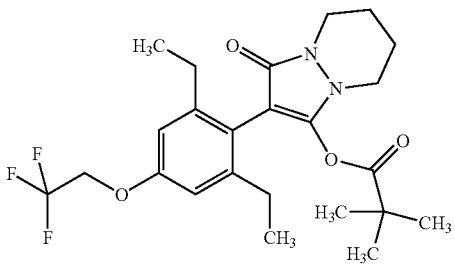 [SMILES: CCc1cc(OCC(F)(F)F)cc(CC)c1-c1c(OC(=O)C(C)(C)C)n2n(c1=O)CCCC2]

0.05 g of the compound according to example I-8-a-4 is dissolved under a nitrogen atmosphere in 1 ml of dichloromethane. Subsequently, 17 mg of 2,2-dimethylpropanoyl chloride and 17 mg of triethylamine are added, and the mixture is stirred at room temperature overnight.

The mixture is added to 5 ml of water and the phases are separated by means of an extraction cartridge. The organic phase is concentrated and then the residue is purified by reverse phase HPL chromatography (acetonitrile/water gradient, 0.05% TFA). This gives 0.024 g of inventive compound I-8-b-1.

$^1$H NMR (400 MHz, CDCl$_3$): 6.67 (s, 2H, Ar—H), 4.32 (q, 2H, OCH$_2$CF$_3$), 1.92 (m, 4H, CH$_2$), 1.05 (s, 9H, t-Bu)

In analogy to example (I-8-b-1), and according to the general information regarding preparation, the following compounds of the formula (I-8-b) are obtained:

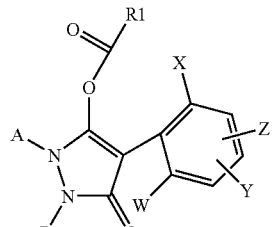

(I-8-b)

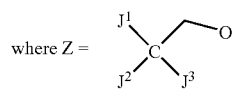

where Z =

| Ex. No. | W | X | Y | Z | J$^1$ | J$^2$ | J$^3$ | A | D | R$^1$ | Analysis |
|---|---|---|---|---|---|---|---|---|---|---|---|
| I-8-b-2 | C$_2$H$_5$ | C$_2$H$_5$ | H | 4- | F | F | F | —(CH$_2$)$_2$—O—(CH$_2$)$_2$— | | C(CH$_3$)$_3$ | a) |
| I-8-b-3 | C$_2$H$_5$ | CH$_3$ | H | 4- | F | F | F | —(CH$_2$)$_2$—O—(CH$_2$)$_2$— | | CH(CH$_3$)$_2$ | b) |
| I-8-b-4 | C$_2$H$_5$ | CH$_3$ | H | 4- | F | F | F | —(CH$_2$)$_4$— | | C(CH$_3$)$_3$ | c) |
| I-8-b-5 | CH$_3$ | CH$_3$ | H | 4- | F | F | F | —(CH$_2$)$_4$— | | CH(CH$_3$)$_2$ | d) |
| I-8-b-6 | CH$_3$ | CH$_3$ | H | 4- | F | F | F | —(CH$_2$)$_2$—O—(CH$_2$)$_2$— | | C(CH$_3$)$_3$ | e) |
| I-8-b-7 | CH$_3$ | CH$_3$ | H | 4- | F | F | F | —(CH$_2$)$_2$—O—(CH$_2$)$_2$— | | CH(CH$_3$)$_2$ | f) | a) $^1$H NMR (400 MHz, CDCl$_3$): 6.67 (s, 2H, Ar—H), 4.32 (q, 2H, OCH$_2$CF$_3$), 3.86 (m, 4H, CH$_2$—N), 1.03 (s, 9H, t-Bu)

b) $^1$H NMR (400 MHz, CDCl$_3$): 6.67 and 6.62 (each d, 1H, Ar—H), 4.32 (q, 2H, OCH$_2$CF$_3$), 2.47 (m, 1H, C<u>H</u>(CH$_3$)$_2$)

c) $^1$H NMR (400 MHz, CDCl$_3$): 6.67 and 6.62 (each d, 1H, Ar—H), 4.32 (q, 2H, OCH$_2$CF$_3$), 1.92 (m, 4H, CH$_2$), 1.09 (d, 9H, t-Bu)

d) $^1$H NMR (400 MHz, CDCl$_3$): 6.62 (s, 2H, Ar—H), 4.32 (q, 2H, OCH$_2$CF$_3$), 1.92 (m, 4H, CH$_2$), 1.05 (d, 6H, CH (C<u>H$_3$</u>)$_2$)

e) $^1$H NMR (400 MHz, CDCl$_3$): 6.62 (s, 2H, Ar—H), 4.32 (q, 2H, OCH$_2$CF$_3$), 3.88 (m, 4H, CH$_2$—N), 1.08 (s, 9H, t-Bu)

f) $^1$H NMR (400 MHz, CDCl$_3$): 6.64 (s, 2H, Ar—H), 4.32 (q, 2H, OCH$_2$CF$_3$), 3.87 (m, 4H, CH$_2$—N), 1.02 (d, 9H, CH(C<u>H$_3$</u>)$_2$)

Example I-8-c-1

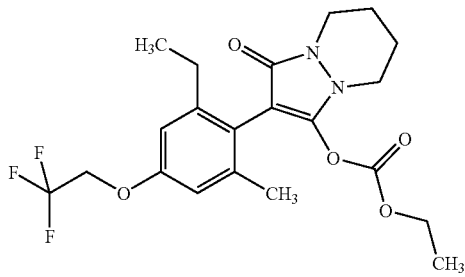 [SMILES: CCOC(=O)Oc1c(-c2c(C)cc(OCC(F)(F)F)cc2CC)c(=O)n2n1CCCC2]

0.58 g of inventive compound I-8-a-4 is dissolved in 5 ml of dichloromethane and admixed with 0.187 g of ethyl chloroformate and 0.206 g of triethylamine. The mixture is left to stir at room temperature for 18 h, and 10 ml of water are added. After extracting the aqueous phase using an extraction cartridge, the mixture is concentrated and purified by means of preparative HPLC (RP-18, acetonitrile/water gradient (1% trifluoroacetic acid)). This gives 0.03 g of inventive compound I-8-c-1.

In analogy to example (I-8-c-1), and according to the general information regarding preparation, the following compounds of the formula (I-8-c) are obtained:

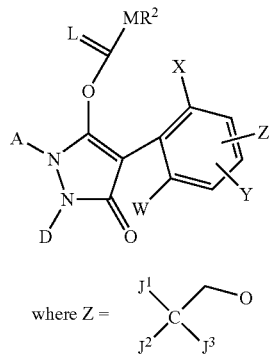

(I-8-c)

where Z =

| Ex. No. | W | X | Y | Z | $J^1$ | $J^2$ | $J^3$ | A | D | L | M | $R^2$ | Analysis |
|---|---|---|---|---|---|---|---|---|---|---|---|---|---|
| I-8-c-1 | $C_2H_5$ | $CH_3$ | H | 4- | F | F | F | | —$(CH_2)_4$— | O | O | $C_2H_5$ | a) |
| I-8-c-2 | $C_2H_5$ | $CH_3$ | H | 4- | F | F | F | | —$(CH_2)_2$—O—$(CH_2)_2$— | O | O | $C_2H_5$ | b) |
| I-8-c-3 | $C_2H_5$ | $C_2H_5$ | H | 4- | F | F | F | | —$(CH_2)_2$—O—$(CH_2)_2$— | O | O | $C_2H_5$ | c) |
| I-8-c-4 | $C_2H_5$ | $C_2H_5$ | H | 4- | F | F | F | | —$(CH_2)_4$— | O | O | $C_2H_5$ | d) |
| I-8-c-5 | $CH_3$ | $CH_3$ | H | 4- | F | F | F | | —$(CH_2)_2$—O—$(CH_2)_2$— | O | O | $C_2H_5$ | e) |
| I-8-c-6 | $CH_3$ | $CH_3$ | H | 4- | F | F | F | | —$(CH_2)_4$— | O | O | $C_2H_5$ | f) | a) $^1$H NMR (400 MHz $CDCl_3$): 6.70 (s, 1H, Ar—H), 6.67 (s, 1H, Ar—H), 4.32 (m, 2H, $CF_3$—$CH_2$), 4.14 (m, 2H, $CH_2$—OC(=O))

b) $^1$H NMR (400 MHz $CDCl_3$): 6.70 (s, 1H, Ar—H), 6.65 (d, 1H, Ar—H), 4.32 (m, 2H, $CF_3$—$CH_2$), 4.16 (m, 2H, $CH_2$—OC(=O))

c) $^1$H NMR (400 MHz $CDCl_3$): 6.68 (s, 2H, Ar—H), 4.32 (m, 2H, $CF_3$—$CH_2$), 4.14 (m, 2H, $CH_2$—OC(=O))

d) $^1$H NMR (400 MHz $CDCl_3$): 6.68 (d, 2H, Ar—H), 4.34 (m, 2H, $CF_3$—$CH_2$), 4.16 (m, 2H, $CH_2$—OC(=O))

e) $^1$H NMR (400 MHz $CDCl_3$): 6.68 (d, 2H, Ar—H), 4.30 (m, 2H, $CF_3$—$CH_2$), 4.17 (m, 2H, $CH_2$—OC(=O))

f) $^1$H NMR (400 MHz $CDCl_3$): 6.65 (d, 2H, Ar—H), 4.32 (m, 2H, $CF_3$—$CH_2$), 4.16 (m, 2H, $CH_2$—OC(=O))

2,6-Dimethyl-4-trifluoroethoxyphenylacetic acid
(Example XXXI-1)

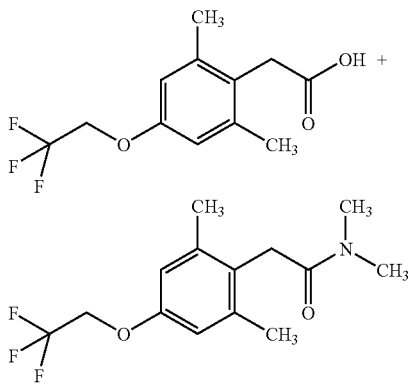

18.05 g (451 mmol) of sodium hydride are initially charged in 500 ml of DMF. 41.05 g (410 mmol) of trifluoroethanol are added dropwise, after the evolution of gas has ended 15.63 g (82 mmol) of copper(I) iodide are added, a solution of 21.10 g (82 mmol) of methyl 2,6-dimethyl-4-bromophenylacetate in 100 ml of DMF is slowly added dropwise and the mixture is boiled at reflux for 2.5 h.

For workup, the mixture is concentrated, the residue is admixed with water and extracted by shaking repeatedly with diethyl ether, and the ether phase is dried, filtered and concentrated:

12.73 g of N,N-dimethyl-2,6-dimethyl-4-trifluoroethoxyphenylacetamide.

The aqueous phase is acidified with hydrochloric acid and extracted repeatedly with dichloromethane, and the organic phase is dried and concentrated by rotary evaporation:

7.66 g or arylacetic acid.

The 12.73 g of N,N-dimethyl-2,6-dimethyl-4-trifluoroethoxyphenylacetamide are boiled in a solution of 58 g of potassium hydroxide in 165 ml of methanol and 43 ml of water for 36 h. For workup, the methanol is removed by rotary evaporation, the residue is partitioned between water and dichloromethane, the aqueous phase is acidified with hydrochloric acid and the precipitated crystals are filtered off with suction and dried. In this way, a further 11.6 g of the phenylacetic acid (XXXI-1) are obtained.

Total yield: 19.3 g (90% of theory) of 2,6-dimethyl-4-trifluoroethoxyphenylacetic acid (XXXII).

$^1$H NMR ($d_6$-DMSO): δ=2.25 (s, 6H), 3.50 (s, 2H), 4.60 (m, 2H), 6.75 (s, 2H) ppm.

log P(HCOOH) 2.51.

The log P values reported in the above tables and preparation examples are determined according to EEC Directive 79/831 Annex V.A8 by HPLC (High Performance Liquid Chromatography) on a reversed-phase column (C 18). Temperature: 43° C.

The determination is effected in the acidic range at pH 2.3 with 0.1% aqueous phosphoric acid and acetonitrile as eluent; linear gradient from 10% acetonitrile to 95% acetonitrile.

The determination by LC-MS in the acidic range is effected at pH 2.7 with 0.1% aqueous formic acid and acetonitrile (contains 0.1% formic acid) as the eluent; linear gradient from 10% acetonitrile to 95% acetonitrile.

The determination by LC-MS in the neutral range is effected at pH 7.8 with 0.001 molar aqueous ammonium hydrogen carbonate solution and acetonitrile as the eluent; linear gradient from 10% acetonitrile to 95% acetonitrile.

The calibration is effected with unbranched alkane-2-ones (with 3 to 16 carbon atoms), the log P values of which are known (determination of log P values on the basis of the retention times by linear interpolation between two successive alkanones).

The lambda-max values were determined using the UV spectra from 200 nm to 400 nm in the maxima of the chromatographic signals.

Application Examples

Example 1

| *Myzus* test (MYZUPE spray treatment) | |
|---|---|
| Solvent: | 78 parts by weight of acetone |
| | 1.5 parts by weight of dimethylformamide |
| Emulsifier: | 0.5 part by weight of alkylaryl polyglycol ether |

To prepare an appropriate active ingredient preparation, 1 part by weight of active ingredient is mixed with the stated amounts of solvent and emulsifier, and the concentrate is diluted with emulsifier-containing water to the desired concentration.

Discs of Chinese cabbage (*Brassica pekinensis*) infected by all stages of the green peach aphid (*Myzus persicae*) are sprayed with an active ingredient preparation of the desired concentration.

After the desired time, the effect in % is determined. 100% means that all of the aphids have been killed; 0% means that none of the aphids have been killed.

In this test, for example, the following compounds from the preparation examples show, at an application rate of 500 g/ha, an effect of ≧80%:

Ex. No.: I-1-a-1, I-1-a-3, I-1-a-4, I-1-a-5, I-1-a-6, I-1-a-7, I-1-a-8, I-1-a-10, I-1-a-12, I-1-a-13, I-1-a-14, I-1-a-15, I-1-a-17, I-1-a-18, I-1-a-19, I-1-a-23, I-1-a-24, I-1-a-25, I-1-a-26, I-1-a-27, I-1-a-28, I-1-a-29, I-1-a-30, I-1-a-31, I-1-a-32, I-1-a-33, I-1-a-34, I-1-a-35, I-1-a-36, I-1-a-37, I-1-a-38, I-1-a-39, I-1-a-40, I-1-a-41, I-1-a-42, I-1-a-43, I-1-a-44, I-1-a-45, I-1-a-46, I-1-a-48, I-1-b-1, I-1-c-1, I-1-c-2, I-1-c-3, I-1-c-4, I-1-c-5, I-1-c-6, I-2-a-1, I-2-a-2, I-2-a-3, I-2-a-4, I-2-a-5, I-2-a-6, I-8-a-2, I-8-b-3, I-8-b-5

In this test, for example, the following compounds from the preparation examples show, at an application rate of 20 g/ha, an effect of ≧80%:

Ex. No.: I-1-a-20

Example 2

| *Phaedon* test (PHAECO spray treatment) | |
|---|---|
| Solvent: | 78.0 parts by weight of acetone |
| | 1.5 parts by weight of dimethylformamide |
| Emulsifier: | 0.5 part by weight of alkylaryl polyglycol ether |

To prepare an appropriate active ingredient preparation, 1 part by weight of active ingredient is mixed with the stated amounts of solvent and emulsifier, and the concentrate is diluted with emulsifier-containing water to the desired concentration.

Discs of Chinese cabbage (*Brassica pekinensis*) are sprayed with an active ingredient preparation of the desired concentration and, after drying, populated with larvae of the mustard beetle (*Phaedon cochleariae*).

After the desired time, the effect in % is determined. 100% means that all beetle larvae have been killed; 0% means that none of the beetle larvae have been killed.

In this test, for example, the following compounds of the preparation examples show, at an application rate of 500 g/ha, an effect of ≧80%:

Ex. No.: I-1-a-3, I-1-a-8, I-1-a-11, I-1-a-14, I-1-a-16, I-1-a-28, I-1-a-30, I-1-a-31, I-1-a-32, I-1-a-33, I-1-c-6, I-2-a-5

Example 3

| *Tetranychus* test; OP-resistant (TETRUR spray treatment) | |
| --- | --- |
| Solvent: | 78.0 parts by weight of acetone |
| | 1.5 parts by weight of dimethylformamide |
| Emulsifier: | 0.5 part by weight of alkylaryl polyglycol ether |

To prepare an appropriate active ingredient preparation, 1 part by weight of active ingredient is mixed with the stated amounts of solvent and emulsifier, and the concentrate is diluted to the desired concentration with emulsifier-containing water.

Discs of french bean leaves (*Phaseolus vulgaris*) infested with all stages of the two-spotted spider mite (*Tetranychus urticae*) are sprayed with a preparation of the active ingredient at the desired concentration.

After the desired time, the effect in % is determined. 100% means that all spider mites have been killed and 0% means that none of the spider mites have been killed.

In this test, for example, the following compounds from the preparation examples show an effect of ≧80% at an application rate of 100 g/ha:

Ex. No.: I-1-a-4, I-1-a-5, I-1-a-6, I-1-a-7, I-1-a-8, I-1-a-10, I-1-a-14, I-1-a-17, I-1-a-2, I-1-a-25, I-1-a-28, I-1-a-3, I-1-a-30, I-1-a-31, I-1-a-32, I-1-b-1, I-1-c-2, I-1-c-3, I-1-c-4, I-1-c-5, I-1-c-6, I-2-a-5, I-2-a-6, I-2-b-1, I-8-c-1, I-8-a-2, I-8-b-3, I-8-b-5

In this test, for example, the following compounds from the preparation examples show an effect of ≧80% at an application rate of 20 g/ha:

Ex. No.: I-1-a-16, I-1-a-19

Example 4

| *Spodoptera frugiperda* test (SPODFR spray treatment) | |
| --- | --- |
| Solvent: | 78.0 parts by weight of acetone |
| | 1.5 parts by weight of dimethylformamide |
| Emulsifier: | 0.5 part by weight of alkylaryl polyglycol ether |

To prepare an appropriate active ingredient preparation, 1 part by weight of active ingredient is mixed with the stated amounts of solvent and emulsifier, and the concentrate is diluted with emulsifier-containing water to the desired concentration.

Discs of maize leaves (*Zea mays*) are sprayed with an active ingredient preparation of the desired concentration and, after drying, populated with caterpillars of the army worm (*Spodoptera frugiperda*).

After the desired time, the effect in % is determined. 100% means that all caterpillars have been killed; 0% means that none of the caterpillars have been killed.

In this test, for example, the following compounds from the preparation examples show, at an application rate of 500 g/ha, an effect of ≧80%:

Ex. No.: I-1-a-27, I-1-a-28, I-1-a-32, I-1-a-36, I-1-a-39, I-1-c-1

Example 5

| *Meloidogyne incognita* test (MELGIN) | |
| --- | --- |
| Solvent: | 78.0 parts by weight of acetone |
| | 1.5 parts by weight of dimethylformamide |
| Emulsifier: | 0.5 part by weight of alkylaryl polyglycol ether |

To prepare an appropriate active ingredient preparation, 1 part by weight of active ingredient is mixed with the stated amounts of solvent and emulsifier, and the concentrate is diluted to the desired concentration with water.

Vessels are filled with sand, solution of active ingredient, *Meloidogyne incognita* egg/larvae suspension and lettuce seeds. The lettuce seeds germinate and the plants develop. On the roots, galls are formed.

After the desired time, the nematicidal effect is determined by the gall formation in %. 100% means that no galls were found; 0% means that the number of galls on the treated plants corresponds to that of the untreated control.

In this test, for example, the following compounds from the preparation examples show an effect of ≧80% at an application rate of 20 ppm:

Ex. No.: I-1-a-25, I-1-c-6

Example 6

| *Lucilia cuprina* test (LUCICU) | |
| --- | --- |
| Solvent: | dimethyl sulphoxide |

To prepare an appropriate active ingredient preparation, 1 part by weight of active ingredient is mixed with the stated amount of solvent, and the concentrate is diluted to the desired concentration with water.

Vessels containing horse meat treated with the active ingredient preparation of the desired concentration are populated with *Lucilia cuprina* larvae.

After the desired time, the kill in % is determined. 100% means that all of the larvae have been killed; 0% means that none of the larvae have been killed.

In this test, for example, the following compounds from the preparation examples show, at an application rate of 100 ppm, an effect of ≧ 80%:

Ex. No.: I-1-a-25, I-1-a-3, I-2-a-5, I-2-a-6

Example 7

| *Boophilus microplus* test (BOOPMI injection) | |
|---|---|
| Solvent: | dimethyl sulphoxide |

To prepare an appropriate active ingredient preparation, 1 part by weight of active ingredient is mixed with the stated amount of solvent, and the concentrate is diluted to the desired concentration with water. The solution of active ingredient is injected into the abdomen (*Boophilus microplus*), and the animals are transferred into dishes and kept in a climate-controlled room. The activity is assessed by laying of fertile eggs.

After the desired time, the effect in % is determined. 100% means that none of the ticks has laid any fertile eggs.

In this test, for example, the following compounds from the preparation examples show, at an application rate of 20 ppm, an effect of ≧80%:

Ex. No.: I-1-a-25, I-1-a-3, I-1-a-7, I-1-c-4, I-1-c-5, I-2-a-5, I-2-a-6

Example 8

Enhancement of Activity by Ammonium/Phosphonium Salts in Combination with Penetration Enhancers

| *Myzus persicae* test | |
|---|---|
| Solvent: | 7 parts by weight of dimethylformamide |
| Emulsifier: | 1 part by weight of alkylaryl polyglycol ether |

To prepare an appropriate active ingredient preparation, 1 part by weight of active ingredient is mixed with the stated amounts of solvent and emulsifier, and the concentrate is diluted to the desired concentration with water. For application with ammonium or phosphonium salts and penetration enhancer (rapeseed oil methyl ester 500 EW), these are each added to the spray liquor in a concentration of 1000 ppm.

Bell pepper plants (*Capsicum annuum*) heavily infested by the green peach aphid (*Myzus persicae*) are treated by spraying to runoff point with the active ingredient preparation of the desired concentration. After the desired time, the kill in % is determined. 100% means that all animals have been killed; 0% means that none of the animals have been killed.

TABLE

| | | Kill rate/% after 6 days | | | |
|---|---|---|---|---|---|
| Active ingredient | Concentration/ ppm | | +AS (1000 ppm) | +RME (1000 ppm) | +RME + AS (1000 ppm each) |
| I-1-a-25 | 0.8 | 0 | 0 | 40 | 55 |

Example 9

| *Aphis gossypii* test | |
|---|---|
| Solvent: | 7 parts by weight of dimethylformamide |
| Emulsifier: | 1 part by weight of alkylaryl polyglycol ether |

To prepare an appropriate active ingredient preparation, 1 part by weight of active ingredient is mixed with the stated amounts of solvent and emulsifier, and the concentrate is diluted to the desired concentration with emulsifier-containing water. For application with ammonium or phosphonium salts and penetration enhancers (rapeseed oil methyl ester 500 EW), these are each added to the spray liquor in a concentration of 1000 ppm.

Cotton plants (*Gossypium hirsutum*) heavily infested by the cotton aphid (*Aphis gossypii*) are treated by spraying to runoff point with the active ingredient preparation of the desired concentration.

After the desired time, the kill in % is determined. 100% means that all the aphids have been killed; 0% means that none of the aphids have been killed.

TABLE

| | | Kill rate/% after 6 days | | |
|---|---|---|---|---|
| Active ingredient | Concentration/ ppm | +AS (1000 ppm) | +RME (1000 ppm) | +RME + AS (1000 ppm each) |
| I-1-a-25 | 0.8 | 0 | 35 | 20 | 85 |
| I-1-a-29 | 4 | 10 | 15 | 80 | 95 |
| I-1-a-31 | 4 | 0 | 10 | 5 | 35 |

Example 10

1. Herbicidal Pre-Emergence Action

Seeds of monocotyledonous and dicotyledonous weed and crop plants are placed in sandy loam in wood fibre pots and covered with soil. The test compounds, formulated in the form of wettable powders (WP), are then applied to the surface of the covering soil as an aqueous suspension with a water application rate of 600 l/ha (converted), with 0.2% added wetting agent in different dosages.

After the treatment, the pots are placed in a greenhouse and kept under good growth conditions for the test plants. The visual assessment of the emergence damage on the test plants is effected after a test period of approx. three weeks by comparison with the untreated controls (herbicidal effect in percent: 100% effect=the plants have died, 0% effect=like control plants).

In addition to the aforementioned compounds, the following compounds, applied by the pre-emergence method at 320 g/ha a.i., show an effect of ≧80% against *Alopecurus myosuroides, Echinocloa crus-galli, Lolium multiflorum* and *Setaria viridis*: I-1-a-6, I-1-a-7, I-1-a-9, I-1-a-12, I-1-a-13, I-1-a-14, I-1-a-16, I-1-a-19, I-1-a-22, I-1-a-33, I-1-a-34, I-1-a-35, I-1-a-37, I-1-a-38, I-1-a-39, I-1-a-40, I-1-a-41, I-1-b-2, I-1-c-2, I-1-c-3, I-1-c-6, I-2-a-5.

In addition to the aforementioned compounds, the following compounds, applied by the pre-emergence method at 80 g/ha a.i., show an effect of ≧80% against *Alopecurus myosuroides, Echinocloa crus-galli, Lolium multiflorum* and

*Setaria viridis*: I-1-a-1, I-1-a-2, I-1-a-3, I-1-a-4, I-1-a-5, I-1-a-8, I-1-a-17, I-1-a-18, I-1-a-21, I-1-a-25, I-1-b-1, I-1-c-1, I-1-c-4, I-1-c-5.

2. Herbicidal Post-Emergence Action

Seeds of monocotyledonous and dicotyledonous weed and crop plants are placed in sandy loam in wood fibre pots, covered with soil and cultivated in a greenhouse under good growth conditions. Two to three weeks after sowing, the test plants are treated at the one-leaf stage. The test compounds, formulated as wettable powders (WP), are sprayed onto the green parts of the plants in different dosages with a water application rate of 600 l/ha (converted), with 0.2% added wetting agent. After the test plants have been kept in the greenhouse under optimal growth conditions for about three weeks, the effect of the preparations is assessed visually by comparison to untreated controls (herbicidal effect in percent: 100% effect=the plants have died, 0% effect=like control plants).

In addition to the aforementioned compounds, the following compounds, applied by the post-emergence method at 80 g/ha, show an effect of ≧80% against *Alopecurus myosuroides, Avena fatua, Echinocloa crus-galli, Lolium multiflorum, Setaria viridis* and *Veronica persica*: I-1-a-4, I-1-a-5, I-1-a-6, I-1-a-8, I-1-a-17, I-1-a-18, I-1-a-19, I-1-a-25, I-1-a-26, I-1-a-34, I-1-a-39, I-1-b-1, I-1-b-2, I-1-c-4, I-1-c-5, I-2-a-5.

In addition to the aforementioned compounds, the following compounds, applied by the post-emergence method at 80 g/ha, show an effect of ≧80% against *Alopecurus myosuroides, Avena fatua, Echinocloa crus-galli, Lolium multiflorum* and *Setaria viridis*: I-1-a-1, I-1-a-3, I-1-a-7, I-1-a-9, I-1-a-14, I-1-a-35, I-1-a-37, I-1-a-38, I-1-a-40, I-1-a-41, I-1-c-1, I-8-a-1, I-8-c-1, I-8-c-3, I-8-c-5.

Use of Safeners:

If there is to be an additional test as to whether safeners can improve the plant compatibility of test substances in the case of crop plants, the following options are used for applying the safeners:

- Seeds of the crop plants are, before sowing, dressed with safener substance (the amount of safener stated in percent, based on the weight of the seed)
- Before the application of the test substances, the crop plants are sprayed with the safener at a certain application rate per hectare (usually one day before the application of the test substances)
- The safener is applied together with the test substance as a tankmix (the amount of safener is stated in g/ha or as a ratio, based on the herbicide).

Container Trials with Cereals in a Greenhouse

Mefenpyr 1 Day Before Herbicide Application

| | Application rate g a.i./ha | 28 days after application Summer barley observed (%) | 28 days after application Summer wheat observed (%) |
|---|---|---|---|
| Ex. (I-1-a-5) | 25 | 95 | |
| | 12.5 | 65 | 65 |
| Ex. (I-1-a-5) + mefenpyr | 25 + 50 | 75 | |
| | 12.5 + 50 | 35 | 25 |

| | Application rate g a.i./ha | 28 days after application Summer wheat observed (%) |
|---|---|---|
| Ex. (I-1-a-6) | 25 | 85 |
| | 12.5 | 70 |
| Ex. (I-1-a-6) + mefenpyr | 25 + 50 | 60 |
| | 12.5 + 50 | 50 |
| Ex. (I-1-a-7) | 100 | 70 |
| | 50 | 70 |
| | 25 | 50 |
| | 12.5 | 50 |
| Ex. (I-1-a-7) + mefenpyr | 100 + 50 | 30 |
| | 50 + 50 | 20 |
| | 25 + 50 | 20 |
| | 12.5 + 50 | 10 |

| | Application rate g a.i./ha | 10 days after application Summer wheat observed (%) | 28 days after application Summer wheat observed (%) |
|---|---|---|---|
| Ex. (I-1-a-8) | 12.5 | 65 | 98 |
| Ex. (I-1-a-8) + mefenpyr | 12.5 + 50 | 50 | 50 |

| | Application rate g a.i./ha | 28 days after application Summer wheat observed (%) |
|---|---|---|
| Ex. (I-1-a-14) | 50 | 100 |
| | 25 | 99 |
| | 12.5 | 93 |
| Ex. (I-1-a-14) + mefenpyr | 50 + 50 | 85 |
| | 25 + 50 | 85 |
| | 12.5 + 50 | 40 |

| | Application rate g a.i./ha | 28 days after application Summer barley observed (%) | 28 days after application Summer wheat observed (%) |
|---|---|---|---|
| Ex. (I-1-a-15) | 100 | | 60 |
| | 50 | 97 | 40 |
| | 25 | 85 | 30 |
| | 12.5 | 70 | 10 |
| Ex. (I-1-a-15) + mefenpyr | 100 + 50 | | 20 |
| | 50 + 50 | 80 | 10 |
| | 25 + 50 | 80 | 5 |
| | 12.5 + 50 | 20 | 0 |

| | Application rate g a.i./ha | 28 days after application Summer barley observed (%) |
|---|---|---|
| Ex. (I-1-a-17) | 200 | 95 |
| | 100 | 80 |
| | 50 | 40 |
| Ex. (I-1-a-17) + mefenpyr | 200 + 50 | 60 |
| | 100 + 50 | 60 |
| | 50 + 50 | 30 |

| | Application rate g a.i./ha | 28 days after application Summer barley observed (%) | 28 days after application Summer wheat observed (%) |
|---|---|---|---|
| Ex. (I-1-a-19) | 100 | | 85 |
| | 50 | | 70 |
| | 25 | 70 | 20 |
| | 12.5 | | 10 |

-continued

| | Application rate g a.i./ha | 10 days after application Summer wheat observed (%) | 28 days after application Summer wheat observed (%) |
|---|---|---|---|
| Ex. (I-1-a-19) + mefenpyr | 100 + 50 | | 70 |
| | 50 + 50 | | 50 |
| | 25 + 50 | 40 | 20 |
| | 12.5 + 50 | | 0 |
| Ex. (I-1-a-25) | 12.5 | 40 | 70 |
| Ex. (I-1-a-25) + mefenpyr | 12.5 + 50 | 25 | 30 |

| | Application rate g a.i./ha | 10 days after application Summer barley observed (%) |
|---|---|---|
| Ex. (I-1-b-2) | 12.5 | 50 |
| Ex. (I-1-b-2) + mefenpyr | 12.5 + 50 | 20 |

| | Application rate g a.i./ha | 28 days after application Summer wheat observed (%) |
|---|---|---|
| Ex. (I-1-a-37) | 12.5 | 70 |
| Ex. (I-1-a-37) + mefenpyr | 12.5 + 50 | 15 |

Container Tests with Maize-Soya-Cotton in a Greenhouse

Cyprosulfamide 1 Day Before Herbicide Application

| | Application rate g a.i./ha | 28 days after application Maize (Aventura) observed (%) |
|---|---|---|
| Ex. (I-1-a-8) | 50 | 70 |
| | 25 | 60 |
| | 12.5 | 35 |
| Ex. (I-1-a-8) + cyprosulfamide | 50 + 200 | 40 |
| | 25 + 200 | 35 |
| | 12.5 + 200 | 15 |

| | Application rate g a.i./ha | 28 days after application Maize (Arsenal) observed (%) | 28 days after application Maize (Cecilia) observed (%) |
|---|---|---|---|
| Ex. (I-1-a-25) | 100 | 100 | 35 |
| | 50 | 75 | 20 |
| | 25 | 15 | 10 |
| | 12.5 | 5 | 0 |
| Ex. (I-1-a-25) + cyprosulfamide | 100 + 100 | 70 | 10 |
| | 50 + 100 | 50 | 0 |
| | 25 + 100 | 0 | 0 |
| | 12.5 + 100 | 0 | 0 |
| Ex. (I-1-c-2) | 100 | 25 | 75 |
| | 50 | 20 | |
| | 25 | 20 | |
| Ex. (I-1-c-2) + cyprosulfamide | 100 + 200 | 15 | 25 |
| | 50 + 200 | 0 | |
| | 25 + 200 | 0 | |

The invention claimed is:
1. A compound of formula (I)

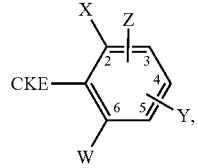

in which
W is hydrogen, chlorine, methyl or ethyl,
X is chlorine, methyl, ethyl, methoxy or ethoxy,
Y is hydrogen, methyl or chlorine,
Z is the group

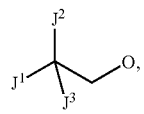

in which $J^1$ and $J^2$ are each independently hydrogen or fluorine and $J^3$ is fluorine, chlorine or trifluoromethyl,
CKE is

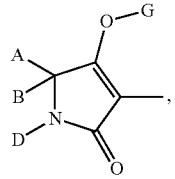

A is hydrogen, in each case optionally mono- to tri-fluorine-substituted $C_1$-$C_4$-alkyl or $C_1$-$C_2$-alkoxy-$C_1$-$C_2$-alkyl, or is cyclopropyl, cyclopentyl or cyclohexyl,
B is hydrogen, methyl or ethyl, or
A, B and the carbon atom to which they are bonded are saturated $C_5$-$C_6$-cycloalkyl in which one ring member is optionally replaced by nitrogen, oxygen or sulphur and which is optionally mono- or di-methyl-, -ethyl-, -methoxymethyl-, -ethoxymethyl-, -methoxyethyl-, -ethoxyethyl-, -trifluoromethyl-, -methoxy-, -ethoxy-, -propoxy-, -butoxy-, -methoxyethoxy-, -ethoxyethoxy-, -allyloxy-, -trifluoroethoxy- or -cyclopropylmethoxy-substituted, where the aforementioned radicals are optionally nitrogen substitutents, or
A, B and the carbon atom to which they are bonded are $C_6$-cycloalkyl which is optionally substituted by an alkylidenediyl group optionally interrupted by one oxygen atom or by an alkylenedioxy group optionally containing two oxygen atoms not directly adjacent, to form a further 5- or 6-membered ring which is optionally mono- or di-methyl-substituted, or
A, B and the carbon atom to which they are bonded are $C_5$-$C_6$-cycloalkyl or $C_5$-$C_6$-cycloalkenyl, in which two substituents together with the carbon atoms to which they are bonded are $C_2$-$C_4$-alkanediyl or $C_2$-$C_4$-alkenediyl or butadienediyl,
D is hydrogen, in each case optionally mono- to tri-fluorine-substituted $C_1$-$C_4$-alkyl, $C_3$-$C_4$-alkenyl, $C_1$-$C_4$-alkoxy-$C_1$-$C_3$-alkyl, or is cyclopropyl, cyclopentyl or cyclohexyl, or A and D together are optionally mono-methyl- or -methoxy-substituted $C_3$-$C_5$-alkanediyl in which one carbon atom is optionally replaced by a carbonyl group, oxygen or sulphur, or is the AD-1 group, or A and D together are $C_3$-$C_5$-alkanediyl which is optionally substituted by an optionally mono- to di-$C_1$-$C_2$-alkyl-substituted alkylenedioxy group containing two oxygen atoms not directly adjacent, to form a further 5-membered ring, G is hydrogen (a), or one of the groups

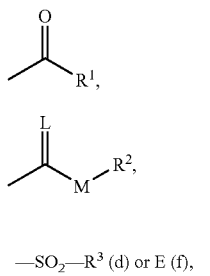

(b)

(c)

—$SO_2$—$R^3$ (d) or E (f), in which
L is oxygen or sulphur,
M is oxygen or sulphur and
E is one metal ion equivalent or one ammonium ion,
$R^1$ is in each case optionally mono-chlorine-substituted $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, or in each case optionally mono-fluorine-, -chlorine-, -methyl- or -methoxy-substituted cyclopropyl or cyclohexyl,
optionally mono-fluorine-, -chlorine-, -bromine-, -cyano-, -nitro-, -methyl-, -methoxy-, -trifluoromethyl- or -trifluoromethoxy-substituted phenyl,
$R^2$ is in each case optionally mono-fluorine-substituted $C_1$-$C_8$-alkyl, $C_2$-$C_6$-alkenyl or $C_1$-$C_4$-alkoxy-$C_2$-$C_3$-alkyl, phenyl or benzyl, and
$R^3$ is $C_1$-$C_8$-alkyl.

2. The compound of the formula (I) according to claim 1, in which
W is hydrogen, methyl or ethyl,
X is chlorine, methyl or ethyl,
Y is hydrogen,
Z is $OCH_2$—$CF_3$ in the 3 position, or
Z is $OCH_2$—$CF_3$ in the 4 position, or
Z is $OCH_2$—$CF_3$ in the 5 position,
CKE is

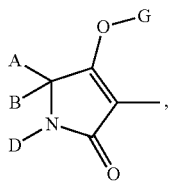

(I)

A is methyl or ethyl,
B is hydrogen or methyl,
A, B and the carbon atom to which they are bonded are saturated $C_5$-$C_6$-cycloalkyl in which one ring member is optionally replaced by oxygen and which is optionally mono- or di-methyl-, -ethyl-, -methoxymethyl-, -methoxy-, -ethoxy-, -propoxy-, -butoxy-, -trifluoroethoxy-substituted, or
A, B and the carbon atom to which they are bonded are $C_6$-cycloalkyl which is optionally substituted by an alkylenedioxy group containing two oxygen atoms not directly adjacent, to form a further 5- or 6-membered ring which is optionally mono- or di-methyl-substituted,
D is hydrogen, or
A and D together are $C_3$-$C_5$-alkanediyl in which one carbon atom is optionally replaced by oxygen, or
A and D together are $C_3$-$C_5$-alkanediyl which is optionally substituted by an optionally mono- to di-methyl-substituted alkylenedioxy group optionally containing two oxygen atoms not directly adjacent, to form a further 5-membered ring,
G is hydrogen (a), or one of the groups

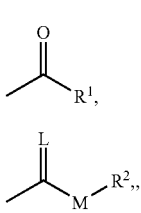

(b)

(c)

in which
L is oxygen,
M is oxygen,
$R^1$ is $C_1$-$C_6$-alkyl, and
$R^2$ is $C_1$-$C_6$-alkyl.

3. A composition for controlling pests and/or undesired plant growth, comprising at least one compound of the formula (I) according to claim 1.

4. A composition comprising an effective content of an active ingredient combination comprising,
(a') at least one compound according to claim 1, and
(b') at least one compound which improves crop plant compatibility which is one of: S1, S2, S3, S4, S5, S6, S7, S8, S9, S10, S11, S12, S13, or S14.

5. The composition according to claim 4, in which the compound which improves crop plant compatibility is cyprosulfamide.

6. The composition according to claim 4, in which the compound which improves crop plant compatibility is mefenpyr-diethyl.

7. A compound of the formula (I-1'-a)

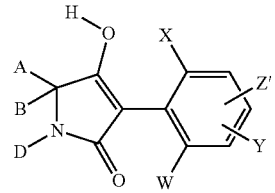

(1-1'-a)

in which
W is hydrogen, chlorine, methyl or ethyl,
X is chlorine, methyl, ethyl, methoxy or ethoxy,
Y is hydrogen, methyl or chlorine,
A is hydrogen, in each case optionally mono- to tri-fluorine:substituted $C_1$-$C_4$-alkyl or $C_1$-$C_2$-alkoxy-$C_1$-$C_2$-alkyl, or is cyclopropyl, cyclopentyl or cyclohexyl,
B is hydrogen, methyl or ethyl, or
A, B and the carbon atom to which they are bonded are saturated $C_5$-$C_6$-cycloalkyl in which one ring member is optionally replaced by nitrogen, oxygen or sulphur and which is optionally mono- or di-methyl-, -ethyl-, -methoxymethyl-, -ethoxymethyl-, -methoxyethyl-, -ethoxyethyl-, -trifluoromethyl-, -methoxy-, -ethoxy-, -propoxy-, -butoxy, -methoxyethoxy-, -ethoxyethoxy, -allyloxy-, -trifluoroethoxy- or -cyclopropylmethoxy-substituted, where the aforementioned radicals are optionally nitrogen substitutents, or A, B and the carbon atom to which they are bonded are $C_6$-cycloalkyl which is optionally substituted by an alkylidenediyl group optionally interrupted by one oxygen atom or by an alkylenedioxy group optionally containing two oxygen atoms not directly adjacent, to form a further 5- or 6-membered ring which is optionally mono- or di-methyl-substituted, or A, B and the carbon atom to which they are bonded are $C_5$-$C_6$-cycloalkyl or $C_5$-$C_6$-cycloalkenyl, in which two substituents together with the carbon atoms to which they are bonded are $C_2$-$C_4$-alkanediyl or $C_2$-$C_4$-alkenediyl or butadienediyl, D is hydrogen, in each case optionally mono- to tri-fluorine-substituted $C_1$-$C_4$-alkyl, $C_3$-$C_4$-alkenyl, $C_1$-$C_4$-alkoxy-$C_1$-$C_3$-alkyl, or is cyclopropyl, cyclopentyl or cyclohexyl, or A and D together are optionally mono-methyl- or -methoxy-substituted $C_3$-$C_5$-alkanediyl in which one carbon atom is optionally replaced by a carbonyl group, oxygen or sulphur, or is the AD-1 group, or A and D together are $C_3$-$C_5$-alkanediyl which is optionally substituted by an optionally mono- to di-$C_1$-$C_2$-alkyl-substituted alkylenedioxy group containing two oxygen atoms not directly adjacent, to form a further 5-membered ring, and Z' is bromine or iodine.

8. A compound of formula (I), selected from the group consisting of:

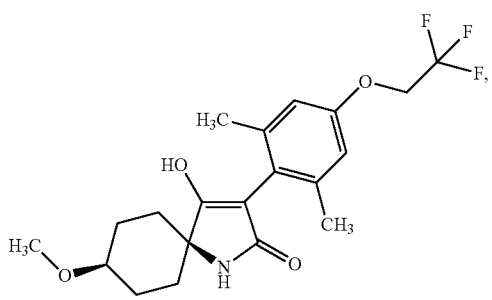

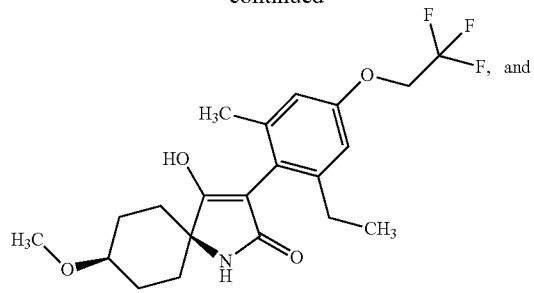

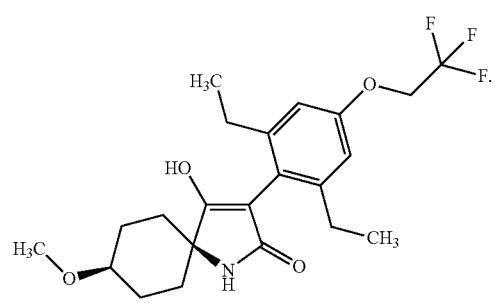

9. A composition for controlling pests and/or undesired plant growth, comprising at least one compound of the formula (I) according to claim 7.

10. A composition comprising an effective content of an active ingredient combination comprising, (a') at least one compound according to claim 7, and (b') at least one compound which improves crop plant compatibility which is one of: S1, S2, S3, S4, S5, S6, S7, S8, S9, S10, S11, S12, S13, or S14.

11. The composition according to claim 10, in which the compound which improves crop plant compatibility is cyprosulfamide.

12. The composition according to claim 10, in which the compound which improves crop plant compatibility is mefenpyr-diethyl.

* * * * *